United States Patent
Cory et al.

(10) Patent No.: US 7,064,193 B1
(45) Date of Patent: Jun. 20, 2006

(54) THERAPEUTIC MOLECULES

(75) Inventors: Suzanne Cory, North Melbourne (AU);
Jerry Adams, North Melbourne (AU);
David C. S. Huang, Carlton (AU);
Liam O'Connor, Coburg (AU);
Andreas Strasser, Ascot Vale (AU);
Hamsa Puthalakath, East Keilor (AU);
Lorraine O'Reilly, Cheltenham (AU)

(73) Assignee: The Walter and Eliza Hall Institute of Medical Research, Victoria (AU)

( * ) Notice: Subject to any disclaimer, the term of this patent is extended or adjusted under 35 U.S.C. 154(b) by 0 days.

(21) Appl. No.: 09/508,832

(22) PCT Filed: Sep. 17, 1998

(86) PCT No.: PCT/AU98/00772

§ 371 (c)(1),
(2), (4) Date: Jul. 10, 2000

(87) PCT Pub. No.: WO99/14321

PCT Pub. Date: Mar. 25, 1999

(30) Foreign Application Priority Data

Sep. 17, 1997 (AU) .................................. PO9263
Sep. 24, 1997 (AU) .................................. PO9373

(51) Int. Cl.
*C12N 15/11* (2006.01)
*C07K 14/00* (2006.01)
(52) U.S. Cl. ...................................... 536/23.1; 530/350
(58) Field of Classification Search ............... 536/23.1, 536/23.5; 530/350
See application file for complete search history.

(56) References Cited

OTHER PUBLICATIONS

Genbank Sequence Database (Accession No. AAQ70754), National Center for Biotechnology Information, National Library of Medicine, Bethesda, Maryland, publicly available Mar. 22, 1995.*
Bowie et al (Science, 1990, 247:1306-1310).*
Burgess et al (J of Cell Bio. 111:2129-2138, 1990).*
Lazar et al (Molecular and Cellular Biology, 1988, 8:1247-1252).*
O'connor et al, (1998, The EMBO Journal, vol. 17, pp. 384-395).*
Oltvai et al (Aug. 27, 1993, Cell 73, 609-619).*
John C. Reed, "Bcl-2 Family Proteins and the Hormonal Control of Cell Life and Death in Normalcy and Neoplasia.", Vitamins and Hormones, vol. 53, pp. 99-138, 1997.
Michael D. Jacobson, "Apoptosis: Bcl-2-related proteins get connected.", Current Biology, vol. 7, No. 5, R277-R281, 1997.

* cited by examiner

*Primary Examiner*—Misook Yu
(74) *Attorney, Agent, or Firm*—Knobbe, Martens, Olson & Bear, LLP

(57) ABSTRACT

The present invention relates generally to novel molecules capable of, inter alia, modulating apoptosis in mammalian cells and to genetic sequences encoding same. More particularly, the present invention relates to a novel member of the Bcl-2 family of proteins, referred to herein as "Bim", and to genetic sequences encoding same. The molecules of the present invention are useful, for example, in therapy, diagnosis, antibody generation and as a screening tool for therapeutic agents capable of modulating physiological cell death or survival and/or modulating cell cycle entry.

7 Claims, 24 Drawing Sheets

| | | | |
|---|---|---|---|
| Bcl-2 | 92 | V V H L T L R Q A G D D F S R R Y R | 109 |
| Bcl-x_L | 85 | A V K Q A L R E A G D E F E L R Y R | 102 |
| Bcl-w | 41 | P L H Q A M R A A G D E F E T R F R | 58 |
| Mcl-1 | 208 | K A L E T L R R V G D G V Q R N H E | 225 |
| Bax | 58 | K L S E C L K R I G D E L D S N M E | 75 |
| Bak | 73 | Q V G R Q L A I I G D D I N R R Y D | 90 |
| Bad | 109 | R Y G R E L R R M S D E F V D S F K | 126 |
| Bik | 56 | A L A L R L A C I G D E M D V S L R | 73 |
| Bid | 85 | N I A R H L A Q V G D S M D R S I P | 102 |
| Hrk | 32 | L T A A R L K A L G D E L H Q R T M | 49 |
| Bim | 147 | W I A Q E L R R I G D E F N A Y Y A | 164 |

Consensus: L R   G D E

B

| | | | |
|---|---|---|---|
| Bim | 142 | M R P E I W I A Q E L R R I G D E F N A | 161 |
| Ced-4 | 278 | Q E E T I R W A Q E L R C L V T T R | 297 |

THERAPEUTIC MOLECULES

This is a 371 of PCT/AU98/00772, filed Sep. 17, 1998.

FIELD OF THE INVENTION

The present invention relates generally to novel molecules capable of, inter alia, modulating apoptosis in mammalian cells and to genetic sequences encoding same. More particularly, the present invention relates to a novel member of the Bcl-2 family of proteins, referred to herein as "Bim", and to genetic sequences encoding same. The molecules of the present invention are useful, for example, in therapy, diagnosis, antibody generation and as a screening tool for therapeutic agents capable of modulating physiological cell death or survival and/or modulating cell cycle entry.

BACKGROUND OF THE INVENTION

Bibliographic details of the publications referred to by author in this specification are collected at the end of the description. Sequence Identity Numbers (SEQ ID NOs.) for the nucleotide and amino acid sequences referred to in the specification are defined following the bibliography. A summary of the SEQ ID NOs. is provided before the Examples.

Apoptosis, the physiologic and genetically modulated process of cell death, is of central importance for modelling tissues and maintaining homeostasis in multicellular organisms (Kerr et al., 1972; Jacobson et al., 1997). Great progress is being made towards understanding the biochemistry underlying this intrinsic suicide program. The cellular apoptotic effector molecules include a set of cysteine proteinases, termed caspases, that degrade critical cellular substrates (Nicholson and Thornberry, 1997). The regulatory machinery that governs the activation of the caspases is less well understood. However a family of proteins of which Bcl-2 is the prototypic molecule (and is referred to as the Bcl-2 family of proteins) plays a central role (Jacobson, 1997; Reed, 1997; Kroemer, 1997).

Bcl-2 was the first intracellular regulator of apoptosis to be identified (Vaux et al., 1988) and high levels enhance cell survival under diverse cytotoxic conditions. Other cellular homologues, such as Bcl-$x_L$ (Boise et al., 1993) and Bcl-w (Gibson et al., 1996), also enhance cell survival, as do more distantly related viral homologues, such as the adenovirus E1B 19K protein (White et al., 1992) and Epstein-Barr virus BHRF-1 (Henderson et al., 1993). However, the family also includes members such as Bax (Oltvai et al., 1993) and Bak (Chittenden et al., 1995; Kiefer et al., 1995; Farrow et al., 1995), which antagonise the activity of the pro-survival proteins and provoke apoptosis when expressed at high concentrations. The relative concentrations of the opposing sub-family members may determine whether the cell lives or dies (Oltvai et al., 1993).

The homology between members of the Bcl-2 family is greatest within four small regions, designated Bcl-2 Homology (BH) regions (Yin et al., 1994; Borner et al., 1994; Chittenden et al., 1995; Gibson et al., 1996; Zha et al., 1996). The N-terminal BH4 domain is restricted to some antagonists of apoptosis, while BH1, BH2 and BH3 can be found in both sub-families (reviewed by Kroemer, 1997). In the tertiary structure determined for Bcl-$x_L$, the BH1, BH2 and BH3 domains form an elongated hydrophobic cleft on the surface of the molecule, stabilised by the BH4 amphipathic helix (Muchmore et al., 1996; Sattler et al., 1997). Most members of the Bcl-2 family contain a C-terminal hydrophobic region, which appears to be important for their localisation to intracytoplasmic membranes (reviewed by Kroemer, 1997).

Protein interactions are an important feature of the Bcl-2 family. Interaction between the pro-survival and pro-apoptotic proteins, such as Bcl-2 with Bax or Bak, requires the BH1 and BH2 domains of the former (Yin et al., 1994; Sedlak et al., 1995; Hanada et al., 1995) and the BH3 domain of the latter (Chittenden et al., 1995; Zha et al., 1996). BH3 peptides bind to the hydrophobic cleft of Bcl-$x_L$ formed by BH1, BH2 and BH3 (Sattler et al., 1997). Although mutagenesis of Bcl-2 and Bcl-$x_L$ initially suggested that their ability to inhibit cell death required binding to a pro-apoptotic family member (Yin et al., 1994), Bcl-$x_L$ mutants have been identified that do not bind Bax or Bak but still block apoptosis (Cheng et al., 1996).

An additional group of pro-apoptotic proteins has recently been described. Bik/Nbk (Boyd et al., 1995; Zha et al., 1996), Bid (Wang et al., 1996) and Hrk (Inohara et al., 1997). The only feature they share in common with each other, or the Bcl-2 family, is the small (9 amino acid) BH3 domain. This region is essential for the ability of these proteins to promote cell death.

In work leading up to the present invention, the inventors have identified a novel member of the Bcl-2 family, designated herein "Bim". In accordance with the present invention, Bim induces cell death and acts as a "death-ligand" for certain members of the pro-survival Bcl-2 family. The identification of this new gene permits the identification and rational design of a range of products for use in therapy, diagnosis, antibody generation and involving modulation of physiological cell death. These therapeutic molecules may act as either antagonists or agonists of Bim's function and will be useful in cancer autoimmune or degenerative disease therapy.

SUMMARY OF THE INVENTION

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

Specific mutations in an amino acid sequence are represented herein as "$X_1nX_2$" where $X_1$ is the original amino acid residue before mutation, n is the residue number and $X_2$ is the mutant amino acid. Reference to Xn is a reference to a particular amino acid in an amino acid sequence where X is the amino acid and n is the residue number. The abbreviation X may be to the three letter or single letter amino acid code.

One aspect of the present invention provides a nucleic acid molecule comprising a nucleotide sequence encoding a polypeptide having one or more of the identifying characteristics of Bim or a derivative or homologue thereof.

Another aspect of the present invention provides a nucleic acid molecule comprising a nucleotide sequence encoding or complementary to a sequence encoding an amino acid sequence substantially as set forth in one of SEQ ID NO: 2, 4, or 6 or a derivative or homologue thereof or having at least about 45% or greater similarity to one or more of SEQ ID NO: 2, 4, or 6, or a derivative or homologue thereof.

Another aspect of the present invention provides a nucleic acid molecule comprising a nucleotide sequence encoding or complementary to a sequence encoding an amino acid sequence substantially as set forth in one of SEQ ID NO: 8 or 10 or a derivative or homologue thereof or having at least about 45% or greater similarity to one or more of SEQ ID NO: 8 or 10 or a derivative or homologue thereof.

Yet another aspect of the present invention contemplates a nucleic acid molecule comprising a nucleotide sequence substantially as set forth in one of SEQ ID NO: 1, 3, or 5 or a derivative or homologue thereof capable of hybridising to one of SEQ ID NO: 1, 3, or 5 under low stringency conditions at 42° C. and which encodes an amino acid sequence corresponding to an amino acid sequence set forth in one of SEQ ID NO: 2, 4 or 6 or a sequence having at least about 45% similarity to one or more of SEQ ID NO: 2, 4, or 6.

Still yet another aspect of the present invention contemplates a nucleic acid molecule comprising a sequence of nucleotides substantially as set forth in SEQ ID NO: 1, 3, or 5.

Still another aspect of the present invention contemplates a nucleic acid molecule comprising a nucleotide sequence substantially as set forth in one of SEQ ID NO: 7 or 9 or a derivative of homologue thereof capable of hybridising to one of SEQ ID NO: 7 or 9 under low stringency conditions at 42° C. and which encodes an amino acid sequence corresponding to an amino acid sequence set forth in one of SEQ ID NO: 8 or 10 or a sequence having at least about 45% similarity to one or more of SEQ ID NO: 8 or 10.

A further aspect of the present invention contemplates a nucleic acid molecule comprising a sequence of nucleotides substantially as set forth in SEQ ID NO: 7 or 9.

Another further aspect of the present invention is directed to an isolated nucleic acid molecule encoding Bim or a derivative thereof, said nucleic acid molecule selected from the list consisting of:

(i) A nucleic acid molecule comprising a nucleotide sequence encoding the amino acid sequence set forth in one of SEQ ID NO: 2, 4, or 6 or a derivative or homologue thereof or having at least about 45% similarity to one or more of SEQ ID NO: 2, 4, or 6.

(ii) A nucleic acid molecule comprising a nucleotide sequence encoding the amino acid sequence set forth in one of SEQ ID NO: 8 or 10 or a derivative or homologue or having at least about 45% similarity to one of SEQ ID NO: 8 or 10.

(iii) A nucleic acid molecule comprising a nucleotide sequence substantially as set forth in one of SEQ ID NO: 1, 3, or 5 or a derivative or homologue thereof.

(iv) A nucleic acid molecule comprising a nucleotide sequence substantially as set forth in one of SEQ ID NO: 7 or 9 or a derivatice or homologue thereof.

(v) A nucleic acid molecule capable of hybridising under low stringency conditions at 42° C. to the nucleotide sequence substantially as set forth in one of SEQ ID NO: 1, 3, or 5 a derivative or homologue and encoding an amino acid sequence corresponding to an amino acid sequence as set forth in one of SEQ ID NO: 2, 4 or 6 a derivative or homologue or a sequence having at least about 45% similarity to one or more of SEQ ID NO: 2, 4, or 6.

(vi) A nucleic acid molecule capable of hybridising under low stringency conditions at 42° C. to the nucleotide sequence substantially as set forth in one of SEQ ID NO: 7 or 9 a derivative or homologue and encoding an amino acid sequence corresponding to an amino acid sequence as set forth in one of SEQ ID NO: 8 or 10 a derivative or homologue or a sequence having at least about 45% similarity to one or more of SEQ ID NO: 8 or 10.

(vii) A nucleic acid molecule capable of hybridising to the nucleic acid molecule of paragraphs (i) or (iii) or (v) under low stringency conditions at 42° C. and encoding an amino acid sequence having at least about 45% similarity to one or more of SEQ ID NO: 2, 4, or 6.

(viii) A nucleic acid molecule capable of hybridising to the nucleic acid molecule of paragraphs (ii) or (iv) or (vi) under low stringency conditions at 42° C. and encoding an amino acid sequence having at least about 45% similarity to one or more of SEQ ID NO: 8 or 10.

(ix) A derivative or mammalian homologue of the nucleic acid molecule of paragraphs (i) or (ii) or (iii) or (iv) or (v) or (vi) or (vii) or (viii).

Yet another further aspect of the present invention is directed to an isolated polypeptide selected from the list consisting of:

(i) A polypeptide having an amino acid sequence substantially as set forth in one of SEQ ID NO: 2, 4, or 6 or derivative or homologue thereof or a sequence having at least about 45% similarity to one or more of SEQ ID NO: 2, 4, or 6.

(ii) A polypeptide having an amino acid sequence substantially as set forth in one of SEQ ID NO: 8 or 10 a derivative or homologue or a sequence having at least about 45% similarity to one or more of SEQ ID NO: 8 or 10.

(iii) A polypeptide encoded by a nucleotide sequence substantially as set forth in one of SEQ ID NO: 1, 3, or 5 or derivative or homologue thereof or a sequence encoding an amino acid sequence having at least about 45% similarity to one or more of SEQ ID NO: 2, 4, or 6.

(iv) A polypeptide encoded by a nucleotide sequence substantially as set forth in one of SEQ ID NO: 7 or 9 or derivative or homologue thereof or a sequence encoding an amino acid sequence having at least about 45% similarity to one or more of SEQ ID NO: 8 or 10.

(v) A polypeptide encoded by a nucleic acid molecule capable of hybridising to the nucleotide sequence as set forth in one of SEQ ID NO: 1, 3, or 5 or derivative or homologue thereof under low stringency conditions at 42° C. and which encodes an amino acid sequence substantially as set forth in SEQ ID NO: 2, 4, or 6 or derivative or homologue thereof or an amino acid sequence having at least about 45% similarity to one or more of SEQ ID NO: 2, 4, or 6.

(vi) A polypeptide encoded by a nucleic acid molecule capable of hybridising to the nucleotide sequence as set forth in one of SEQ ID NO: 7 or 9 or derivative or homologue thereof under low stringency conditions at 42° C. and which encodes an amino acid sequence substantially as set forth in SEQ ID NO: 8 or 10 or derivative or homologue thereof or an amino acid sequence having at least about 45% similarity to one or more of SEQ ID NO: 8 or 10.

(vii) A polypeptide as defined in paragraphs (i) or (ii) or (iii) or (iv) or (v) or (vi) in homodimeric form.

(viii) A polypeptide as defined in paragraphs (i) or (ii) or (iii) or (iv) or (v) or (vi) in heterodimeric form.

Accordingly, a related aspect of the present invention is directed to a variant of an isolated Bim nucleic acid molecule comprising one or more nucleotide mutations in said nucleic acid molecule resulting in at least one amino acid addition, substitution and/or deletion to the polypeptide encoded by said variant wherein said polypeptide cannot bind, couple or otherwise associate with a dynein light chain.

Accordingly, the present invention is more particularly directed to a variant of an isolated Bim nucleic acid molecule comprising one or more nucleotide mutations in said nucleic acid molecule resulting in at least one amino acid addition, substitution and/or deletion in the region of the polypeptide encoded by said variant which binds the dynein light chain wherein said polypeptide cannot bind, couple or otherwise associate with a dynein light chain.

Even more preferably, the present invention is directed to a variant of an isolated murine or human $Bim_L$ nucleic acid molecule comprising one or more nucleotide mutations in said nucleic acid molecule resulting in at least one amino acid addition, substitution and/or deletion in the region defined by amino acid residue numbers 42 to 71 of the polypeptide encoded by said variant wherein said polypeptide cannot bind, couple or otherwise associate with a dynein light chain.

In another preferred embodiment the present invention is directed to a variant of an isolated murine $Bim_{EL}$ nucleic acid molecule comprising one or more nucleotide mutations in said nucleic acid molecule resulting in at least one amino acid addition, substitution and/or deletion in the region defined by amino acid residue numbers 42 to 127 of the polypeptide encoded by said variant wherein said polypeptide cannot bind, couple or otherwise associate with a dynein light chain.

In yet another preferred embodiment the present invention is directed to a variant of an isolated human $Bim_{EL}$ nucleic acid molecule comprising one or more nucleotide mutations in said nucleic acid molecule resulting in at least one amino acid addition, substitution and/or deletion in the region defined by amino acid residue numbers 42 to 131 of the polypeptide encoded by said variant wherein said polypeptide cannot bind, couple or otherwise associate with a dynein light chain.

Accordingly, a preferred embodiment of the present invention is directed to a variant of an isolated human or murine $Bim_L$ nucleic acid molecule comprising one or more nucleotide mutations resulting in the amino acid substitution D51G of the polypeptide encoded by said mutated nucleic acid molecule.

Another preferred embodiment of the present invention is directed to a variant of an isolated human or murine $Bim_L$ nucleic acid molecule comprising one or more nucleotide mutations resulting in the amino acid substitution S53P of the polypeptide encoded by said mutated nucleic acid molecule.

In another preferred embodiment the present invention provides a variant of an isolated human or murine $Bim_L$ nucleic acid molecule comprising one or more nucleotide mutations resulting in the amino acid substitution T54A of the polypeptide encoded by said mutated nucleic acid molecule.

In yet another preferred embodiment the present invention provides a variant of an isolated $Bim_L$ nucleic acid molecule comprising one ore more nucleotide mutations resulting in the amino acid substitutions T54I and N65S of the polypeptide encoded by said mutated nucleic acid molecule.

Accordingly, the present invention is directed to a variant of an isolated Bim polypeptide comprising at least one amino acid addition, substitution and/or deletion wherein said polypeptide cannot bind, couple or otherwise associate with the dynein light chain.

Another aspect of the present invention contemplates a method for modulating expression of Bim in a mammal, said method comprising administering to said mammal a modulating effective amount of an agent for a time and under conditions sufficient to up-regulate or down-regulate or otherwise modulate expression of Bim.

Yet another aspect of the present invention contemplates a method of modulating activity of Bim in a mammal, said method comprising administering to said mammal a modulating effective amount of an agent for a time and under conditions sufficient to increase or decrease Bim activity.

Still another aspect of the present invention contemplates a method of modulating apoptosis in a mammal said method comprising administering to said mammal an effective amount of an agent for a time and under conditions sufficient to modulate the expression of a nucleotide sequence encoding Bim.

Yet another aspect of the present invention contemplates a method of modulating apoptosis in a mammal said method comprising administering to said mammal an effective amount of an agent for a time and under conditions sufficient to modulate the activity of Bim.

Still another aspect of the present invention contemplates a method of modulating apoptosis in a mammal said method comprising administering to said mammal an effective amount of Bim or Bim or derivative thereof.

Accordingly, another aspect of the present invention relates to a method of treating a mammal said method comprising administering to said mammal an effective amount of an agent for a time and under conditions sufficient to modulate the expression of Bim wherein said modulation results in modulation of apoptosis.

In another aspect the present invention relates to a method of treating a mammal said method comprising administering to said mammal an effective amount of an agent for a time and under conditions sufficient to modulate the activity of Bim wherein said modulation results in modulation of apoptosis.

In another aspect the present invention relates to a method of treating a mammal said method comprising administering to said mammal an effective amount of Bim or derivative thereof for a time and under conditions sufficient to modulate apoptosis.

Yet another aspect the present invention relates to a method of treating a mammal said method comprising administering to said mammal an effective amount of Bim or derivative thereof for a time and under conditions sufficient to modulate apoptosis.

In yet another aspect the present invention relates to the use of an agent capable of modulating the expression of Bim in the manufacture of a medicament for the modulation of apoptosis.

Still yet another aspect of the present invention relates to the use of an agent capable of modulating the expression of Bim in the manufacture of a medicament for the modulation of apoptosis.

A further aspect of the present invention relates to the use of Bim or Bim or derivative thereof in the manufacture of a medicament for the modulation of apoptosis.

Another further aspect of the present invention relates to agents for use in modulating Bim expression wherein modulating expression of said Bim modulates apoptosis.

Yet another further aspect of the present invention relates to agents for use in modulating Bim expression wherein modulating expression of said Bim modulates apoptosis.

Still yet another further aspect of the present invention relates to Bim or Bim or derivative thereof for use in modulating apoptosis.

Another aspect of the present invention contemplates a pharmaceutical composition comprising Bim, Bim or derivative thereof or an agent capable of modulating Bim expression or Bim activity together with one or more pharmaceutically acceptable carriers and/or diluents.

Yet another aspect of the present invention is directed to an immunointeractive molecule comprising an antigen binding portion having specificity for Bim or Bim or derivative thereof.

Still another aspect of the present invention contemplates a monoclonal antibody having specificity for Bim or Bim or derivative thereof.

Still yet another aspect of the present invention provides a monoclonal antibody having specificity for $Bim_L$.

A further aspect of the present invention provides a method of detecting an immunointeractive molecule, in a sample, specific for a protein of interest produced by a cell said method comprising contacting the sample to be tested with a population of cells comprising a defined ratio of cells producing the protein of interest and cells not producing the protein of interest for a time and under conditions sufficient for immunointeractive molecules, if present in said sample, to interact with said protein of interest and the subjecting said immunointeractive molecule-protein complex to detecting means.

Another further aspect of the present invention contemplates a method for detecting Bim in a biological sample from a subject said method comprising contacting said biological sample with an immunointeractive molecule as hereinbefore defined specific for Bim or its derivatives thereof for a time and under conditions sufficient for an immunointeractive molecule-Bim complex to form, and then detecting said complex.

Yet another further aspect of the present invention contemplates a method for detecting Bim in a biological sample from a subject said method comprising contacting said biological sample with an immunointeractive molecule as hereinbefore defined specific for Bim or its derivatives thereof for a time and under conditions sufficient for an immunointeractive molecule-Bim complex to form, and then detecting said complex.

Single and three letter abbreviations used throughout the specification are defined in Table 1.

TABLE 1

Single and three letter amino acid abbreviations

| Amino Acid | Three-letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any residue | Xaa | X |

BRIEF DESCRIPTION OF THE DRAWINGS

FIG. 9 is a diagrammatic representation of the BH3 homology regions in the Bcl-2 family. (A) Amino acid sequences (SEQ ID NOS 27–37, respectively in order of appearance) of the human proteins were aligned with the modified method of Feng and Doolittle used by the GCG "PILEUP" program (Feng and Doolittle, 1987). Residues that are identical or very similar (K & R; D & E; V & I; M & L) in >8 of the 11 proteins are shaded in dark grey, while less conserved residues (present in >5/11 proteins) are shaded in light grey. (B) Short stretch of amino acid homology between Bim (SEQ ID NO: 38) and C. elegans Ced-4 (SEQ ID NO: 39); this region overlaps with the BH3 region of Bim, indicated by the box.

DETAILED DESCRIPTION OF THE INVENTION

Figure 1:
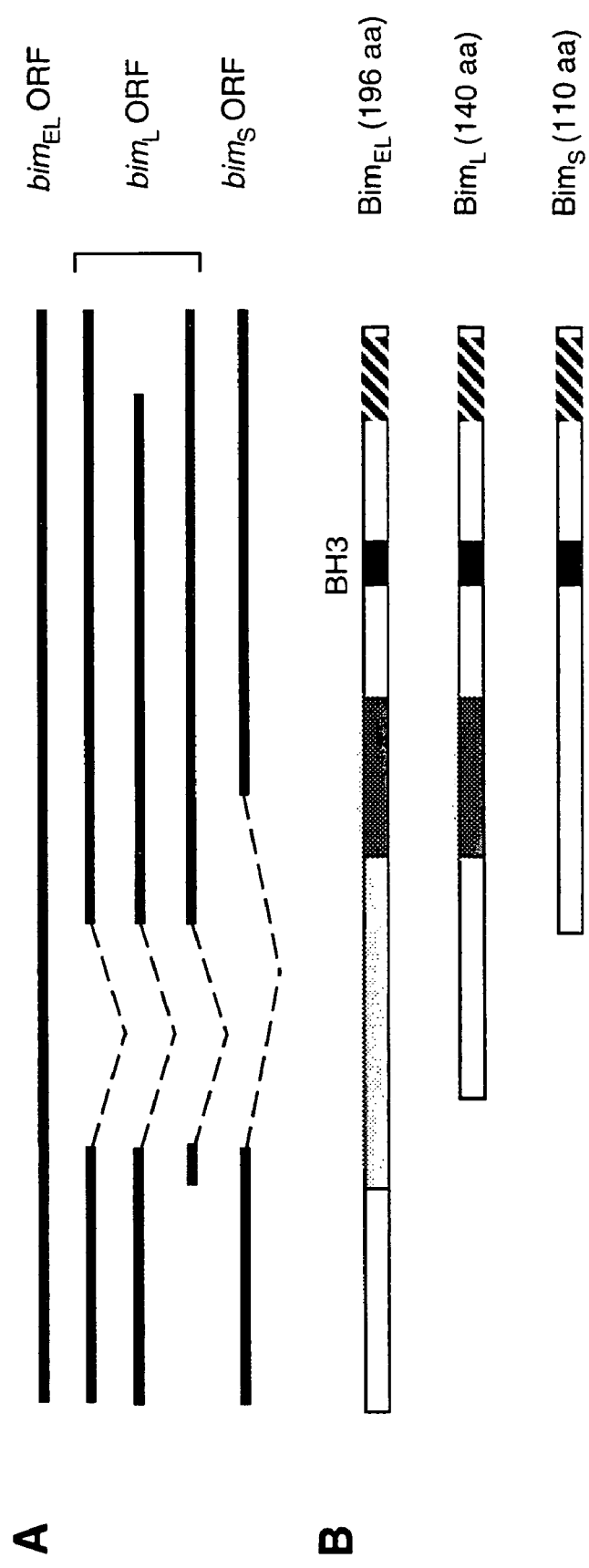
FIG. 1 is a schematic representation of the isolation of cDNAs encoding three isoforms of Bim. (A) Open reading frames of five independent clones isolated by screening a cDNA expression library with recombinant Bcl-2 protein. Dotted lines indicate putative splices and arrows indicate PCR primers spanning the splice sites. (B) Relationship of the three Bim isoforms. The black box denotes the BH3 homology region and the hatched box the predicted hydrophobic region. Regions specific to the larger splice variants are shaded. (C) Sequence alignment of the mouse and human $Bim_{EL}$ polypeptide sequences (SEQ ID NO:5, and 10) using the GCG "BESTFIT" program; identical residues appear on a dark background. The BH3 homology region and the C-terminal hydrophobic region predicted by the Kyte-Doolittle algorithm are boxed. Arrows indicate residues present only in the longer isoforms. Since the nucleotide sequences of the mouse and human cDNAs diverged 5' of the predicted initiating ATG and there are stop codons in all three reading frames upstream of the human open reading frame, that start codon is likely to be correct.
Figure 1:
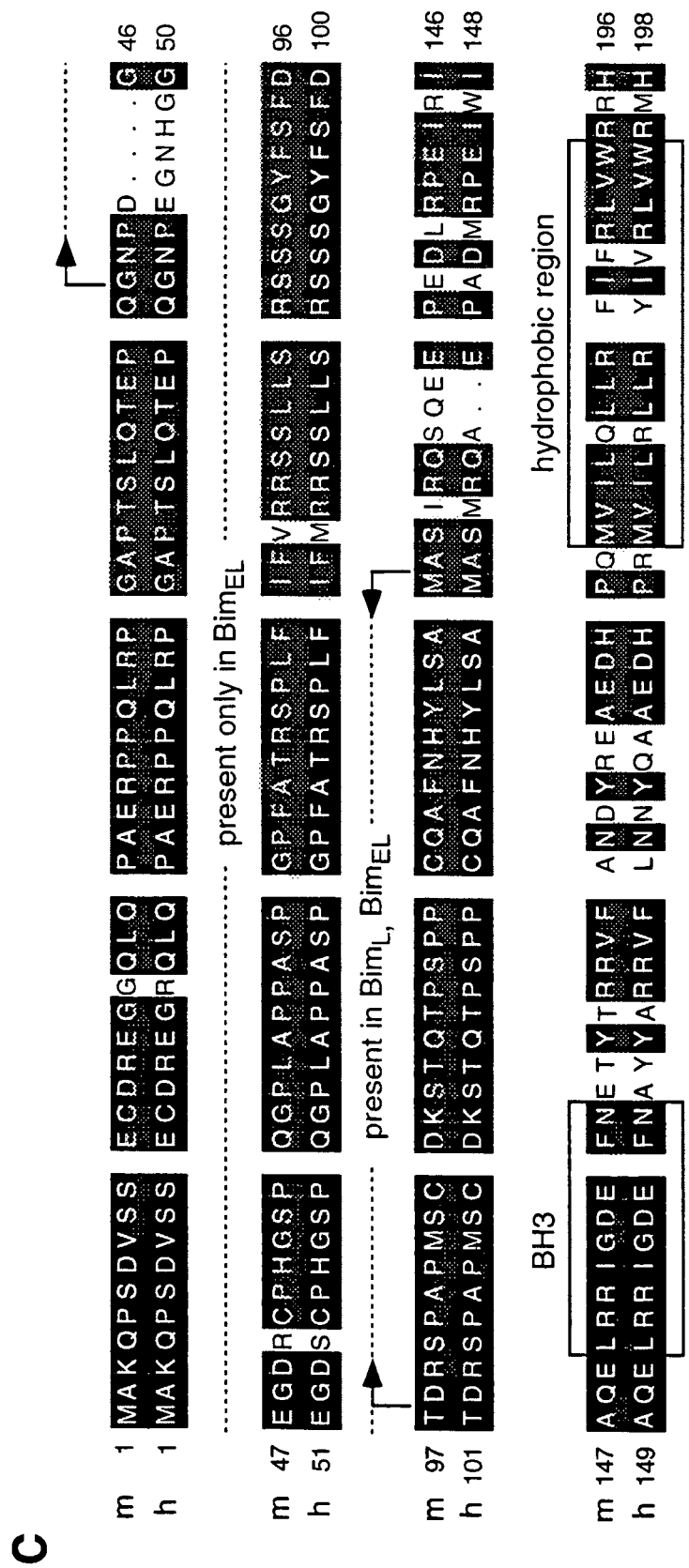

Accordingly, one aspect of the present invention provides a nucleic acid molecule comprising a nucleotide sequence encoding or complementary to a sequence encoding an amino acid sequence substantially as set forth in one of SEQ ID NO: 2, 4, or 6 or a derivative or homologue thereof or having at least about 45% or greater similarity to one or more of SEQ ID NO: 2, 4, or 6, or a derivative or homologue thereof.

Another aspect of the present invention provides a nucleic acid molecule comprising a nucleotide sequence encoding or complementary to a sequence encoding an amino acid sequence substantially as set forth in one of SEQ ID NO: 8 or 10 or a derivative or homologue thereof or having at least about 45% or greater similarity to one or more of SEQ ID NO: 8 or 10 or a derivative or homologue thereof.

The term "similarity" as used herein includes exact identity between compared sequences at the nucleotide or amino acid level. Where there is non-identity at the nucleotide level, "similarity" includes differences between sequences which result in different amino acids that are nevertheless related to each other at the structural, functional, biochemical and/or conformational levels. Where there is non-identity at the amino acid level, "similarity" includes amino acids that are nevertheless related to each other at the structural, functional, biochemical and/or conformational levels. In a particular preferred embodiment, nucleotide and sequence comparisons are made at the level of identity rather than similarity. Any number of programs are available to compare nucleotide and amino acid sequences. Preferred programs have regard to an appropriate alignment. One such program is Gap which considers all possible alignment and gap positions and creates an alignment with the largest number of matched bases and the fewest gaps. Gap uses the alignment method of Needleman and Wunsch. Gap reads a scoring matrix that contains values for every possible GCG symbol match. GAP is available on the ANGIS (Australian National Genomic Information Service) website.

Another aspect of the present invention contemplates a nucleic acid molecule comprising a nucleotide sequence substantially as set forth in one of SEQ ID NO: 1, 3, or 5 or a derivative or homologue thereof capable of hybridising to one of SEQ ID NO: 1, 3, or 5 under low stringency conditions at 42° C. and which encodes an amino acid sequence corresponding to an amino acid sequence set forth in one of SEQ ID NO: 2, 4 or 6 or a sequence having at least about 45% similarity to one or more of SEQ ID NO: 2, 4, or 6.

More particularly the present invention contemplates a nucleic acid molecule comprising a sequence of nucleotides substantially as set forth in SEQ ID NO: 1, 3, or 5.

Another aspect of the present invention contemplates a nucleic acid molecule comprising a nucleotide sequence substantially as set forth in one of SEQ ID NO: 7 or 9 or a derivative of homologue thereof capable of hybridising to one of SEQ ID NO: 7 or 9 under low stringency conditions at 42° C. and which encodes an amino acid sequence corresponding to an amino acid sequence set forth in one of SEQ ID NO: 8 or 10 or a sequence having at least about 45% similarity to one or more of SEQ ID NO: 8 or 10.

More particularly the present invention contemplates a nucleic acid molecule comprising a sequence of nucleotides substantially as set forth in SEQ ID NO: 7 or 9.

Reference herein to a low stringency at 42° C. includes and encompasses from at least about 1% v/v to at least about 15% v/v formamide and from at least about 1M to at least about 2M salt for hybridisation, and at least about 1M to at least about 2M salt for washing conditions. Alternative stringency conditions may be applied where necessary, such as medium stringency, which includes and encompasses from at least about 16% v/v to at least about 30% v/v formamide and from at least about 0.5M to at least about 0.9M salt for hybridisation, and at least about 0.5M to at least about 0.9M salt for washing conditions, or high stringency, which includes and encompasses from at least about 31% v/v to at least about 50% v/v formamide and from at least about 0.01M to at least about 0.15M salt for hybridisation, and at least about 0.01M to at least about 0.15M salt for washing conditions. In general, washing is carried out at $T_m = 69.3 + 0.41$ (G+C)%[19]=$-12°$ C. However, the $T_m$ of a duplex DNA decreases by 1° C. with every increase of 1% in the number of mismatched based pairs (20).

The nucleic acid molecule according to this aspect of the present invention corresponds herein to "Bim". This gene has been determined in accordance with the present invention to induce apoptosis. The product of the Bim gene is referred to herein as "Bim" without limiting this invention in any way, murine Bim has been mapped to murine chromosome 2 at bands F3-G and human Bim has been mapped to the syntenic region on chromosome 2 at bands 2q12–2q13. Bim is known as a "BH3-only" protein since the only Bcl-2 homology region which it encompasses is BH3. It thereby forms a novel member of a Bcl-2 related BH3-only pro-apoptotic group which also comprises, for example, Bik/Nbk, Bid and Hrk. However, Bim is the only BH3-only protein for which splice variants exist, thereby resulting in the expression of a variety of isoforms. $Bim_S$, $Bim_L$ and $Bim_{EL}$ are examples of three said isoforms which differ in both size and potency of functional activity. Murine $Bim_S$, $Bim_L$ and $Bim_{EL}$ are defined by the amino acid sequences set forth in SEQ ID NO: 2, 4 and 6, respectively and human $Bim_L$ and $Bim_{EL}$ are defined by the amino acid sequences set forth in SEQ ID NO: 8 and 10, respectively. The cDNA nucleotide sequences for murine $Bim_S$, $Bim_L$ and $Bim_{EL}$ are defined by the nucleotide sequences set forth in SEQ ID NO: 1, 3 and 5, respectively and human $Bim_L$ and $Bim_{EL}$ are defined by the nucleotide sequences set forth in SEQ ID NO: 7 and 9, respectively.

The nucleic acid molecule encoding Bim is preferably a sequence of deoxyribonucleic acids such as cDNA sequence, an mRNA sequence or a genomic sequence. A genomic sequence may also comprise exons and introns. A genomic sequence may also include a promoter region or other regulatory region.

Reference hereinafter to "Bim" and "Bim" should be understood as a reference to all forms of Bim and Bim, respectively, including, by way of example, the three peptide and cDNA isoforms of $Bim_S$, $Bim_L$ and $Bim_{EL}$ which have been identified as arising from alternative splicing of mRNA and the Bim gene. Reference hereinafter to Bim and Bim in the absence of a reference to its derivatives should be understood to include reference to its derivatives thereof.

The protein and/or gene is preferably from a human, primate, livestock animal (eg. sheep, pig, cow, horse, donkey) laboratory test animal (eg. mouse, rat, rabbit, guinea pig) companion animal (eg. dog, cat), captive wild animal (eg. fox, kangaroo, deer), aves (eg. chicken, geese, duck, emu, ostrich), reptile or fish.

Derivatives include fragments (such as peptides), parts, portions, chemical equivalents, mutants, homologues or mimetics from natural, synthetic or recombinant sources including fusion proteins. Derivatives may be derived from insertion, deletion or substitution of amino acids. Amino acid insertional derivatives include amino and/or carboxylic terminal fusions as well as intrasequence insertions of single or multiple amino acids. Insertional amino acid sequence variants are those in which one or more amino acid residues are introduced into a predetermined site in the protein although random insertion is also possible with suitable screening of the resulting product. Deletional variants are characterized by the removal of one or more amino acids from the sequence. Substitutional amino acid variants are those in which at least one residue in the sequence has been removed and a different residue inserted in its place. Additions to amino acid sequences including fusions with other peptides, polypeptides or proteins. Mutants should be understood to include, but is not limited to, the specific Bim or Bim mutant molecules described herein. Derivatives include, for example, peptides derived from the BH3 region, from the dynein binding region or from a site of phosphorylation. Peptides include, for example, molecules comprising at least 4 contiguous amino acids corresponding to at least 4 contiguous amino acids of Bim as herein defined. Use of the term "polypeptides" herein should be understood to encompass peptides, polypeptides and proteins.

The derivatives of Bim include fragments having particular epitopes or parts of the entire Bim protein fused to peptides, polypeptides or other proteinaceous or non-proteinaceous molecules. For example, Bim or derivative thereof may be fused to a molecule to facilitate its entry into a cell. Analogues of Bim contemplated herein include, but are not limited to, modification to side chains, incorporating of unnatural amino acids and/or their derivatives during peptide, polypeptide or protein synthesis and the use of crosslinkers and other methods which impose conformational constraints on the proteinaceous molecules or their analogues. Derivatives of nucleic acid sequences may similarly be derived from single or multiple nucleotide substitutions, deletions and/or additions including fusion with other nucleic acid molecules. The derivatives of the nucleic acid molecules of the present invention include oligonucleotides, PCR primers, antisense molecules, molecules suitable for use in cosuppression and fusion of nucleic acid molecules.

Examples of side chain modifications contemplated by the present invention include modifications of amino groups such as by reductive alkylation by reaction with an aldehyde followed by reduction with NaBH$_4$; amidination with methylacetimidate; acylation with acetic anhydride; carbamoylation of amino groups with cyanate; trinitrobenzylation of amino groups with 2, 4, 6-trinitrobenzene sulphonic acid (TNBS); acylation of amino groups with succinic anhydride and tetrahydrophthalic anhydride; and pyridoxylation of lysine with pyridoxal-5-phosphate followed by reduction with NaBH$_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carboethoxylation with diethylpyrocarbonate.

Examples of incorporating unnatural amino acids and derivatives during protein synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acid contemplated herein is shown in Table 2.

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexyl-alanine | Mchexa |
| D-α-methylarginine | Dmarg | α-methylcylcopentyl-alanine | Mcpen |
| D-α-methylasparagine | Dmasn | α-methyl-α-napthyl-alanine | Manap |
| D-α-methylaspartate | Dmasp | α-methylpenicill-amine | Mpen |
| D-α-methylcysteine | Dmcys | N-(4-aminobutyl)-glycine | Nglu |
| D-α-methylglutamine | Dmgln | N-(2-aminoethyl)-glycine | Naeg |
| D-α-methylhistidine | Dmhis | N-(3-aminopropyl)-glycine | Norn |
| D-α-methylisoleucine | Dmile | N-amino-α-methyl-butyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)-glycine | Ngln |
| D-α-methylornithine | Dmorn | N-(carbamylmethyl)-glycine | Nasn |
| D-α-methylphenyl-alanine | Dmphe | N-(2-carboxyethyl)-glycine | Nglu |
| D-α-methylproline | Dmpro | N-(carboxymethyl)-glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |

TABLE 2-continued

| Non-conventional amino acid | Code | Non-conventional amino acid | Code |
|---|---|---|---|
| D-N-methylaspartate | Dnmasp | N-(2,2-diphenylethyl)-glycine | Nbhm |
| D-N-methylcysteine | Dnmcys | N-(3,3-diphenylpropyl)-glycine | Nbhe |
| D-N-methylglutamine | Dnmgln | N-(3-guanidinopropyl)-glycine | Narg |
| D-N-methylglutamate | Dnmglu | N-(1-hydroxyethyl)-glycine | Nthr |
| D-N-methylhistidine | Dnmhis | N-(hydroxyethyl))-glycine | Nser |
| D-N-methylisoleucine | Dnmile | N-(imidazolylethyl))-glycine | Nhis |
| D-N-methylleucine | Dnmleu | N-(3-indolylethyl)-glycine | Nhtrp |
| D-N-methyllysine | Dnmlys | N-methyl-γ-amino-butyrate | Nmgabu |
| N-methylcyclohexyl-alanine | Nmchexa | D-N-methylmethionine | Dnmmet |
| D-N-methylornithine | Dnmorn | N-methylcyclopentyl-alanine | Nmcpen |
| N-methylglycine | Nala | D-N-methylphenyl-alanine | Dnmphe |
| N-methylaminoiso-butyrate | Nmaib | D-N-methylproline | Dnmpro |
| N-(1-methylpropyl)-glycine | Nile | D-N-methylserine | Dnmser |
| N-(2-methylpropyl)-glycine | Nleu | D-N-methylthreonine | Dnmthr |
| D-N-methyltryptophan | Dnmtrp | N-(1-methylethyl)-glycine | Nval |
| D-N-methyltyrosine | Dnmtyr | N-methyla-napthyl-alanine | Nmanap |
| D-N-methylvaline | Dnmval | N-methylpenicill-amine | Nmpen |
| γ-aminobutyric acid | Gabu | N-(p-hydroxyphenyl)-glycine | Nhtyr |
| L-t-butylglycine | Tbug | N-(thiomethyl)-glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenyl-alanine | Mhphe |
| L-α-methylisoleucine | Mile | N-(2-methylthioethyl)-glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenyl-alanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenyl-alanine | Nmhphe |
| N-(N-(2,2-diphenylethyl) carbamylmethyl)-glycine | Nnbhm | N-(N-(3,3-diphenylpropyl) carbamylmethyl)glycine | Nnbhe |
| 1-carboxy-1-(2,2-diphenyl-ethylamino)-cyclopropane | Nmbc | | |

Crosslinkers can be used, for example, to stabilise 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogueues by introducing covalent bonds such as forming an amide bond between the N and C termini, between two side chains or between a side chain and the N or C terminus.

The nucleic acid molecule of the present invention is preferably in isolated form or ligated to a vector, such as an expression vector. By "isolated" is meant a nucleic acid molecule having undergone at least one purification step and this is conveniently defined, for example, by a composition comprising at least about 10% subject nucleic acid molecule, preferably at least about 20%, more preferably at least about 30%, still more preferably at least about 40–50%, even still more preferably at least about 60–70%, yet even still more preferably 80–90% or greater of subject nucleic acid molecule relative to other components as determined by molecular weight, encoding activity, nucleotide sequence, base composition or other convenient means. The nucleic acid molecule of the present invention may also be considered, in a preferred embodiment, to be biologically pure.

In a particularly preferred embodiment, the nucleotide sequence corresponding to Bim is a cDNA sequence comprising a sequence of nucleotides as set forth in one of SEQ ID NO: 1, 3 or 5 or is a derivative or homologue thereof including a nucleotide sequence having similarity to one of SEQ ID NO: 1, 3 or 5 and which encodes an amino acid sequence corresponding to an amino acid sequence as set forth in one of SEQ ID NO: 2, 4 or 6 or a sequence having at least about 45% similarity to one or more of SEQ ID NO: 2, 4, or 6.

In another particularly preferred embodiment, the nucleotide sequence corresponding to Bim is a cDNA sequence comprising a sequence of nucleotides as set forth in one of SEQ ID NO: 7 or 9 or is a derivative or homologue thereof including a nucleotide sequence having similarity to one of SEQ ID NO: 7 or 9 and which encodes an amino acid sequence corresponding to an amino acid sequence as set forth in one of SEQ ID NO: 8 or 10 or a sequence having at least about 45% similarity to one or more of SEQ ID NO: 8 or 10.

A derivative of the nucleic acid molecule of the present invention also includes nucleic acid molecules capable of hybridising to the nucleotide sequences as set forth in one of SEQ ID NO: 1, 3, or 5 or SEQ ID NO: 7 or 9 under low stringency conditions. Preferably, said low stringency is at 42° C.

In another embodiment the present invention is directed to an isolated nucleic acid molecule encoding Bim or a derivative thereof, said nucleic acid molecule selected from the list consisting of:

(i) A nucleic acid molecule comprising a nucleotide sequence encoding the amino acid sequence set forth in one of SEQ ID NO: 2, 4, or 6 or a derivative or homologue thereof or having at least about 45% similarity to one or more of SEQ ID NO: 2, 4, or 6.

(ii) A nucleic acid molecule comprising a nucleotide sequence encoding the amino acid sequence set forth in one of SEQ ID NO: 8 or 10 or a derivative or homologue or having at least about 45% similarity to one of SEQ ID NO: 8 or 10.

(iii) A nucleic acid molecule comprising a nucleotide sequence substantially as set forth in one of SEQ ID NO: 1, 3, or 5 or a derivative or homologue thereof.

(iv) A nucleic acid molecule comprising a nucleotide sequence substantially as set forth in one of SEQ ID NO: 7 or 9 or a derivatice or homologue thereof.
(v) A nucleic acid molecule capable of hybridising under low stringency conditions at 42° C. to the nucleotide sequence substantially as set forth in one of SEQ ID NO: 1, 3, or 5 a derivative or homologue and encoding an amino acid sequence corresponding to an amino acid sequence as set forth in one of SEQ ID NO: 2, 4 or 6 a derivative or homologue or a sequence having at least about 45% similarity to one or more of SEQ ID NO: 2, 4, or 6.
(vi) A nucleic acid molecule capable of hybridising under low stringency conditions at 42° C. to the nucleotide sequence substantially as set forth in one of SEQ ID NO: 7 or 9 a derivative or homologue and encoding an amino acid sequence corresponding to an amino acid sequence as set forth in one of SEQ ID NO: 8 or 10 a derivative or homologue or a sequence having at least about 45% similarity to one or more of SEQ ID NO: 8 or 10.
(vii) A nucleic acid molecule capable of hybridising to the nucleic acid molecule of paragraphs (i) or (iii) or (v) under low stringency conditions at 42° C. and encoding an amino acid sequence having at least about 45% similarity to one or more of SEQ ID NO: 2, 4, or 6.
(viii) A nucleic acid molecule capable of hybridising to the nucleic acid molecule of paragraphs (ii) or (iv) or (vi) under low stringency conditions at 42° C. and encoding an amino acid sequence having at least about 45% similarity to one or more of SEQ ID NO: 8 or 10.
(ix) A derivative or mammalian homologue of the nucleic acid molecule of paragraphs (i) or (ii) or (iii) or (iv) or (v) or (vi) or (vii) or (viii).

The nucleic acid molecule may be ligated to an expression vector capable of expression in a prokaryotic cell (e.g. *E. coli*) or a eukaryotic cell (e.g. yeast cells, fungal cells, insect cells, mammalian cells or plant cells). The nucleic acid molecule may be ligated or fused or otherwise associated with a nucleic acid molecule encoding another entity such as, for example, a signal peptide, a cytokine or other member of the Bcl-2 family.

The present invention extends to the expression product of the nucleic acid molecule hereinbefore defined.

The expression product is Bim having an amino acid sequence set forth in one of SEQ ID NO: 2, 4, 6, 8 or 10 or is a derivative or homologue thereof as defined above or is a mammalian homologue having an amino acid sequence of at least about 45% similarity to the amino acid sequence set forth in one of SEQ ID NO: 2, 4, 6, 8 or 10 or derivative or homologue thereof.

Another aspect of the present invention is directed to an isolated polypeptide selected from the list consisting of:
(i) A polypeptide having an amino acid sequence substantially as set forth in one of SEQ ID NO: 2, 4, or 6 or derivative or homologue thereof or a sequence having at least about 45% similarity to one or more of SEQ ID NO: 2, 4, or 6.
(ii) A polypeptide having an amino acid sequence substantially as set forth in one of SEQ ID NO: 8 or 10 a derivative or homologue or a sequence having at least about 45% similarity to one or more of SEQ ID NO: 8 or 10.
(iii) A polypeptide encoded by a nucleotide sequence substantially as set forth in one of SEQ ID NO: 1, 3, or 5 or derivative or homologue thereof or a sequence encoding an amino acid sequence having at least about 45% similarity to one or more of SEQ ID NO: 2, 4, or 6.
(iv) A polypeptide encoded by a nucleotide sequence substantially as set forth in one of SEQ ID NO: 7 or 9 or derivative or homologue thereof or a sequence encoding an amino acid sequence having at least about 45% similarity to one or more of SEQ ID NO: 8 or 10.
(v) A polypeptide encoded by a nucleic acid molecule capable of hybridising to the nucleotide sequence as set forth in one of SEQ ID NO: 1, 3, or 5 or derivative or homologue thereof under low stringency conditions at 42° C. and which encodes an amino acid sequence substantially as set forth in SEQ ID NO: 2, 4, or 6 or derivative or homologue thereof or an amino acid sequence having at least about 45% similarity to one or more of SEQ ID NO: 2, 4, or 6.
(vi) A polypeptide encoded by a nucleic acid molecule capable of hybridising to the nucleotide sequence as set forth in one of SEQ ID NO: 7 or 9 or derivative or homologue thereof under low stringency conditions at 42° C. and which encodes an amino acid sequence substantially as set forth in SEQ ID NO: 8 or 10 or derivative or homologue thereof or an amino acid sequence having at least about 45% similarity to one or more of SEQ ID NO: 8 or 10.
(vii) A polypeptide as defined in paragraphs (i) or (ii) or (iii) or (iv) or (v) or (vi) in homodimeric form.
(viii) A polypeptide as defined in paragraphs (i) or (ii) or (iii) or (iv) or (v) or (vi) in heterodimeric form.

As defined earlier, the present invention extends to peptides or derivatives thereof of Bim. Preferably, said peptide comprises at least 5 contiguous amino acids of the polypeptide defined in SEQ ID NO:2, 4, 6, 8 or 10. The present invention also extends to nucleic acid molecules encoding the peptides of the present invention.

Another aspect of the present invention provides a nucleic acid molecule comprising a nucleotide sequence encoding a polypeptide having one or more of the identifying characteristics of Bim or a derivative or homologue thereof.

Reference herein to "identifying characteristics" of Bim includes one or more of the following features:
(i) A polypeptide which induces apoptosis.
(ii) A polypeptide having an amino acid sequence substantially as set forth in SEQ ID NO:2, 4, 6, 8 or 10 or a derivative or homologue thereof.
(iii) A polypeptide having an amino acid sequence of at least 45% similarity to SEQ ID NO:2, 4, 6, 8 or 10.
(iv) A polypeptide as defined in paragraph (ii) or (iii) which induces apoptosis.
(v) A polypeptide encoded by a nucleic acid sequence substantially as set forth in SEQ ID NO:1, 3, 5, 7 or 9 or derivative or homologue thereof.
(vi) A polypeptide encoded by a nucleic acid molecule capable of hybridising to the nucleotide sequence as set forth in one of SEQ ID NO: 1, 3, 5, 7 or 9 under low stringency conditions at 42° C.
(vii) A polypeptide as defined in paragraph (v) or (vi) which induces apoptosis.
(viii) A non-apoptosis inducing derivative of the polypeptide defined in paragraphs (i) to (vii).

The present invention should be understood to extend to the expression product of the nucleic acid molecule according to this aspect of the present invention.

Although not intending to limit the invention to any one theory or mode of action, the BH3 region is responsible for some of the cytotoxic actions of Bim. The BH3 region forms an amphipathic helix that interacts with the elongated hydrophobic cleft formed by the BH1, BH2 and BH3 regions of pro-survival molecules such as, for example, Bcl-XL. The pro-apoptotic action of Bim reflects its ability to bind to the anti-apoptotic members of the Bcl-2 family. Bim is the only BH3-only protein for which splice variants have been described. Isoforms such as $Bim_S$, $Bim_L$ and $Bim_{EL}$ interact in vivo with Bcl-2 family members but induce cell death with different degrees of cytotoxicity. $Bim_S$, for example, is a more potent inducer of cell death than $Bim_L$ or $Bim_{EL}$.

Still without limiting the invention to any one theory or mode of action, the pro-apoptotic activity of Bim is thought to be regulated both at the transcriptional level and at the post-translational level. Sequence analysis of the non-coding 5' region of Bim has revealed a number of putative binding sites for transcription factors. $Bim_L$ and $Bim_{EL}$ can bind to dynein light chain. Dynein light chain is a highly conserved protein which is a component of the dynein motor complex. The dynein motor complex moves vesicles along microtubules but may also carry out other functions.

In living cells Bim is bound to the dynein motor complex and associated with the microtubular network. When cells are stressed, for example by removal of growth factors or UV irradiation, Bim is rapidly released from the dynein motor complex, but remains still bound to dynein light chain. Thus the breakage occurs between dynein light chain and dynein intermediate chain. This change in subcellular localisation is thought to constitute an upstream signalling event, probably for cell death.

The interaction of Bim with the dynein motor complex regulates the pro-apoptotic activity of Bim. It is thought that when Bim is released from the microtubular network it is free to interact with Bcl-2 and its homologueues and will thereby prevent their pro-survival function. Consistent with this idea, $Bim_S$, which does not bind to dynein light chain, is not associated with the microtubular network and is a much more potent killer than $Bim_L$ or $Bim_{EL}$. Single amino acid mutations in Bim that abolish binding to dynein light chain have been identified.

Accordingly, a related aspect of the present invention is directed to a variant of an isolated Bim nucleic acid molecule comprising one or more nucleotide mutations in said nucleic acid molecule resulting in at least one amino acid addition, substitution and/or deletion to the polypeptide encoded by said variant wherein said polypeptide cannot bind, couple or otherwise associate with a dynein light chain.

Preferably, the mutation results in an altered amino acid sequence in the region which binds the dynein light chain. For example, in murine and human $Bim_L$ this corresponds to the region defined by amino acid residue numbers 42 to 71, in murine $Bim_{EL}$ this region is defined by amino acid residue numbers 42 to 127 and in human $Bim_{EL}$ amino acid residue numbers 42 to 131. The present invention should be understood to extend to variants of Bim comprising a mutation resulting in an amino acid addition, substitution and/or deletion in a region functionally equivalent to the regions hereinbefore defined.

Accordingly, the present invention is more particularly directed to a variant of an isolated Bim nucleic acid molecule comprising one or more nucleotide mutations in said nucleic acid molecule resulting in at least one amino acid addition, substitution and/or deletion in the region of the polypeptide encoded by said variant which binds the dynein light chain wherein said polypeptide cannot bind, couple or otherwise associate with a dynein light chain.

Even more preferably, the present invention is directed to a variant of an isolated murine or human $Bim_L$ nucleic acid molecule comprising one or more nucleotide mutations in said nucleic acid molecule resulting in at least one amino acid addition, substitution and/or deletion in the region defined by amino acid residue numbers 42 to 71 of the polypeptide encoded by said variant wherein said polypeptide cannot bind, couple or otherwise associate with a dynein light chain.

In another preferred embodiment the present invention is directed to a variant of an isolated murine $Bim_{EL}$ nucleic acid molecule comprising one or more nucleotide mutations in said nucleic acid molecule resulting in at least one amino acid addition, substitution and/or deletion in the region defined by amino acid residue numbers 42 to 127 of the polypeptide encoded by said variant wherein said polypeptide cannot bind, couple or otherwise associate with a dynein light chain.

In yet another preferred embodiment the present invention is directed to a variant of an isolated human $Bim_{EL}$ nucleic acid molecule comprising one or more nucleotide mutations in said nucleic acid molecule resulting in at least one amino acid addition, substitution and/or deletion in the region defined by amino acid residue numbers 42 to 131 of the polypeptide encoded by said variant wherein said polypeptide cannot bind, couple or otherwise associate with a dynein light chain.

Mutations contemplated by the present invention which occur in combination with one or more mutations in another location are also contemplated by the present invention.

Preferably, the nucleotide mutation is a mutation to the human or murine $Bim_L$ and results in an amino acid substitution of one or more of D51, S53, T54 and/or N65. Preferred mutations include one or more of D51G, S53P, T54A, T54I and/or N65S. Accordingly, a preferred embodiment of the present invention is directed to a variant of an isolated human or murine $Bim_L$ nucleic acid molecule comprising one or more nucleotide mutations resulting in the amino acid substitution D51G of the polypeptide encoded by said mutated nucleic acid molecule.

Another preferred embodiment of the present invention is directed to a variant of an isolated human or murine $Bim_L$ nucleic acid molecule comprising one or more nucleotide mutations resulting in the amino acid substitution S53P of the polypeptide encoded by said mutated nucleic acid molecule.

In another preferred embodiment the present invention provides a variant of an isolated human or murine $Bim_L$ nucleic acid molecule comprising one or more nucleotide mutations resulting in the amino acid substitution T54A of the polypeptide encoded by said mutated nucleic acid molecule.

In yet another preferred embodiment the present invention provides a variant of an isolated $Bim_L$ nucleic acid molecule comprising one ore more nucleotide mutations resulting in the amino acid substitutions T54I and N65S of the polypeptide encoded by said mutated nucleic acid molecule.

The present invention extends to the expression products of the nucleic acid molecule variants defined according to this aspect of the present invention.

Accordingly, the present invention is directed to a variant of an isolated Bim polypeptide comprising at least one amino acid addition, substitution and/or deletion wherein said polypeptide cannot bind, couple or otherwise associate with the dynein light chain.

Preferably said addition, substitution and/or deletion is of any one or more amino acid residues located in the region which binds the dynein light chain. Even more preferably said region is defined by residue numbers 42 to 71 in murine and human $Bim_L$, residue numbers 42 to 127 in murine $Bim_{EL}$ and residue numbers 42 to 131 in human $Bim_{EL}$.

Preferably said amino acid addition, substitution and/or deletion is a substitution of D51, S53, T54 and/or N65 of human or murine $Bim_L$. Preferred mutations include one or more of D51G, S53P, T54A, T54I and N65S. Most preferably said mutation is D51G or S53P or T54A or T54I and N65S.

The present invention extends to derivatives of the nucleic acid molecules and polypeptides according to this aspect of the present invention. The term "derivatives" should be understood as previously defined.

As hereinbefore defined, reference to "Bim" and "Bim" should be understood to include reference to the variant molecules defined according to this aspect of the present invention.

The Bim of the present invention may be in multimeric form meaning that two or more molecules are associated together. Where the same Bim molecules are associated together, the complex is a homomultimer. An example of a homomultimer is a homodimer. Where at least one Bim is associated with at least one non-Bim molecule, then the complex is a heteromultimer such as a heterodimer. A heteromultimer may include a molecule of another member of the Bcl-2 family or other molecule capable of modulating apoptosis.

The present invention contemplates, therefore, a method for modulating expression of Bim in a mammal, said method comprising administering to said mammal a modulating effective amount of an agent for a time and under conditions sufficient to up-regulate or down-regulate or otherwise modulate expression of Bim. For example, Bim antisense sequences such as oligonucleotides may be introduced into a cell to enhance the ability of that cell to survive. Conversely, a nucleic acid molecule encoding Bim or a derivative thereof may be introduced to decrease the survival capacity of any cell expressing the endogenous Bim gene. Modulation of the expression of Bim should be understood to extend to modulating transcriptional and translation events such as the splicing pattern of Bim RNA.

Another aspect of the present invention contemplates a method of modulating activity of Bim in a mammal, said method comprising administering to said mammal a modulating effective amount of an agent for a time and under conditions sufficient to increase or decrease Bim activity.

Modulation of said activity by the administration of an agent to a mammal can be achieved by one of several techniques, including but in no way limited to introducing into said mammal a proteinaceous or non-proteinaceous molecule which:

(i) modulates expression of Bim;
(ii) functions as an antagonist of Bim;
(iii) functions as an agonist of Bim.

Said proteinaceous molecule may be derived from natural or recombinant sources including fusion proteins or following, for example, natural product screening. Said non-proteinaceous molecule may be, for example, a nucleic acid molecule or may be derived from natural sources, such as for example natural product screening or may be chemically synthesised. The present invention contemplates chemical analogues of Bim capable of acting as agonists or antagonists of Bim. Chemical agonists may not necessarily be derived from Bim but may share certain conformational similarities. Alternatively, chemical agonists may be specifically designed to mimic certain physiochemical properties of Bim. Antagonists may be any compound capable of blocking, inhibiting or otherwise preventing Bim from carrying out its normal or pathological biological functions. Antagonists include, but are not limited to parts of Bim or peptides thereof, monoclonal antibodies specific for Bim or parts of Bim, and antisense nucleic acids or oligonucleotides which prevent transcription or translation of Bim genes or mRNA in mammalian cells. Agonists of Bim and Bim include, for example, the derivative or variant molecules or peptides hereinbefore defined which interact with anti-apoptotic molecules such as Bcl-2, to prevent their functional activity thereby promoting apoptosis. Agonists may also include molecules capable of disrupting or preventing binding of Bim to the dynein light chain or the interaction of dynein light chain with dynein intermediate chain.

Said proteinaceous or non-proteinaceous molecule may act either directly or indirectly to modulate the expression of Bim or the activity of Bim. Said molecule acts directly if it associates with Bim or Bim to modulate the expression or activity of Bim or Bim. Said molecule acts indirectly if it associates with a molecule other than Bim or Bim which other molecule either directly or indirectly modulates the expression or activity of Bim or Bim. Accordingly, the method of the present invention encompasses the regulation of Bim or Bim expression or activity via the induction of a cascade of regulatory steps which lead to the regulation of Bim or Bim expression or activity. Increased Bim expression or Bim activity is useful, for example, for treatment or prophylaxis in conditions such as cancer and deletion of autoreactive lymphocytes in autoimmune disease. Decreased Bim expression or Bim activity is useful in regulating inhibition or prevention of cell death or degeneration such as under cytotoxic conditions during, for example, γ-irradiation and chemotherapy or during HIV/AIDS or other viral infections, ischaemia or myocardial infarction. Since Bim is expressed in germ cells, modulating Bim expression or Bim activity is useful, for example, as a contraceptive or method of sterilisation by preventing generation of fertile sperm.

Another aspect of the present invention contemplates a method of modulating apoptosis in a mammal said method comprising administering to said mammal an effective amount of an agent for a time and under conditions sufficient to modulate the expression of a nucleotide sequence encoding Bim.

Yet another aspect of the present invention contemplates a method of modulating apoptosis in a mammal said method comprising administering to said mammal an effective amount of an agent for a time and under conditions sufficient to modulate the activity of Bim.

Still another aspect of the present invention contemplates a method of modulating apoptosis in a mammal said method comprising administering to said mammal an effective amount of Bim or Bim or derivative thereof.

The Bim, Bim or derivative thereof or agent used may also be linked to a targeting means such as a monoclonal antibody, which provides specific delivery of the Bim, Bim or agent to the target cells.

In a preferred embodiment of the present invention, the Bim, Bim or agent used in the method is linked to an antibody specific for said target cells to enable specific delivery to these cells.

Administration of the Bim, Bim or agent, in the form of a pharmaceutical composition, may be performed by any convenient means. Bim, Bim or agent of the pharmaceutical composition are contemplated to exhibit therapeutic activity when administered in an amount which depends on the particular case. The variation depends, for example, on the human or animal and the Bim, Bim or agent chosen. A broad range of doses may be applicable. Considering a patient, for example, from about 0.01 mg to about 10 mg of Bim or agent may be administered per kilogram of body weight per day. Dosage regimes may be adjusted to provide the optimum therapeutic response. For example, several divided doses may be administered daily, weekly, monthly or other suitable time intervals or the dose may be proportionally reduced as indicated by the exigencies of the situation. The Bim or agent may be administered in a convenient manner such as by the oral, intravenous (where water soluble), intranasal, intraperitoneal, intramuscular, subcutaneous, intradermal or suppository routes or implanting (e.g. using slow release molecules). With particular reference to use of Bim or agent, these peptides may be administered in the form of pharmaceutically acceptable nontoxic salts, such as acid addition salts or metal complexes, e.g. with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. If the active ingredient is to be administered in tablet form, the tablet may contain a binder such as tragacanth, corn starch or gelatin; a disintegrating agent, such as alginic acid; and a lubricant, such as magnesium stearate.

A further aspect of the present invention relates to the use of the invention in relation to mammalian disease conditions. For example, the present invention is particularly applicable to, but in no way limited to, use in therapy or prophylaxis in relation to cancer, degenerative diseases, autoimmune disorders, viral infections or for germ cell regulation.

Accordingly, another aspect of the present invention relates to a method of treating a mammal said method comprising administering to said mammal an effective amount of an agent for a time and under conditions sufficient to modulate the expression of Bim wherein said modulation results in modulation of apoptosis.

In another aspect the present invention relates to a method of treating a mammal said method comprising administering to said mammal an effective amount of an agent for a time and under conditions sufficient to modulate the activity of Bim wherein said modulation results in modulation of apoptosis.

In another aspect the present invention relates to a method of treating a mammal said method comprising administering to said mammal an effective amount of Bim or derivative thereof for a time and under conditions sufficient to modulate apoptosis.

Yet another aspect the present invention relates to a method of treating a mammal said method comprising administering to said mammal an effective amount of Bim or derivative thereof for a time and under conditions sufficient to modulate apoptosis.

In yet another aspect the present invention relates to the use of an agent capable of modulating the expression of Bim or derivative thereof in the manufacture of a medicament for the modulation of apoptosis.

Another aspect of the present invention relates to the use of an agent capable of modulating the expression of Bim or derivative thereof in the manufacture of a medicament for the modulation of apoptosis.

A further aspect of the present invention relates to the use of Bim or Bim or derivative thereof in the manufacture of a medicament for the modulation of apoptosis.

Still yet another aspect of the present invention relates to agents for use in modulating Bim expression wherein modulating expression of said Bim modulates apoptosis.

A further aspect of the present invention relates to agents for use in modulating Bim expression wherein modulating expression of said Bim modulates apoptosis.

Another aspect of the present invention relates to Bim or Bim or derivative thereof for use in modulating apoptosis.

In a related aspect of the present invention, the mammal undergoing treatment may be human or an animal in need of therapeutic of prophylactic treatment.

In yet another further aspect the present invention contemplates a pharmaceutical composition comprising Bim, Bim or derivative thereof or an agent capable of modulating Bim expression or Bim activity together with one or more pharmaceutically acceptable carriers and/or diluents. Bim, Bim or said agent are referred to as the active ingredients.

The pharmaceutical forms suitable for injectable use include sterile aqueous solutions (where water soluble) and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as licithin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thirmerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When Bim, Bim and Bim modulators are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained. Preferred compositions or preparations according to the present invention are prepared so that an oral dosage unit form contains between about 0.1 µg and 2000 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound may be incorporated into sustained-release preparations and formulations.

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from 0.5 µg to about 2000 mg. Expressed in proportions, the active compound is generally present in from about 0.5 µg to about 2000 mg/ml of carrier. In the case of compositions containing supplementary active ingredients, the dosages are determined by reference to the usual dose and manner of administration of the said ingredients.

The pharmaceutical composition may also comprise genetic molecules such as a vector capable of transfecting target cells where the vector carries a nucleic acid molecule capable of modulating Bim expression or Bim activity. The vector may, for example, be a viral vector.

Conditions requiring modulation of physiological cell death include enhancing survival of cells utilising, for example, antisense sequence in patients with neurodegenerative diseases, myocardial infarction, muscular degenerative disease, hypoxia, ischaemia, HIV infection or for prolonging the survival of cells being transplanted for treatment of disease. Alternatively, the molecules of the present invention are useful for, for example, reducing the survival capacity of tumour cells or autoreactive lymphocytes. The anti-sense sequence may also be used for modifying in vitro behaviour of cells, for example, as part of a protocol to develop novel lines from cell types having unidentified growth factor requirements; for facilitating isolation of hybridoma cells producing monoclonal antibodies, as described below; and for enhancing survival of cells from primary explants while they are being genetically modified.

Still another aspect of the present invention is directed to an immunointeractive molecule comprising an antigen binding portion having specificity for Bim or Bim or derivative thereof.

Reference to "immunointeractive molecule" should be understood as a reference to any molecule comprising an antigen binding portion or a derivative of said molecule. Examples of molecules contemplated by this aspect of the present invention include, but are not limited to, monoclonal and polyclonal antibodies (including synthetic antibodies, hybrid antibodies, humanized antibodies, catalytic antibodies) and T cell antigen binding molecules. Preferably, said immunoreactive molecule is a monoclonal antibody.

According to this preferred embodiment there is provided a monoclonal antibody having specificity for Bim or Bim or derivative thereof.

Reference to a molecule "having specificity for Bim or Bim" should be understood as a reference to a molecule, such as a monoclonal antibody, having specificity for any one or more epitopes of Bim or Bim. These epitopes may be conformational epitopes, linear epitopes or a combination of conformational and linear epitopes of either the native Bim or Bim molecule or the denatured molecule.

More preferably there is provided a monoclonal antibody having specificity for $Bim_L$.

The immunointeractive molecules of the present invention may be naturally occurring, synthetic or recombinantly produced. For example, monoclonal or polyclonal antibodies may be selected from naturally occurring antibodies to Bim or Bim or may be specifically raised to Bim or Bim. In the case of the latter, Bim or Bim may first need to be associated with a carrier molecule. The antibodies and/or recombinant Bim of the present invention are particularly useful as therapeutic or diagnostic agents. Alternatively, fragments of antibodies may be used such as Fab fragments. Furthermore, the present invention extends to recombinant and synthetic antibodies, to antibody hybrids and to antibodies raised against non-Bim antigens but which are cross-reactive with any one or more Bim epitopes. A "synthetic antibody" is considered herein to include fragments and hybrids of antibodies. The antibodies of this aspect of the present invention are particularly useful for immunotherapy and may also be used as a diagnostic tool for assessing apoptosis or monitoring the program of a therapeutic regime.

For example, Bim and Bim can be used to screen for naturally occurring antibodies to Bim and Bim, respectively. These may occur, for example in some degenerative disorders.

For example, specific antibodies can be used to screen for Bim proteins. The latter would be important, for example, as a means for screening for levels of Bim in a cell extract or other biological fluid or purifying Bim made by recombinant means from culture supernatant fluid. Techniques for the assays contemplated herein are known in the art and include, for example, sandwich assays, ELISA and flow cytometry.

It is within the scope of this invention to include any second antibodies (monoclonal, polyclonal or fragments of antibodies) directed to the first mentioned antibodies discussed above. Both the first and second antibodies may be used in detection assays or a first antibody may be used with a commercially available anti-immunoglobulin antibody. An antibody as contemplated herein includes any antibody specific to any region of Bim.

Both polyclonal and monoclonal antibodies are obtainable by immunization with the protein or peptide derivatives and either type is utilizable for immunoassays. The methods of obtaining both types of sera are well known in the art. Polyclonal sera are less preferred but are relatively easily prepared by injection of a suitable laboratory animal with an effective amount of Bim, or antigenic parts thereof, collecting serum from the animal, and isolating specific sera by any of the known immunoadsorbent techniques. Although antibodies produced by this method are utilizable in virtually any type of immunoassay, they are generally less favoured because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art. (See, for example Douillard and Hoffman, Basic Facts about Hybridomas, in *Compendium of Immunology* Vol II, ed. by Schwartz, 1981; Kohler and Milstein, *Nature* 256: 495–499, 1975; *European Journal of Immunology* 6: 511–519, 1976).

Screening for immunointeractive molecules, such as antibodies, can be a time consuming and labour intensive process. However, the inventors have developed a rapid and efficient flow cytometric screening procedure for the identification of immunointereactive molecules, and in particular antibodies, directed to low abundance cytoplasmic proteins such as, but not limited to, Bim.

The method according to this aspect of the present invention is based on the analysis of a population of cells, following the incubation of these cells with the antibody of interest together with or separately to a reporter molecule, said population of cells comprising both cells expressing the protein of interest and cells which do not express the protein of interest. This analysis is preferably flow cytometric analysis and the cells expressing the protein of interest are preferably transfected with a nucleic acid molecule encoding the protein of interest to thereby express high levels of said protein. Where the protein is a cytoplasmic protein the cells are permeabalised prior to incubation with the antibody of interest. By screening a population of cells comprising both cells which do not express and cells which do express the protein of interest, determination of which antibodies bind to the protein of interest is simplified since where the subject antibody is directed to the protein of interest, a double fluorscence peak is observed. The lower intensity peak represents background staining while the higher fluorscence intensity peak is the result of specific staining. Where the antibody being screened according to this method is not directed to the protein of interest, a single peak of low fluorescence intensity is observed. Antibodies not specific to the protein of interest but bound to some unknown epitope present in both populations of cells produces a single peak with high fluorscence intensity. This technique provides a rapid and accurate method of screening for immunointeractive molecules directed to low abundance intracytoplasmic molecules.

Accordingly, another aspect of the present invention provides a method of detecting an immunointeractive molecule, in a sample, specific for a protein of interest produced by a cell said method comprising contacting the sample to be tested with a population of cells comprising a defined ratio of cells producing the protein of interest and cells not producing the protein of interest for a time and under conditions sufficient for immunointeractive molecules, if present in said sample, to interact with said protein of interest and the subjecting said immunointeractive molecule-protein complex to detecting means.

Preferably said immunointeractive molecule is an antibody.

More preferably, said detecting means comprises an anti-immunogloblin antibody labelled with a reporter molecule capable of giving a detectable signal. Even more preferably said reporter molecule is fluorochrome.

Reference to "sample" should be understood as a reference to any sample potentially comprising an immunointeractive molecule, such as an antibody. Said immunointeractive molecule may be produced by natural, recombinant or synthetic means.

The method of the present invention is predicated on subjecting the cells incubated with the sample of the present invention to flow cytometric analysis to produce a fluorescent signal wherein a differential fluorescent signal is indicative of antibody binding to the target protein expressed by said cells.

The method exemplified herein is directed, but not limited to, screening for immunointeractive molecules comprising an antigen binding site directed to epitopes of Bim. The promyelomoncytic cell line FDC-P1 is transfected with a Bcl-2 expression construct and an EE (Glu—Glu) epitope-tagged Bim construct. A 1:1 ratio of Bcl-2 transfected cells to Bim transfected cells are fixed, permeablised and contacted with the immunointeractive molecule of interest, such as a hybridoma supernatant. Visualisation of antibodies bound intracellular molecules can be achieved via a number of techniques known to those skilled in the art, including, for example, the use of fluorescently labelled reporter molecules. Where the antibody of interest is directed to Bim, a double fluorescence peak is observed, the lower intensity peak representing background staining of the Bcl-2 transfected negative control cells.

In another aspect of the present invention, the molecules of the present invention are also useful as screening targets for use in applications such as the diagnosis of disorders which are regulated by Bim. For example, screening for the levels of Bim or Bim in tissue as an indicator of a predisposition to, or the development or, cancer, a degenerative disease or infertility. The screening of this aspect of the present invention may also be directed to detecting mutations in Bim or Bim.

Accordingly, another aspect of the present invention contemplates a method for detecting Bim in a biological sample from a subject said method comprising contacting said biological sample with an immunointeractive molecule as hereinbefore defined specific for Bim or its derivatives thereof for a time and under conditions sufficient for an immunointeractive molecule-Bim complex to form, and then detecting said complex.

Preferably said immunointeractive molecule is an antibody. Even more preferably said antibody is a monoclonal antibody.

Reference to biological sample according to this aspect of the present invention should be understood as a reference to any sample comprising tissue from a subject said "tissue" should be understood in its broadest sense to include biological fluid, biopsy samples or any other form of tissue or fluid or extracts therefrom such as DNA or RNA properties.

Still another aspect of the present invention contemplates a method for detecting Bim in a biological sample from a subject said method comprising contacting said biological sample with an immunointeractive molecule as hereinbefore defined specific for Bim or its derivatives thereof for a time and under conditions sufficient for an immunointeractive molecule-Bim complex to form, and then detecting said complex.

Reference to an "immunointeractive" molecule should be understood as a reference to any molecule which couples, binds or otherwise associates with Bim or Bim or derivative thereof. For example said interactive molecule may be a nucleic acid molecule or an anti-nuclear antibody.

The presence of Bim may be determined in a number of ways such as by Western blotting, ELISA or flow cytometry procedures. Bim mRNA or DNA may be detected, for example, by in situ hybridization or Northern blotting or Southern blotting. These, of course, include both single-site and two-site or "sandwich" assays of the non-competitive types, as well as in the traditional competitive binding assays. These assays also include direct binding of a labelled antibody to a target.

Sandwich assays are among the most useful and commonly used assays and are favoured for use in the present invention. A number of variations of the sandwich assay technique exist, and all are intended to be encompassed by the present invention. Briefly, in a typical forward assay, an unlabelled antibody is immobilized on a solid substrate and the sample to be tested brought into contact with the bound molecule. After a suitable period of incubation, for a period of time sufficient to allow formation of an antibody-antigen complex, a second antibody specific to the antigen, labelled with a reporter molecule capable of producing a detectable signal is then added and incubated, allowing time sufficient for the formation of another complex of antibody-antigen-labelled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of hapten. Variations on the forward assay include a simultaneous assay, in which both sample and labelled antibody are added simultaneously to the bound antibody. These techniques are well known to those skilled in the art, including any minor variations as will be readily apparent. In accordance with the present invention the sample is one which might contain Bim including cell extract, tissue biopsy or possibly serum, saliva, mucosal secretions, lymph, tissue fluid and respiratory fluid. The sample is, therefore, generally a biological sample comprising biological fluid but also extends to fermentation fluid and supernatant fluid such as from a cell culture.

In the typical forward sandwich assay, a first antibody having specificity for the Bim or antigenic parts thereof, is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2–40 minutes) and under suitable conditions (e.g. 25° C.) to allow binding of any subunit present in the antibody. Following the incubation period, the antibody subunit solid phase is washed and dried and incubated with a second antibody specific for a portion of the hapten. The second antibody is linked to a reporter molecule which is used to indicate the binding of the second antibody to the hapten.

An alternative method involves immobilizing the target molecules in the biological sample and then exposing the immobilized target to specific antibody which may or may not be labelled with a reporter molecule. Depending on the amount of target and the strength of the reporter molecule signal, a bound target may be detectable by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radioisotopes) and chemiluminescent molecules.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In all cases, the enzyme-labelled antibody is added to the first antibody hapten complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of hapten which was present in the sample. "Reporter molecule" also extends to use of cell agglutination or inhibition of agglutination such as red blood cells on latex beads, and the like.

Alternately, fluorescent compounds, such as fluorecein and rhodamine, may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic color visually detectable with a light microscope.

As in the EIA, the fluorescent labelled antibody is allowed to bind to the first antibody-hapten complex. After washing off the unbound reagent, the remaining tertiary complex is then exposed to the light of the appropriate wavelength the fluorescence observed indicates the presence of the hapten of interest. Immunofluorescene and EIA techniques are both very well established in the art and are particularly preferred for the present method. However, other reporter molecules, such as radioisotope, chemiluminescent or bioluminescent molecules, may also be employed.

The present invention also contemplates genetic assays such as involving PCR analysis to detect Bim or its derivatives.

Further features of the present invention are more fully described in the following examples. It is to be understood, however, that this detailed description is included solely for the purposes of exemplifying the present invention. It should not be understood in any way as a restriction on the broad description of the invention as set out above.

SUMMARY OF SEQ ID NO:

| Sequence | SEQ ID NO: |
|---|---|
| nucleotide sequence of murine $Bim_S$ | 1 |
| amino acid sequence of murine $Bim_S$ | 2 |
| nucleotide sequence of murine $Bim_L$ | 3 |
| amino acid sequence of murine $Bim_L$ | 4 |
| nucleotide sequence of murine $Bim_{EL}$ | 5 |
| amino acid sequence of murine $Bim_{EL}$ | 6 |
| nucleotide sequence of human $Bim_L$ | 7 |
| amino acid sequence of human $Bim_L$ | 8 |
| nucleotide sequence of human $Bim_{EL}$ | 9 |
| amino acid sequence of human $Bim_{EL}$ | 10 |
| peptides | 11–13 |
| oligonucleotide primers | 14–26 |

EXAMPLE 1

Isolation of a Novel Gene Encoding a Bcl-2-Binding Protein

In an attempt to identify novel proteins that bind to Bcl-2, we used recombinant human Bcl-2 protein, labelled with $^{32}P$ (Blanar and Rutter, 1992), to screen a bacteriophage λ cDNA expression library constructed from the $p53^{-/-}$ T lymphoma cell line K052DA20 (Strasser et al., 1994). A screen of $10^6$ clones yielded 5 independent clones which encoded the same novel protein, which we named Bim, for Bcl-2 interacting mediator of cell death. Sequence analysis of the bim cDNAs revealed three variants of the coding region, apparently produced by alternative splicing (FIG. 1A). Reverse transcriptase-PCR on mRNA from K052DA20 cells gave PCR products of the sizes expected for each of these transcripts, which we designated $bim_{EL}$, $Bim_L$ and $bim_S$, although the last was in low yield (data not shown). The predicted proteins $Bim_{EL}$, $Bim_L$ and $Bim_S$ comprise 196, 140 and 110 amino acid residues (FIG. 1B). Hybridising human embryo and liver cDNA libraries with mouse bim cDNA yielded human cDNAs encoding $Bim_L$ and $Bim_{EL}$. Human $Bim_{EL}$ is a protein of 198 residues, 89% identical to its mouse counterpart (FIG. 1C), and human $Bim_L$ (138 residues) is 85% identical to mouse $Bim_L$.

Bim has no substantial homology with any protein in current databases. However, scrutiny of its sequence (FIG. 1C) revealed a stretch of nine amino acids corresponding to a BH3 homology region (Boyd et al., 1995; Chittenden et al., 1995). Apart from this region, the Bim sequence is unrelated to that of any other BH3-containing protein; it contains no other BH region, nor indeed any other known functional motif. The protein does have a C-terminal hydrophobic region (FIG. 1C), raising the possibility that it associates with membranes.

Figure 2:
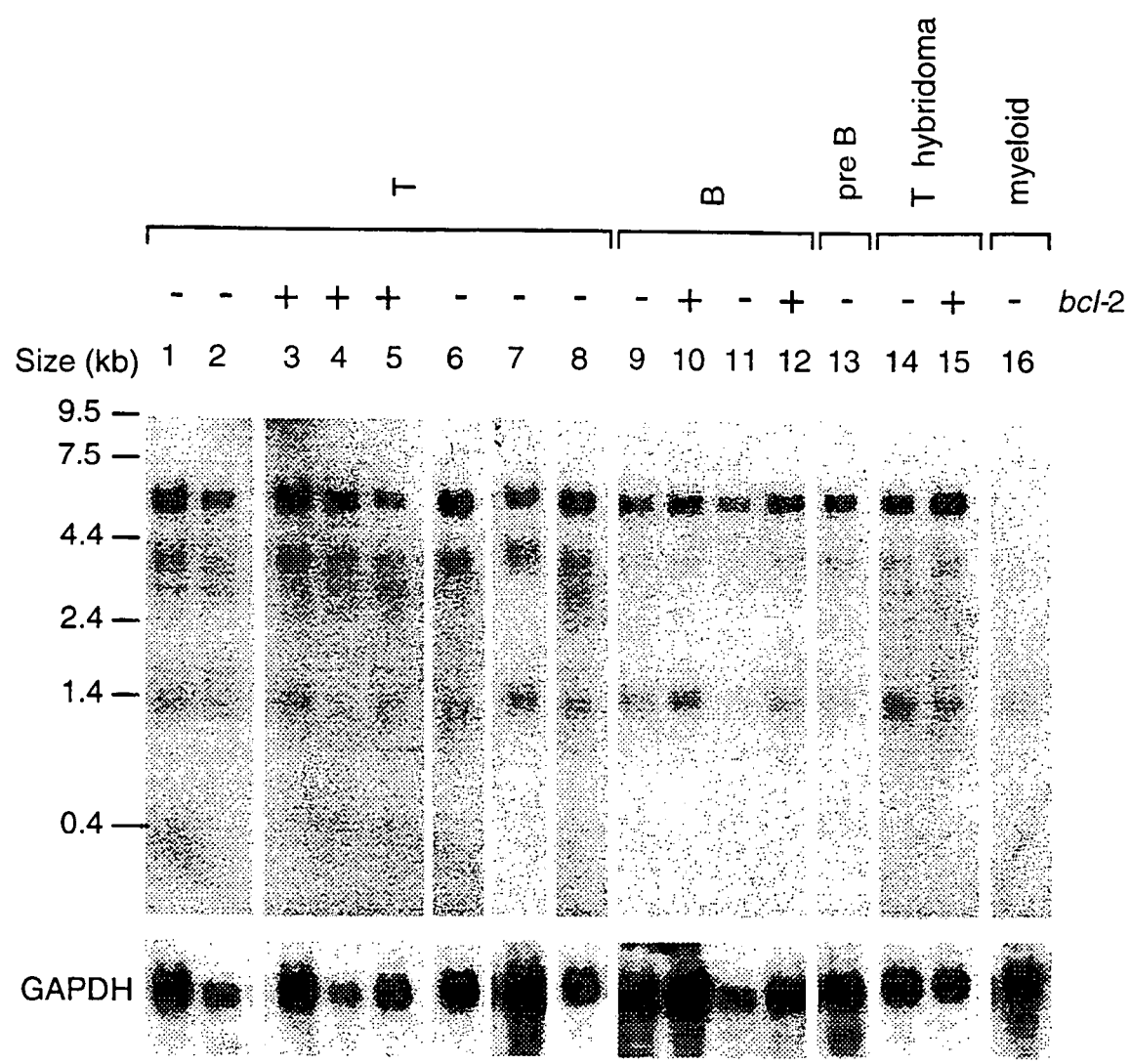
FIG. 2 is a photographic representation of the expression of bim RNA in haematopoietic cell lines. Northern blot analysis of polyA$^+$ RNA, using a mouse bim cDNA probe. The RNAs were derived from the following mouse lines: T lymphomas KO52DA20 (lanes 1 to 5), WEHI 703 (lane 6), WEHI 707 (lane 7) and WEHI 7.1 (lane 8); B lymphomas CH1 (lanes 9, 10) and WEHI 231 (lanes 11, 12); pre-B lymphoma WEHI 415 (lane 13); T hybridoma B6.2.16 BW2 (lanes 14, 15); myeloid progenitor FDC-P1 (lane 16). Those lines that harbour a bcl-2 expression vector or transgene are indicated. Certain RNAs were isolated from cells exposed to cytotoxic conditions: 1 μM dexamethasone (14 hr, lanes 2 and 4; 24 hr, lane 5); γ-irradiation (10 Gy) (lane 5). Samples from a single autoradiograph have been rearranged in order electronically.

Northern blot analysis showed that bim was expressed in a number of B and T lymphoid cell lines, although not in the myeloid line FDC-P1 (FIG. 2). A major transcript of 5.7 kb and minor transcripts of 3.8, 3.0, and 1.4 kb were detected. Neither the level nor relative abundance of these transcripts changed significantly in K052DA20 cells induced to undergo apoptosis by treatment with dexamethasone (FIG. 2, compare lanes 1 and 2, and lanes 3 and 4) or exposure to γ-radiation (compare lanes 1 and 5). Overexpression of bcl-2 in several of the lines did not affect bim mRNA levels (FIG. 2).

EXAMPLE 2

Bim Localises to Cytoplasmic Membranes

Figure 3:
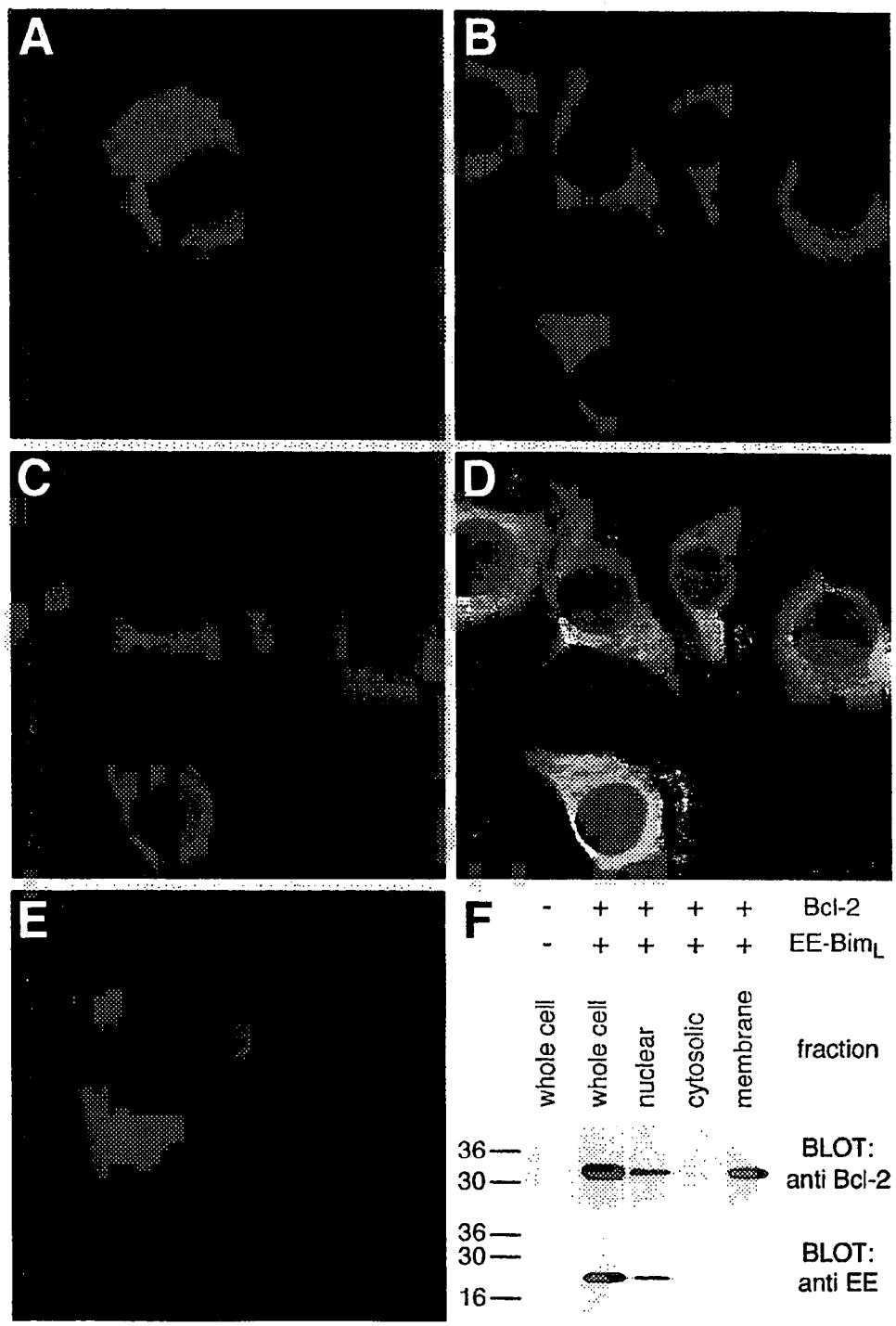
FIG. 3 is a photographic representation of the localisation of Bim protein to intracellular membranes. (A) L929 fibroblasts transiently transfected with EE-tagged $Bim_L$ were fixed, permeabilised and stained with the anti-EE antibody; fluorescence was visualised by confocal microscopy. (B) and (C) L929 cells stably co-expressing human Bcl-2 and EE-tagged $Bim_L$ were stained with anti-human Bcl-2 antibody (B) or anti-EE antibody (C). (D) Images from the staining with anti-EE (B) and anti-Bcl-2 (C) were superimposed; co-localisation is indicated by (*colour) staining.

The presence of the C-terminal hydrophobic domain in Bim prompted us to investigate its subcellular localisation. L929 fibroblasts were transiently transfected with an expression vector encoding $Bim_L$ tagged with an N-terminal EE-epitope, and the permeabilised cells were stained with an anti-EE monoclonal antibody. Confocal microscopy revealed that $Bim_L$ was cytoplasmic and apparently associated with intracellular membranes (FIG. 3A). We also introduced the $Bim_L$ vector into L929 cells stably infected with a human Bcl-2 encoding retrovirus (Lithgow et al., 1994). The similarity of the anti-EE staining pattern of these cells (FIG. 3C) to that of those expressing $Bim_L$ alone (FIG. 3A) demonstrated that high concentrations of Bcl-2 did not perturb the localisation of $Bim_L$. The pattern of $Bim_L$ staining was similar to that reported for Bcl-2 (Monaghan et al., 1992; Krajewski et al., 1993; Lithgow et al., 1994), and overlaying the images obtained from the same cells stained with anti-Bcl-2 (FIG. 3B) and anti-EE (FIG. 3C) antibodies showed that the two proteins co-localised (FIG. 3D).

EXAMPLE 3

Overexpression of Bim Kills Cells by a Pathway Requiring Caspases

Figure 4:
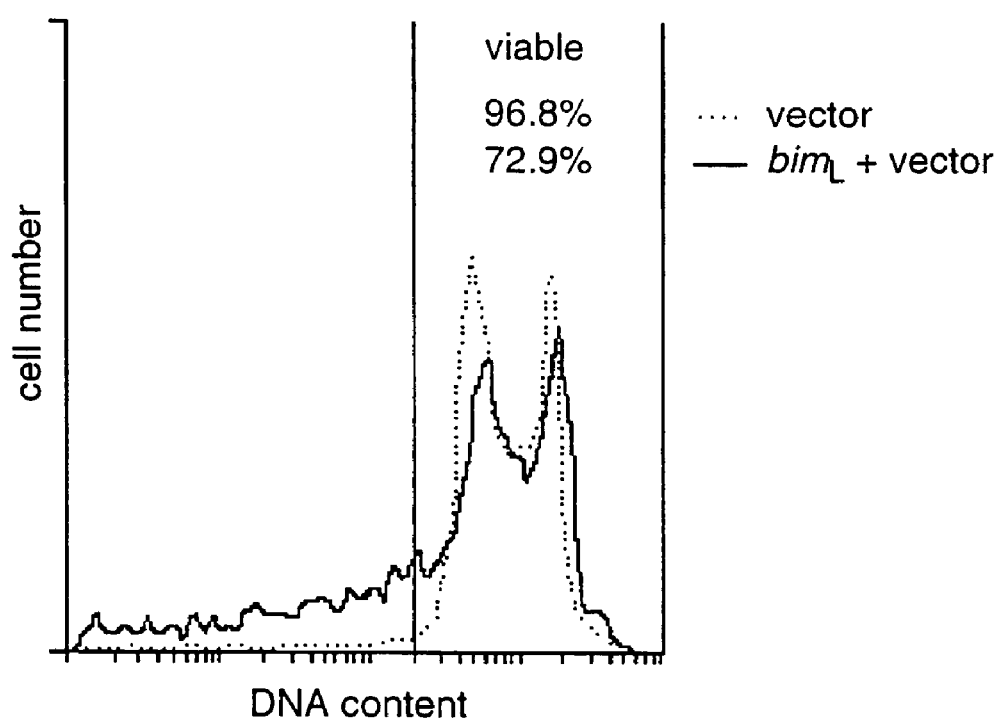
FIG. 4 is a graphical representation demonstrating that Bim induces apoptosis and can be inhibited by p35 and Bcl-2 but not CrmA. (A) Flow cytometric DNA analysis (see Materials and Methods) of 293T cells transfected 24 h previously with EE-$bim_L$ plasmid (0.5 μg). (B) Kinetics of apoptosis elicited by EE-$bim_L$ plasmid (0.5 μg), assessed as in A. (C) Cell viability 48 h after transfection with 0.1, 0.2 or 0.5 μg of EE-$bim_L$ plasmid alone (black bars) or together with 0.5 μg of wild-type or mutant p35 or crmA plasmid (grey bars). (D) Cell viability 48 h after transfection with 0.1, 0.2 or 0.5 μg of EE-$bim_L$ plasmid together with 0.5 μg of the indicated wt or mutant bcl-2 plasmids. C and D show the percentage of viable Bim-expressing cells, determined by DNA FACS analysis, as in A, and are the mean±SD of 3 or more independent experiments.
Figure 4:
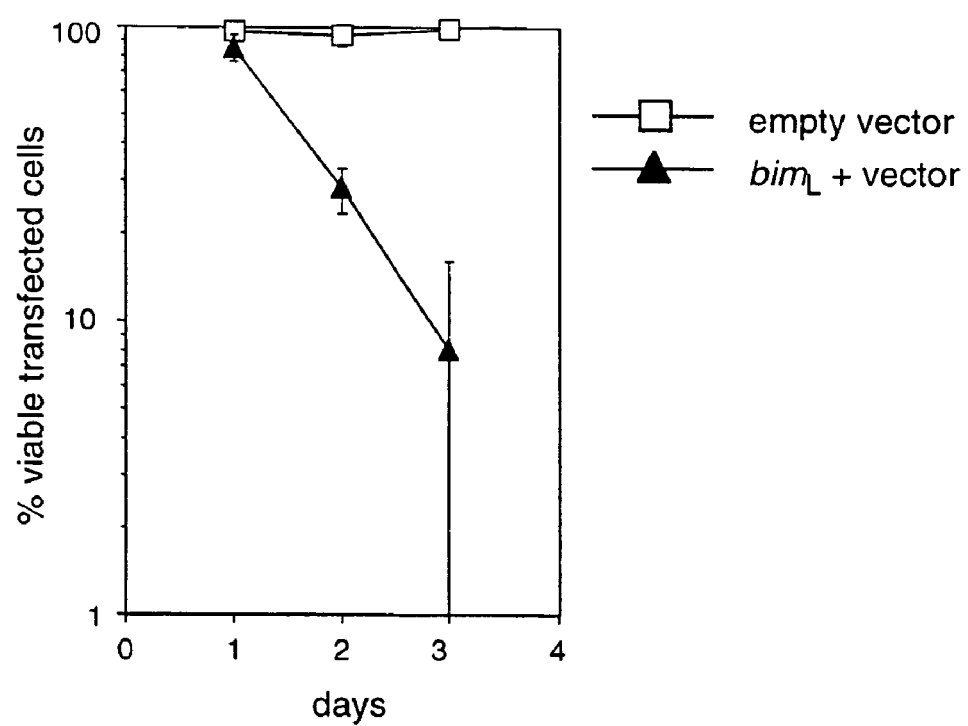
Figure 4:
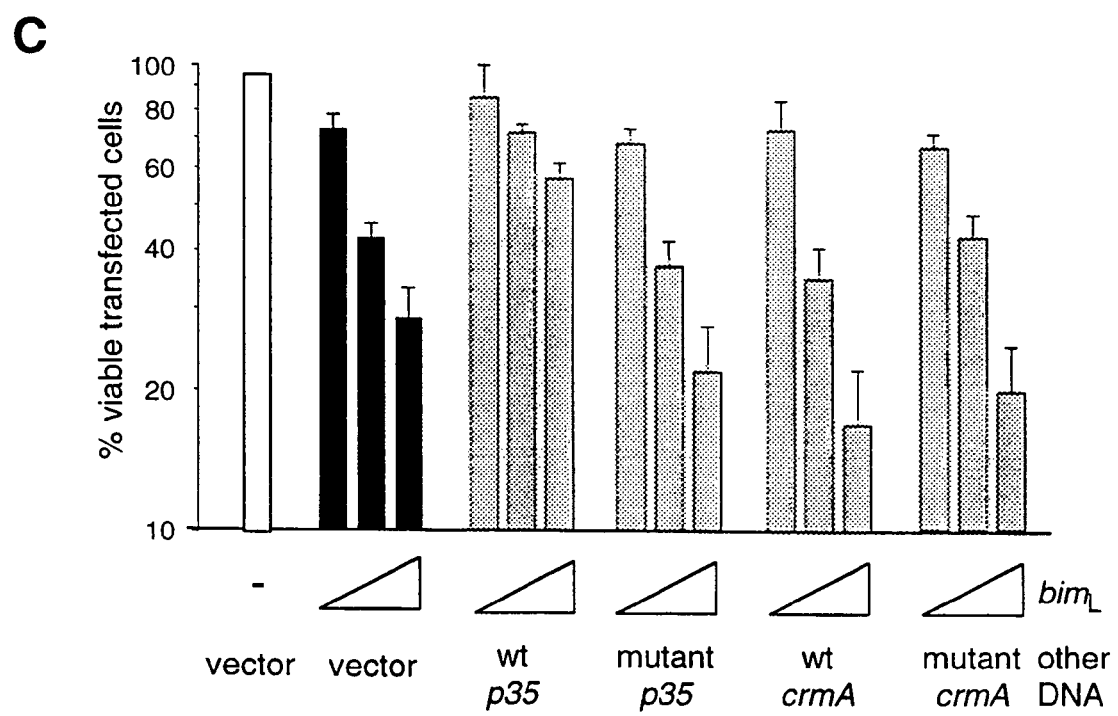
Figure 4:
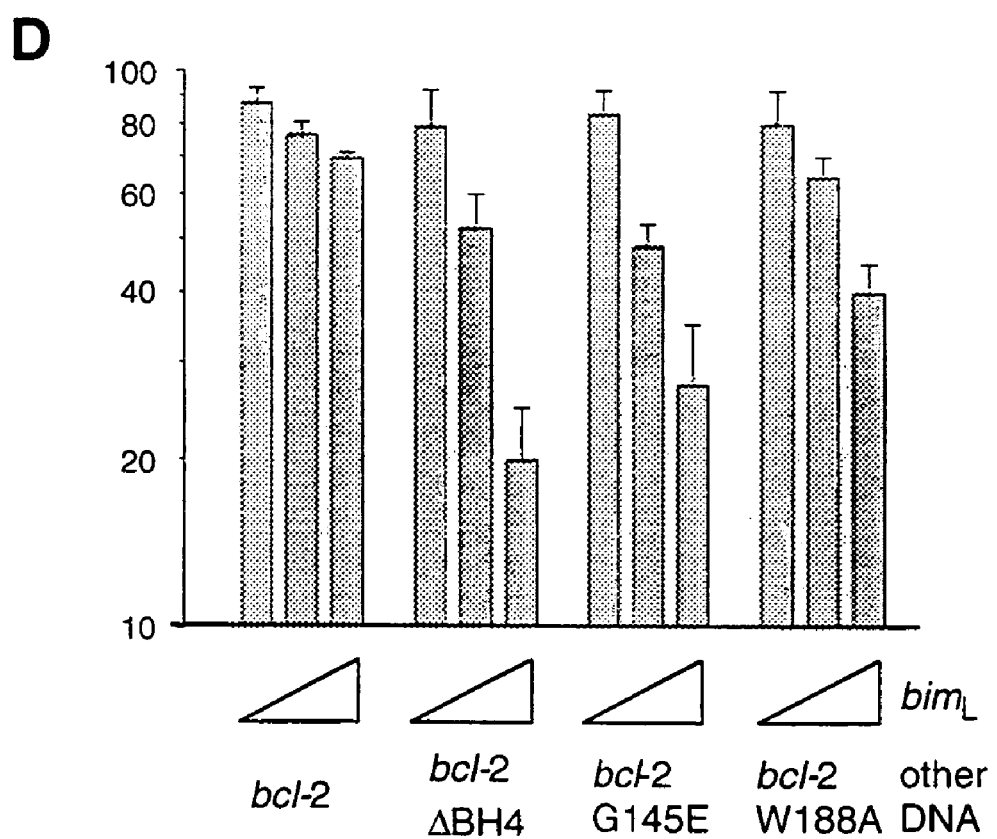

Other known 'BH3-only' proteins (Bik/Nbk, Bid and Hrk) provoke apoptosis when highly expressed (Boyd et al., 1995; Han et al., 1996; Wang et al., 1996; Inohara et al., 1997). We therefore tested whether Bim is cytotoxic by transiently transfecting 293T human embryonal kidney cells with a plasmid encoding EE-$Bim_L$. The viability of the transfected cells was determined subsequently by flow cytometric analysis of permeabilised cells stained with the anti-EE antibody and the DNA-intercalating dye propidium iodide (PI). Whereas almost all untransfected cells or those transfected with an empty vector remained viable after 24 hr, many of those expressing Bim (i.e., EE-antibody positive) contained sub-diploid DNA (FIG. 4A). Indeed, by three days, 90% of the cells expressing $Bim_L$ were dead (FIG. 4B).

The extent of cell death was proportional to the amount of bim DNA transfected (black bars, FIG. 4C).

The cells expressing Bim appeared to die by apoptosis, as assessed by cell morphology and the generation of sub-diploid DNA (FIG. 4A). As expected, the death process required activation of caspases, because co-expression of baculovirus p35, a competitive inhibitor of many types of caspases (Bump et al., 1995), antagonised Bim-induced cell death, whereas an inactive mutant p35 did not (FIG. 4C). Since crmA, a potent inhibitor of caspases 1 and 8 (ICE and FLICE) (Orth et al., 1996; Srinivasula et al., 1996) was not effective (FIG. 4C), these particular caspases do not appear to play a critical role.

Numerous failed attempts to generate lines that stably express Bim suggested that it is toxic to diverse cell types. Those repeatedly tested include haemopoietic lines (FDC-P1, CH1, Jurkat, SKW6 and B6.2.16BW2), fibroblastoid lines (Rat-1, NIH3T3 and L929) and an epithelial line (293). The cells were electroporated with a vector encoding antibiotic resistance and either EE- or FLAG-tagged $Bim_L$ and selected in antibiotic, but no line expressing Bim emerged. A vector encoding untagged Bim also failed to generate viable clones. We quantified the cytotoxicity of Bim by colony assays on transfected L929 fibroblasts. The EE-$Bim_L$ vector yielded only one fifth as many antibiotic-resistant colonies as the control vector, and when six of the EE-$Bim_L$-transfected, drug-resistant colonies were expanded, only one contained any Bim and the level was very low (Table 1 and data not shown). Thus, high levels of Bim suppress clonogenicity and appear incompatible with prolonged cell viability.

EXAMPLE 4

Bim Cytotoxicity can be Abrogated by Wild-Type Bcl-2 But not Inactive Mutants

Co-expression experiments established that Bcl-2 could block cell death induced by $Bim_L$ (FIG. 4D). In 293T cells transiently transfected with both the bcl-2 and $Bim_L$ plasmids, relatively few cells died, even with a high concentration of $Bim_L$ DNA (compare the 4th sample in FIG. 4C with the 3rd in FIG. 4D). The cytotoxicity of bim, however, could not be countered by mutant forms of bcl-2 rendered inactive by deletion of the BH4 homology region (ΔBH4) (Borner et al., 1994), or by a point mutation in its BH1 (G145E) or BH2 (W188A) region (Yin et al., 1994) (FIG. 4D). Thus, ability to antagonise Bim-induced cell death required a functional Bcl-2 molecule.

Figure 5:
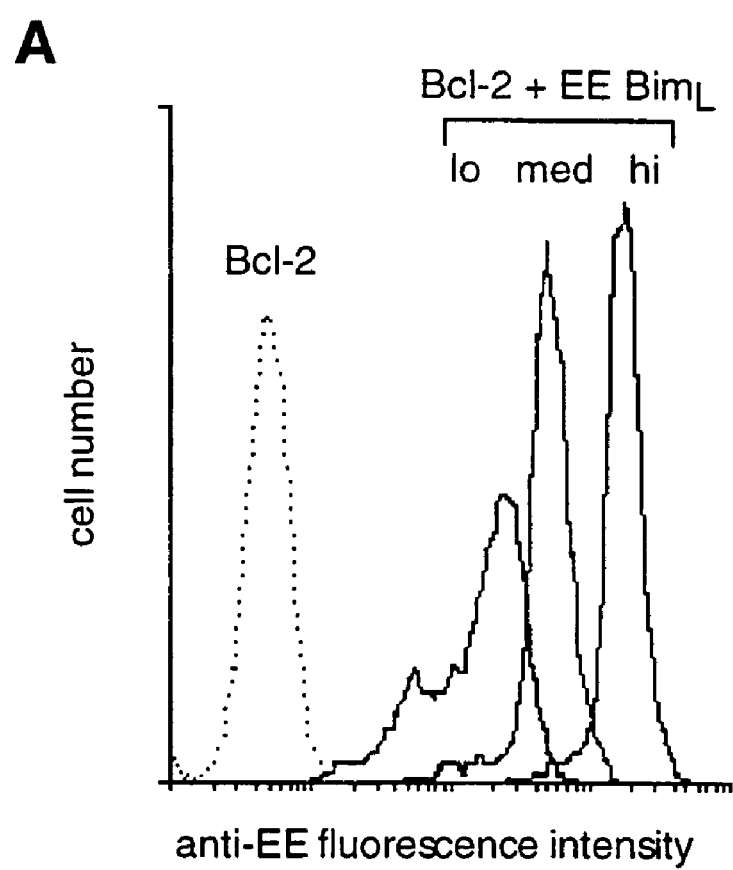
FIG. 5 is a graphical representation demonstrating that Bim antagonises the anti-apoptotic activity of Bcl-2 in a dose-dependent fashion. (A) Immunofluorescence staining of cloned FDC-P1 cell lines stably expressing Bcl-2 alone (dashed line) or co-expressing Bcl-2 and varying levels of EE-Bim$_L$ (solid lines). (B) Viability of these clones when cultured in the absence of IL-3 or after exposure to γ-irradiation (10 Gy). Cell viability was assessed by vital dye exclusion; data shown are means±SD of at least 3 experiments and are representative of results obtained with at least 3 independent lines of each genotype.
Figure 5:
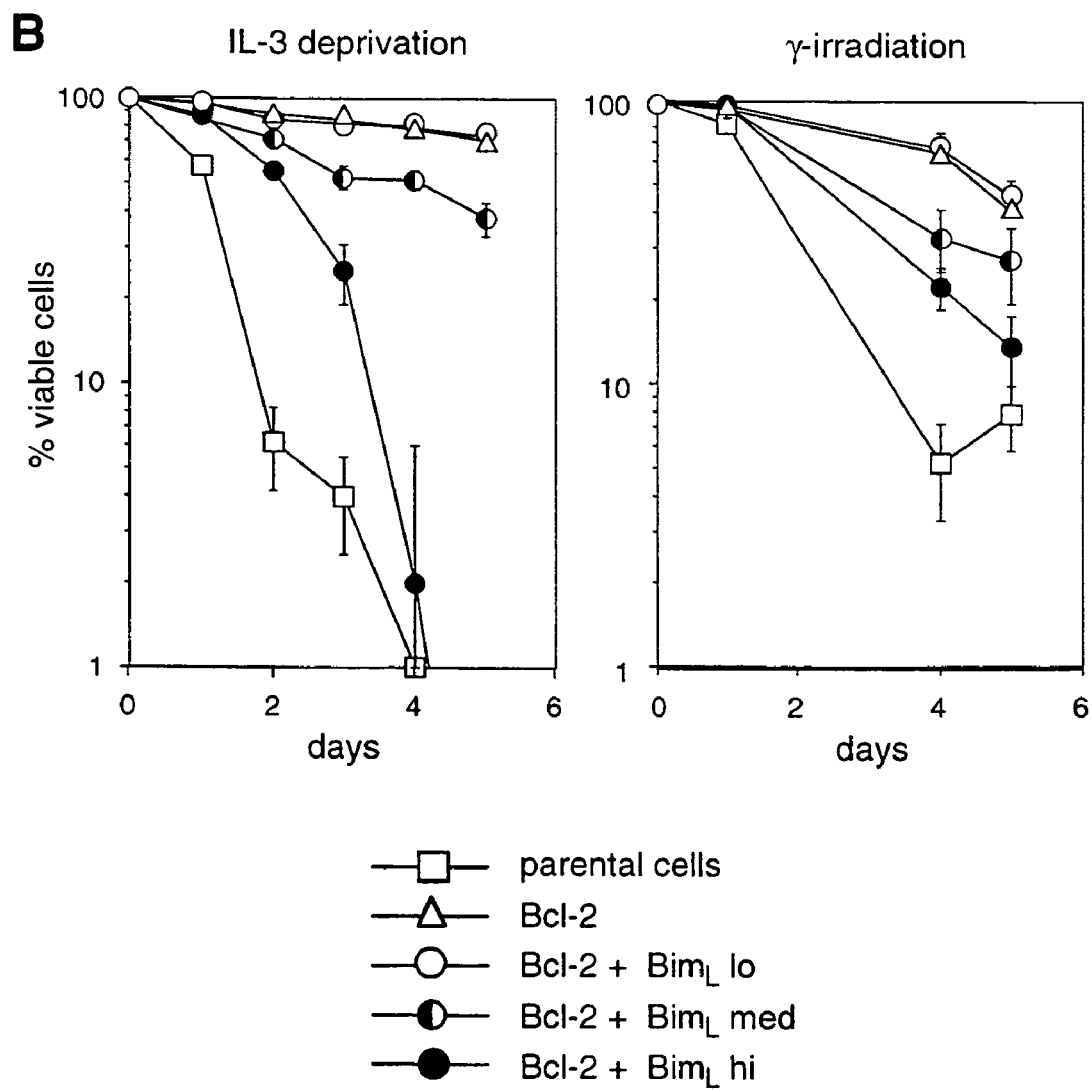

High levels of Bcl-2 allowed stable expression of $Bim_L$. Indeed, when L929 cells stably expressing Bcl-2 were transfected with the EE-$Bim_L$ vector, the frequency of antibiotic-resistant colonies approached that obtained with the control vector, and four of six colonies analysed contained moderate to high levels of Bim (Table 1 and data not shown). Similarly, using FDC-P1 clones expressing wt Bcl-2 (but not mutant Bcl-2), we could readily establish sub-clones expressing varying levels of $Bim_L$ (FIG. 5A). When grown in the presence of IL-3, all were indistinguishable in growth characteristics and morphology from the parental FDC-P1 cells or those bearing Bcl-2 alone. However, when deprived of IL-3 or irradiated, cells expressing Bcl-2 and a moderate or high level of Bim died more readily than those expressing Bcl-2 alone (FIG. 5B). Since each clone had the same level of Bcl-2 (not shown), their sensitivity to apoptosis presumably reflects the ratio of the pro-apoptotic Bim to the anti-apoptotic Bcl-2.

EXAMPLE 5

Figure 6:
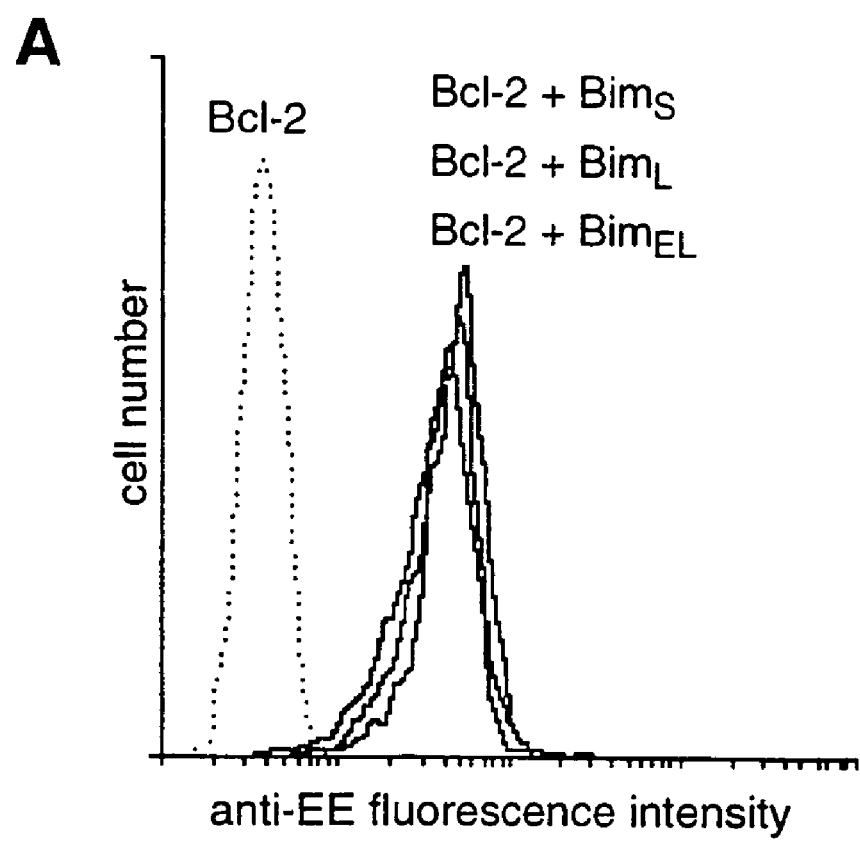
FIG. 6 is a graphical representation of a comparison of the activity of the three Bim isoforms. (A) Immunofluorescence staining of cloned FDC-P1 lines expressing Bcl-2 alone (dotted) or Bcl-2 plus EE-tagged Bim$_L$, Bim$_{EL}$ or Bim$_S$ (solid lines). (B) Association of EE-tagged Bim$_S$, Bim$_L$ and Bim$_{EL}$ with Bcl-2 demonstrated by anti-EE immunoblots of immunoprecipitates prepared with anti-human Bcl-2 monoclonal antibody from FDC-P1 cells expressing the indicated proteins. The 25 kD protein is non-specific. (C) Effect of Bim isoforms on viability of FDC-P1 cells expressing Bcl-2, after removal of growth factor or exposure to irradiation.
Figure 6:
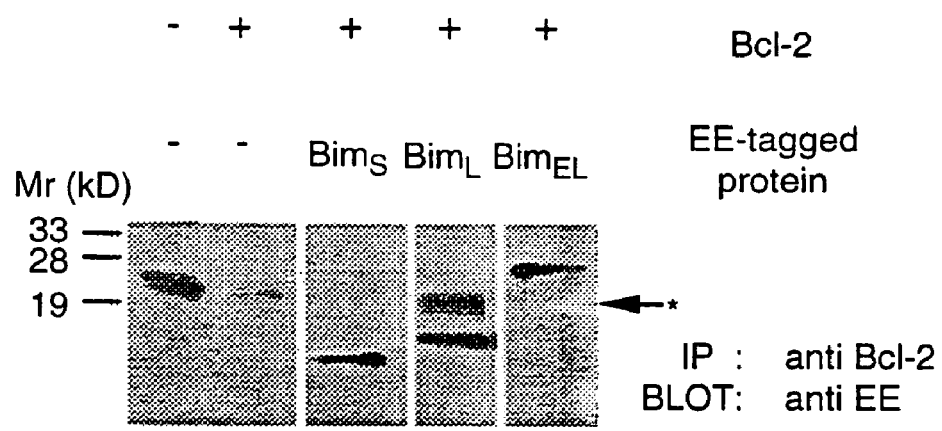
Figure 6:
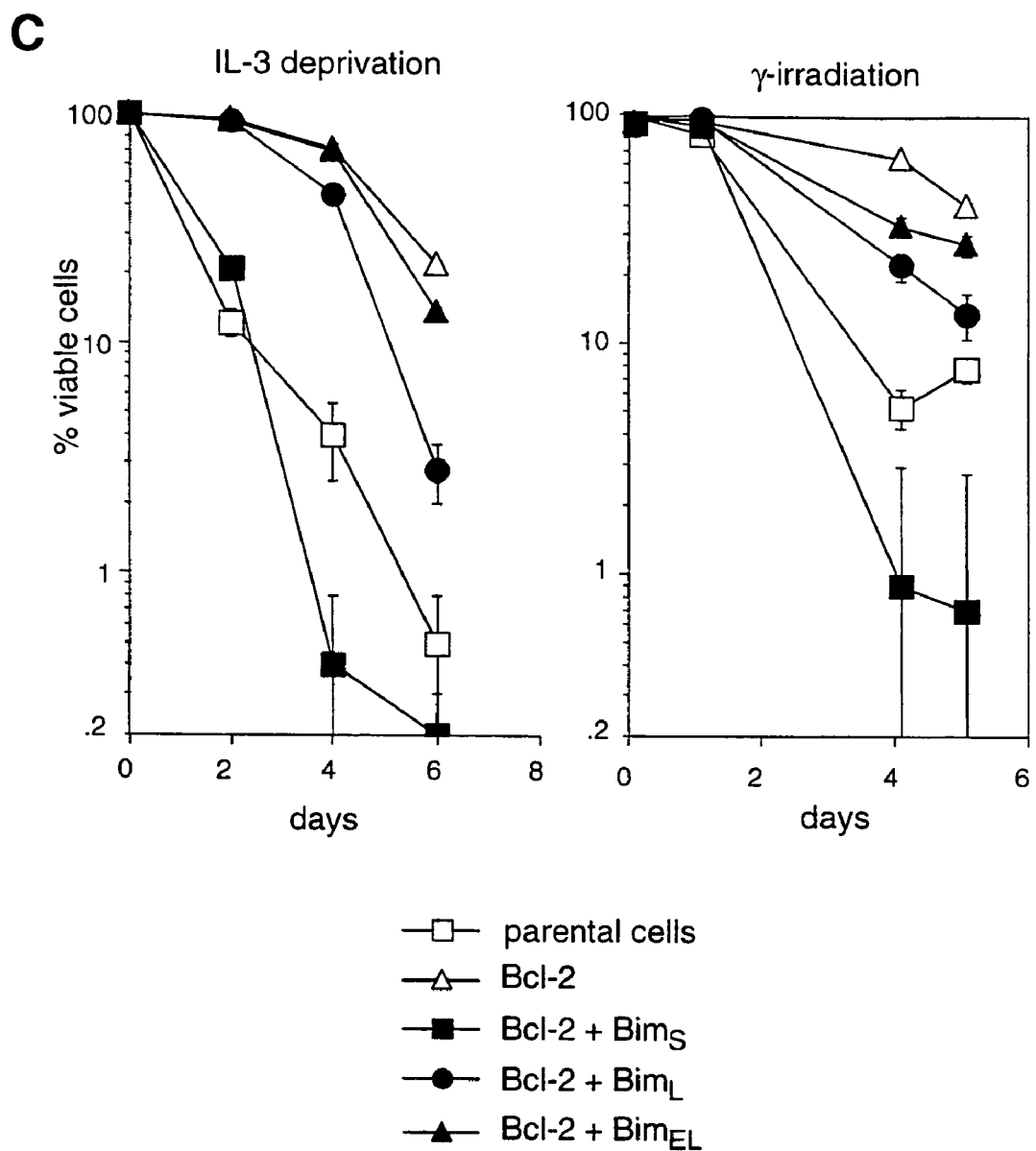

The Three Isoforms of Bin all Interact with Bcl-2 In Vivo But Vary in Cytotoxicity We next explored whether all isoforms of Bim were equivalent. An FDC-P1 clone expressing human Bcl-2 was transfected with vectors expressing $Bim_{EL}$, $Bim_L$ or $Bim_S$ and puromycin-resistant clones that expressed the same amount of each isoform were selected for further analysis (FIG. 6A). To test for association with Bcl-2, immunoprecipitates prepared from cell lysates using a monoclonal antibody specific for human Bcl-2 were fractionated electrophoretically and blotted with anti-EE antibody. Each of the Bim isoforms clearly bound to Bcl-2 (FIG. 6B). However, when the transfectants were deprived of IL-3 or subjected to γ-irradiation, it became evident that $Bim_S$ antagonised Bcl-2 more effectively than $Bim_L$ while $Bim_{EL}$ was the least potent (FIG. 6C). In addition, $Bim_S$ suppressed L929 colony formation more effectively than $Bim_L$ or $Bim_{EL}$. Thus, although all three Bim isoforms can bind to Bcl-2, they vary in cytotoxicity, $Bim_S$ being the most potent.

EXAMPLE 6

Bim Binds to and Antagonises Bcl-$x_L$ and Bcl-w But not Viral Bcl-2 Homologues

Figure 7:
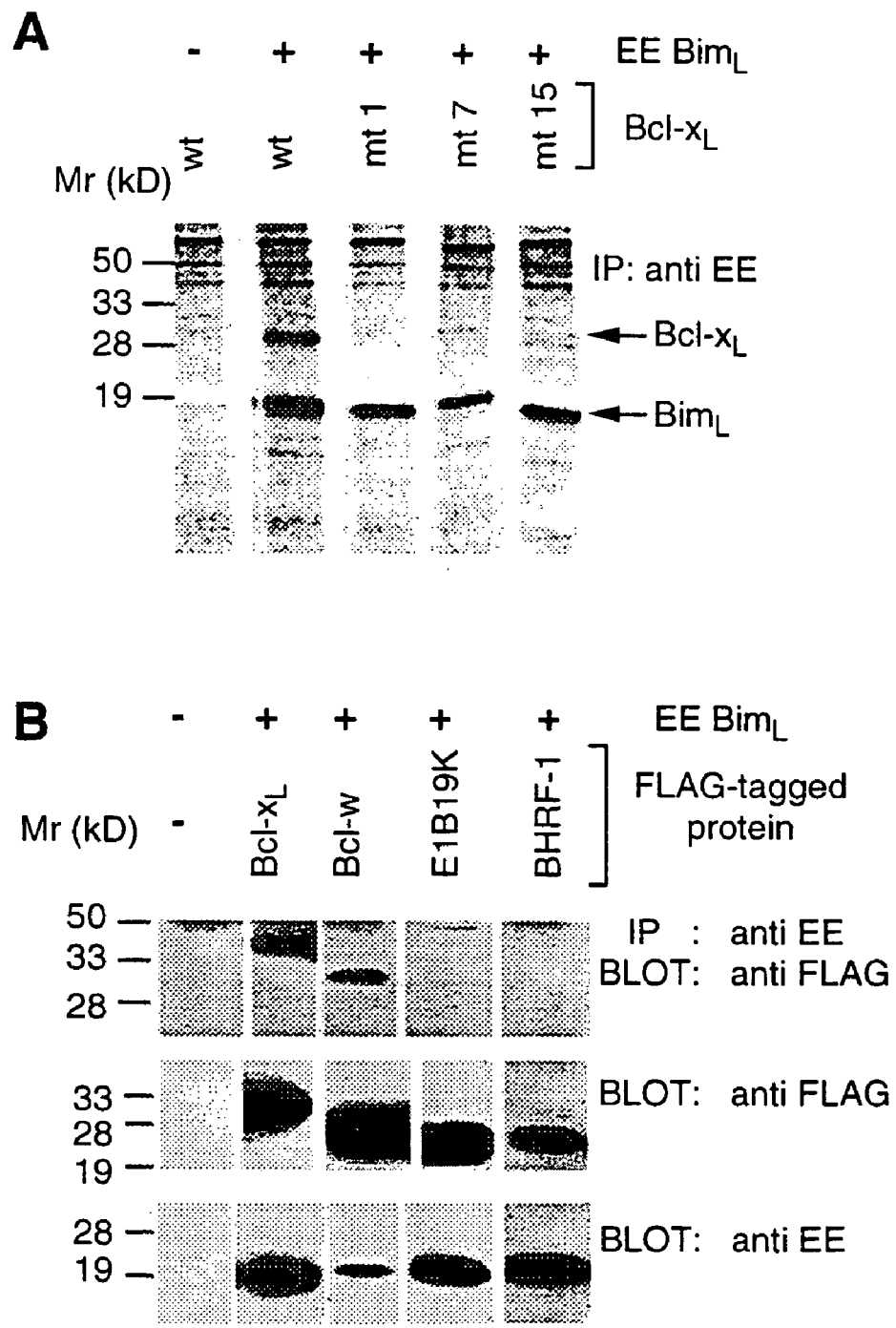
FIG. 7 is a graphical representation demonstrating that Bim binds to and antagonises Bcl-x$_L$ or Bcl-w but not E1B19K. (A) Lysates of $^{35}$S-labelled 293T cells transiently co-transfected with the plasmids encoding the indicated proteins were immunoprecipitated with anti-EE antibody, and the EE-Bim$_L$-containing complexes were fractionated by SDS-PAGE. (B) Lysates from parental 293T cells or 293T cells co-expressing EE-tagged Bim$_L$ and FLAG-tagged Bcl-x$_L$, Bcl-w or E1B19K were immunoblotted directly or after immunoprecipitation, as indicated. (C, D) 293T cells were transiently transfected with a vector control (unfilled bar) or with 0.1, 0.2 or 0.5/g of EE-Bim$_L$ plasmid, either alone (black bars) or together with 0.5 µg of plasmids encoding wt or mutant Bcl-x$_L$ (C); Bcl-w or E1B19K protein (D) (grey bars). The flow cytometric analysis was as described in the legend to FIG. 4. Data shown are means±SD of 3 or more independent experiments.
Figure 7:
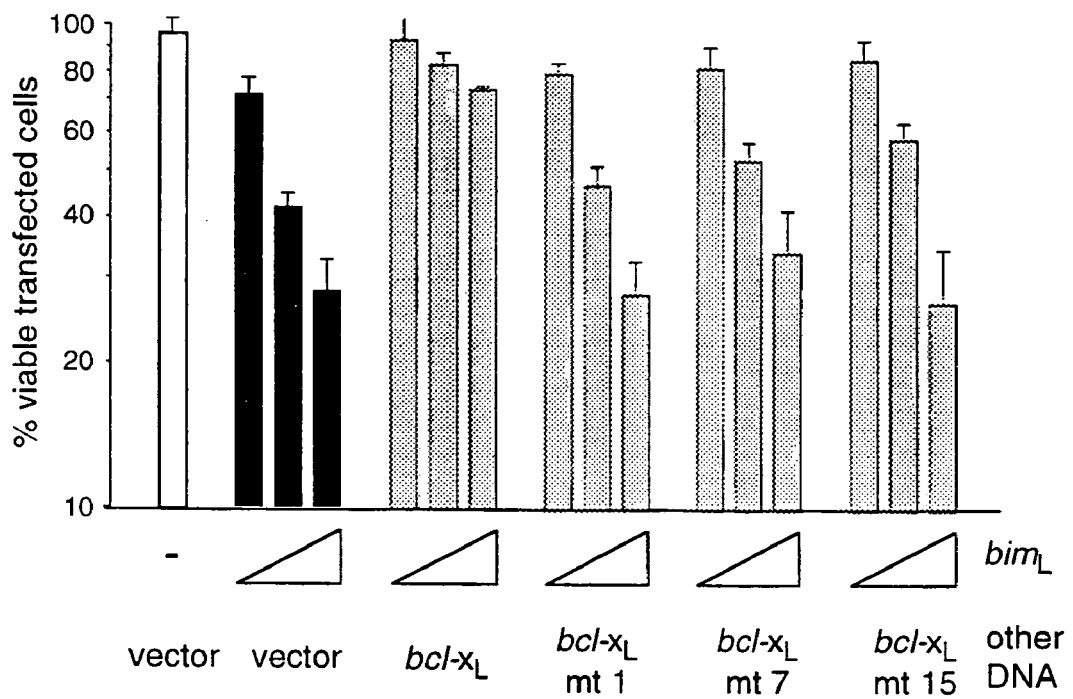
Figure 7:
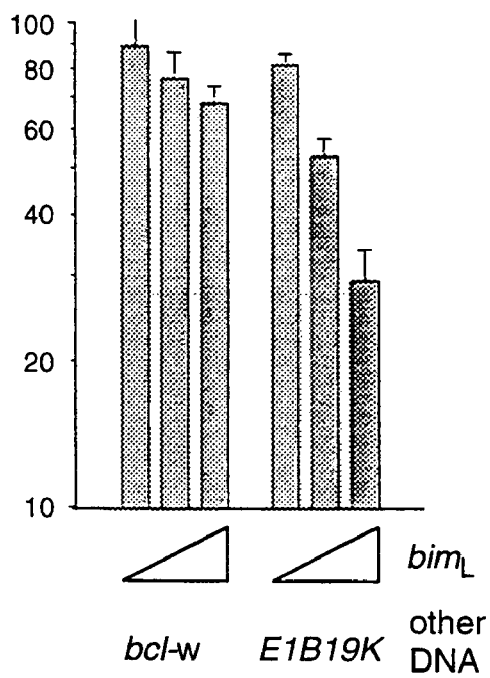
Figure 7:
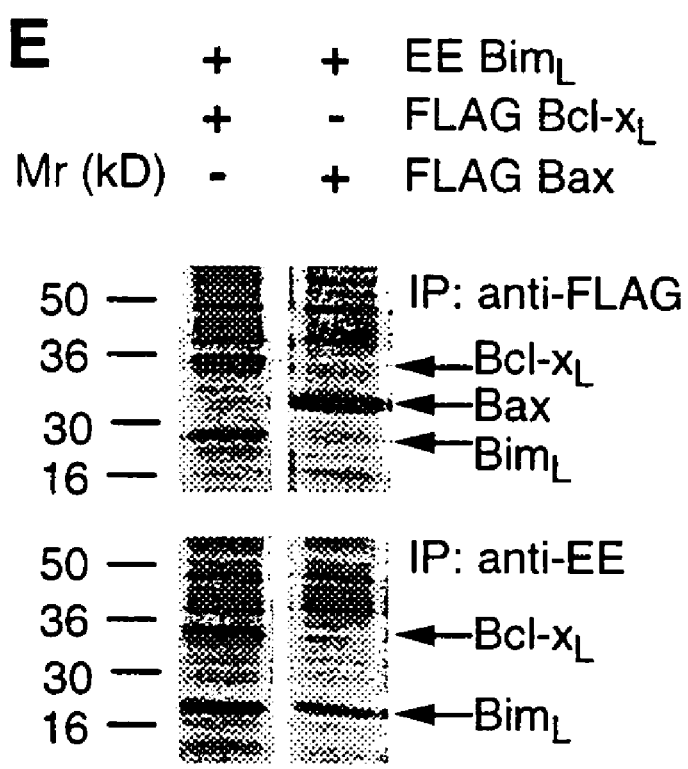

To determine whether Bim interacts with other members of the Bcl-2 family, we performed immunoprecipitation on lysates from 293T cells transiently co-transfected with the relevant vectors. No interaction with the pro-apoptotic Bax protein was observed, under conditions in which Bax:Bcl-$x_L$ association was readily detectable. Association of Bim with Bcl-$x_L$ or each of three point mutants was assessed in $^{35}$S-labelled 293T cells (FIG. 7A). Bim bound to wild-type Bcl-$x_L$ but not to a mutant (mt 7) that lacks pro-survival activity, nor to two mutants (mt 1 and mt 15) which retain significant anti-apoptotic activity but cannot bind to Bax (Cheng et al., 1996).

$Bim_L$ also bound strongly to the other cellular pro-survival regulator tested, Bcl-w (Gibson et al., 1996) (FIG. 7B). In marked contrast, $Bim_L$ did not bind to either of two virally encoded Bcl-2 homologues, the adenovirus E1B19K protein (FIG. 7B) and the Epstein-Barr virus BHRF-1 protein, even though both viral proteins bound to EE-Bax. Thus, not all mediators of cell survival associate with Bim.

Functional tests mirrored the binding properties of the various Bcl-2 homologues. When transiently co-expressed with Bim in 293T cells, Bcl-$x_L$ and Bcl-w countered Bim toxicity as effectively as Bcl-2 (FIGS. 7C and 7D). In contrast, little inhibition was observed with comparable levels of the mutant Bcl-$x_L$ proteins (FIG. 7C) or the adenovirus E1B19K protein (FIG. 7D). These data suggest that Bcl-2-like inhibitors of apoptosis must bind to Bim to inhibit its action.

EXAMPLE 7

Figure 8:
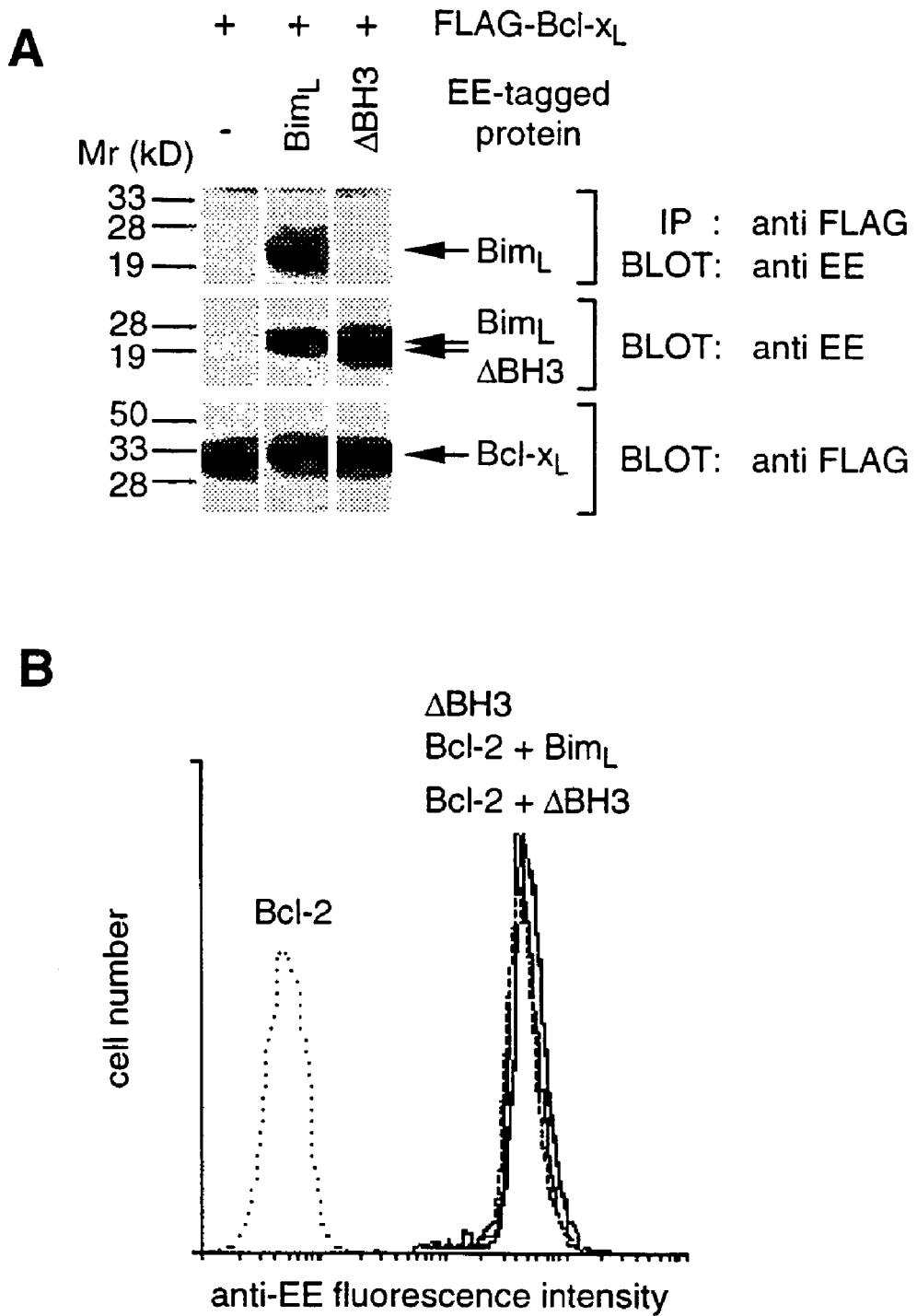
FIG. 8 is a graphical representation demonstrating that the BH3 homology region of Bim is required for binding to and inhibiting Bcl-2. (A) Immunofluorescence staining of cloned FDC-P1 lines expressing Bcl-2 alone (dotted) or with EE-Bim$_L$ or EE-Bim ΔBH3 (solid line), and of EE-Bim ΔBH3 in the parental FDC-P1 cells (broken line). (B) Immunoblot showing that Bcl-2 associates with wild-type Bim$_L$ but not the ≠BH3 mutant. (C) Viability of FDC-P1 clones expressing the indicated proteins (see A) was assessed by vital dye exclusion. Data shown are means±SD of at least 3 experiments and are representative of results obtained with at least 3 independent lines of each genotype.
Figure 8:
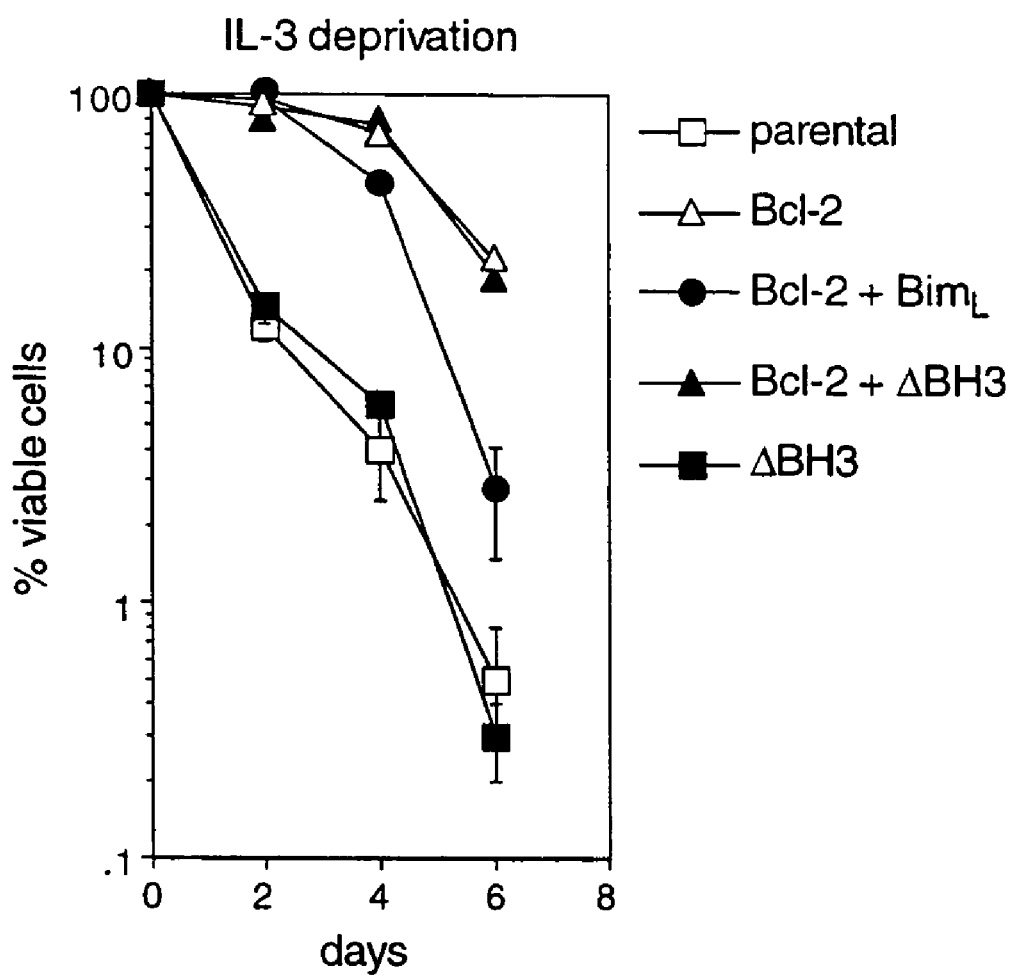

The BH3 Region is Essential for Interaction of Bim with Bcl-2 and for Most of its Ability to Promote Apoptosis Since the BH3 region of several death-promoting proteins is essential for their activity (see Introduction), we tested a $Bim_L$ mutant lacking the BH3 region. In transfected cells the mutant protein (ΔBH3) was readily detected by immunofluorescence and Western blotting (FIG. 8A), establishing that BH3 is not essential for stability of the polypeptide. Unlike wt Bim, however, the ΔBH3 mutant did not bind to Bcl-2 in vivo (FIG. 8B).

In some biological assays, the ΔBH3 mutant of Bim appeared inert. In contrast to wt Bim, it was easy to establish lines expressing Bim$_L$ ΔBH3 from FDC-P1 (FIG. 8A) or L929 cells (Table 1). Moreover, Bim$_L$ ΔBH3 did not impair the viability of the FDC-P1 cells in either the presence or absence of Bcl-2 (FIG. 8C). Finally, 293T cells transiently transfected with Bim$_L$ ΔBH3 exhibited high viability (not shown). These results indicate that the BH3 region is critical for Bim to promote apoptosis and suggest that Bcl-2 blocks this activity of Bim by binding to that domain. Importantly, however, Bim$_L$ ΔBH3 was not completely inactive. In the L929 clonogenicity assay, it still markedly suppressed colony formation (Table 1). Thus, regions of Bim other than BH3 may promote apoptosis or interfere with clonogenicity in another way, such as by blocking cell growth.

EXAMPLE 8

Expression Library Screening and Isolation of Mouse and Human Bim cDNAs

Polyadenylated RNA prepared from p53$^{-/-}$ K052DA20 T lymphoma (Strasser et al., 1994) cells subjected to γ-irradiation (10 Gy) was reverse-transcribed, using a combination of oligo dT and random oligonucleotide primers, and ligated to EcoRI adaptors, using standard procedures. The cDNA was then ligated with Eco RI+Xho I-digested λ ZapExpress (Stratagene) arms and packaged in vitro according to the supplier's instructions. The resulting expression library was screened using radiolabelled Bcl-2 lacking the hydrophobic membrane localisation region. To prepare this probe, cDNA encoding amino acids 1 to 210 of human Bcl-2 was subcloned into the vector pARΔR1 (Blanar and Rutter, 1992), and recombinant protein (FLAG-HMK-Bcl-2ÆC30) produced in IPTG-induced E. coli BL21pLysS (DE3) cells (Novagen) was purified on anti-FLAG M2 affinity gel (IBI Kodak) and then kinased in vitro using bovine heart muscle kinase (Sigma) and [γ-$^{32}$P]ATP (Amersham) (Blanar and Rutter, 1992). ~10$^6$ plaques were screened with ~10$^7$ cpm of the radiolabelled probe using the protocol of Blanar and Rutter (Blanar and Rutter, 1992). To reduce non-specific background, the filters were pre-incubated with lysates from induced parental BL21pLysS (DE3) cells and excess unlabelled ATP. Plaques that were positive on duplicate lifts were picked for two rounds of further screening. Positive clonas were excised in vivo by coinfection with filamentous ExAssist (Stratagene) helper phage and sequenced by automated sequencing (ABI Perkin Elmer). The human bim cDNA clone was isolated by screening human embryo and liver A cDNA libraries (Stratagene) with an ~800 bp mouse bim cDNA probe, using standard techniques. The cDNAs were fully sequenced, analysed using Wisconsin GCG or DNASTAR software and compared with sequences in the Genbank (including dBEST) and EMBL databases using the BLAST algorithm (Altschul et al., 1990).

EXAMPLE 9

Expression Constructs and Site-Directed Mutagenesis cDNAs were cloned into the expression vectors pEF PGKpuro (Huang et al., 1997) or pEF PGKhygro (Huang et al., 1997), or derivatives thereof incorporating N-terminal FLAG (DYKDDDDK) SEQ ID NO: 11 (Hopp et al., 1988) or EE (EYMPME) SEQ ID NO: 12 (Grussenmeyer et al., 1985) epitope tags. The bimÆBH3 mutation was generated by deleting the DNA encoding amino acids 94 to 100 (LRRIGDE) SEQ ID NO: 13 and replacing this with DNA corresponding to a Hind III site (encoding AL). Mutations in bcl-2 (ΔBH4, G145E, W188A) (O'Reilly et al., 1996; Huang et al., 1997) were generated by polymerase chain reaction via splice overlap extension (Horton et al., 1993) using the proof-reading Pfu DNA polymerase (Stratagene) (oligonucleotides used are detailed in SEQ ID NO: 14–26). The sequences of derived clones were verified by automated sequencing prior to function analysis.

EXAMPLE 10

Cell Culture and Transfection

Cell lines used were: mouse IL-3-dependent promyelocytic line FDC-P1; mouse T hybridoma B6.2.16BW2; mouse B lymphoma lines CH1 and WEHI 231; mouse pre-B lymphoma line WEHI 415 (derived from a tumour which arose in an Eμ-myc transgenic mouse); human B lymphoblastoid line SKW6; human T lymphoma line Jurkat; mouse T lymphoma lines WEHI 703, WEHI 707 (both derived from tumours which arose in Eμ-NRas transgenic mice) and WEHI 7.1; rat fibroblastoid line Rat-1; mouse fibroblastoid line NIH 3T3; mouse fibroblastoid line L929 subline LM(-TK); human embryonal kidney cell line 293 (ATCC CRL-1573) and SV40-transformed 293 cells, 293T (see Lithgow et al., 1994; Strasser et al., 1994; Strasser et al., 1995; Huang et al., 1997). The procedures for culture and stable transfection are described elsewhere (Huang et al., 1997). Drug-resistant transfectants were cloned using the cell deposition unit of a FACStarPlus (Becton Dickinson) and clones expressing high levels of the protein of interest were identified by immunofluorescence staining of fixed and permeabilised cells followed by flow cytometric analysis.

EXAMPLE 11

Cell Death Assays

Cytokine deprivation and exposure to ionising radiation were the principal cell death assays used to assess the sensitivity of FDC-P1 cells stably transfected with the various expression vectors. Cells were cultured in medium lacking cytokine or (in complete medium) after exposure to 10 Gy γ-radiation (provided by a $^{60}$Co source at a rate of 3 Gy/min) and their viability determined over several days by vital dye (0.4% eosin) exclusion, as assessed by visual inspection in a hemocytometer, or by flow cytometric analysis of cells that excluded propidium iodide (5 μg/ml; Sigma) (Nicoletti et al., 1991).

Cell death assays in 293T cells were performed after transient transfection of ~5×10$^5$ cells using 6 μl of Lipofectamine® (Gibco BRL) and a total of 1 μg DNA in 2 ml of medium in 6 cm dishes; for co-transfections, bim plasmid (0.1, 0.2, 0.5 μg) was co-transfected with 0.5 μg of the other recombinant (eg bcl-2) plasmid and (0.4, 0.2, 0 μg) of empty vector. Forty-eight hours after transfection, the cells were harvested, fixed for 5 min in 80% methanol, permeabilised with 0.3% saponin (which was included in all the subsequent steps), and stained with 1 μg/ml anti-EE monoclonal antibody (BabCO), followed by fluorescein isothiocyanate (FITC)-conjugated goat anti-mouse IgG (1 µg/ml; Southern Biotechnology) as the secondary agent and by 69 µM propidium iodide in 38 mM sodium citrate pH 7.4 (Crissman et al., 1990). Analysis was performed on a FACScan (Becton Dickinson), the proportion of dead cells being taken to be the proportion of EE-positive cells with less than 2C DNA content (Nicoletti et al., 1991).

L929 fibroblast colony assays were performed in triplicate by scoring the numbers of colonies in 10 cm dishes grown for 14–18 days with appropriate antibiotic selection. These cells had previously been split (1:3) from ~$10^6$ cells which had been transfected in 6 cm dishes 2 days earlier with 1 µg total DNA and 12 µl of Lipofectamine®.

EXAMPLE 12

Immunofluorescence, Immunoprecipitation and Immunoblotting

Immunofluorescence staining of cytoplasmic proteins with the monoclonal antibodies Bcl-2–100 (mouse anti-human Bcl-2; [Pezzella et al., 1990]) or mouse anti-EE (BabCO) followed by FITC-conjugated goat anti-mouse IgG (Southern Biotechnology) was performed as previously described (Huang et al., 1997). Cells were analysed in the FACScan II (Becton Dickinson) after exclusion of dead cells on the basis of their forward and side scatter characteristics.

To investigate the subcellular localisation of EE-tagged $Bim_L$, transfected L929 fibroblasts grown in chamber slides (Erie Scientific Company, New Hampshire) were fixed in 4% paraformaldehyde for 10 min at room temperature and the slides were then allowed to dry and stored at −20° C. Prior to analysis by confocal microscopy, the cells were rehydrated by dipping the slides in water and then permeabilised for 15 minutes at room temperature in 0.5% Triton-X 100 in PBS. EE-$Bim_L$ was detected by incubating for the cells with anti-EE monoclonal antibody for 30 minutes, washing several times in PBS containing 2% foetal calf serum and 0.05% Tween-20, and then incubating for 30 minutes with goat anti-mouse IgG conjugated to lissamine-rhodamine (Jackson Immunoresearch), all steps being performed at room temperature. Human Bcl-2 was detected similarly, using hamster anti-human Bcl-2 (6C8) (Veis et al., 1993) followed by FITC-conjugated mouse anti-hamster IgG. Untransfected cells served as negative controls. Samples were analysed using a Leica confocal laser scanning microscope (Leica Lasertechnik).

To test for protein—protein interactions in vivo, immunoblotting was performed on stably transfected FDC-P1 cells or transiently transfected 293T cells as described previously (Huang et al., 1997). Briefly, lysates prepared from $10^5$–$10^6$ cells were incubated with ~5 µg antibody (anti-human Bcl-2, anti-FLAG M2 (IBI Kodak), or anti-EE monoclonal antibody), followed by protein G Sepharose (Pharmacia), and then pelleted, washed, fractionated by SDS-PAGE and transferred to nitrocellulose membranes by electroblotting. The filters were incubated with mouse anti-human Bcl-2, anti-FLAG or anti-EE antibodies followed by affinity-purified rabbit anti-mouse IgG; bound antibodies were detected with $^{125}$I-labelled staphylococcal protein A. In some experiments, the cells were metabolically labelled with 100–200 µCi/ml of $^{35}$S-methionine (NEG-072 from NEN) and equivalent TCA-precipitable counts (5×$10^7$ cpm) were used for each immunoprecipitation.

EXAMPLE 13

Antibody Production

Immunization

Wistar rats were immunized by injection of 100 µg of purified GST (glutathione-5-transferase)-$Bim_L$ fusion protein, purified on a glutathione sepharose affinity matrix (Pharmacia, Uppsala, Sweden). For the first immunization the protein was dissolved in complete Freund's adjuvant (Difco, Michigan, USA) and injected subcutaneously. Two subsequent boosts of the immunogen resuspended in incomplete Freund's adjuvant (Difco) were injected subcutaneously 3 and 6 weeks after the initial injection. A final boost was given four weeks later, i.e. three days prior to fusion.

Cell Fusion and Hybridoma Culture

Rat spleen cells were fused according to published procedures (Galfre et al., 1977) with Sp2/0 mouse myeloma cells (Shulman et al., 1978) at a ratio of 2:1 to 4:1, using polyethylene glycol 1500 (Boehringer Mannheim, Mannheim, Germany). After fusion, the cells were resuspended in Dulbecco's modified Eagle's medium (DMEM) containing 15% FCS (MultiSer, Trace Bioscience, Australia, batch #31104149), 5 mM hypoxanthine, 0.02 mM aminopterin and 0.8 mM thymidine (HAT; Boehringer), with IL-6 and plated into flat bottom 96-well plates (Falcon, Becton Dickinson, N.J., USA). The source of IL-6 was supernatant from X63/0 hybridoma cells stably transfected with an IL-6 expression construct (Karasuyama et al., 1988). The titre of IL-6 in the supernatant was determined by stimulation of the IL-6-dependent cell line 7TD1 (22). IL-6 was utilized in the fusion medium at a concentration which permitted maximal proliferation of 7TD1 cells. Fresh tissue culture medium was added to the hybridoma cells on day 7 after fusion and supernatants were harvested for analysis on days 9–11 depending on the rate of colony growth. Stable antibody-producing clones were established by two sequential steps of single cell cloning.

Tissue Culture and Cell Lines

The IL-3-dependent mouse promyelomonocytic cell line FDC-P1 (Dexter et al., 1980) was cultured in the high glucose version of Dulbecco's modified Eagle's medium (DMEM) supplemented with 10% fetal calf serum (FCS), 50 µM 2-mercaptoethanol, 13 µM folic acid, 100 µM L-asparagine and 1000 U/mL IL-3. The source of IL-3 was supernatant from X63/0 hybridoma cells stably transfected with an IL-3 expression construct (Karasuyama and Melchers, 1988). Derivative clones of FDC-P1 cells transfected with a human bcl-2 expression construct, FDC-P1/Bcl-2 (Huang et al., 1997), or a human bcl-2 expression construct and a Glu—Glu (EE) epitope-tagged mouse $Bim_L$ expression construct, FDC-P1/Bcl-2/EE-$Bim_L$ (O'Connor et al., 1998) have been described previously.

Expression of Bim and Bcl-2 was verified by cytoplasmic immunofluorescent staining (see below and (Strasser et al., 1995)) using 1 µg/mL mouse anti-human Bcl-2 monoclonal antibody Bcl-2–100 (17) or 2 µg/mL mouse anti-EE monoclonal antibody (anti-EE) (BabCO, Richmond, Calif., USA) and as the secondary reagent 5 µg/mL fluorescein isothiocyanate (FITC)-conjugated goat anti-mouse IgG antibodies (Southern Biotechnology, Birmingham, Ala., USA).

Hybridoma Screening

A 1:1 mixture of FDC-P1/Bcl-2 and FDC-P1/Bcl-2/EE $Bim_L$ cells was prepared and fixed in 1% paraformaldehyde for 15 min at room temperature. Cells were washed twice in balanced salt solution containing 2% FCS and 10 mM sodium azide (wash buffer) and $5\times10^5$ cells (in 50 μL wash buffer) were dispensed into each well of 96-well soft plastic U-bottomed plates (Dynex, Va., USA). The cell pellets were resuspended in 100 μL of day 10–11 hybridoma supernatant with 50 μL of a 1% saponin solution (for cell permeabilization) in wash buffer, vortexed and incubated for 30 min on ice. Plates were washed twice by centrifugation (3 min at 1500 rpm in a Heraeus Sepatech Megafuge 1.0R) in wash buffer containing 0.03% saponin and resuspended in 100 μL wash buffer containing 0.3% saponin and 10 μg/mL FITC-coupled goat anti-rat IgG (heavy and light chain-reactive) antibodies (Southern Biotechnology) and incubated for 30 min on ice. Finally, cells were washed twice in wash buffer containing 0.03% saponin and resuspended in wash buffer. To confirm $Bim_L$ expression a control sample was stained with mouse anti-EE antibodies (BabCO) and detected with 5 μg/mL goat anti-mouse IgG antibodies conjugated to FITC (Southern Biotechnology). Cell staining was analyzed in a FACScan (Becton Dickinson, Mountain View, Calif., USA) after exclusion of dead cells on the basis of their forward and side light scatter characteristics. Fluorescence histograms were only printed from the positive samples. To speed up sample processing to a rate of 250 to 300 samples per hour, only 500 cells were analyzed. This allowed one person to screen 2000 hybridoma cultures over two days.

Expression Constructs and Protein Purification

The vectors pEF Bcl-2 pGKpuro, pEF FLAG $Bim_L$ and pEF $EEBim_L$ pGKhygro have been described before (Huang et al., 1997; O'Connor et al., 1998). Full length mouse $bim_L$ cDNA was cloned into pGEX (128/128) (Blanar and Rutter, 1992) to allow production of GST-FLAG-$Bim_L$ protein in the bacterial strain JM109. The recombinant protein was purified from IPTG-induced (Sigma, St Louis, Mo., USA) bacterial cultures using binding to glutathione-sepharose 4B and elution with reduced glutathione (Pharmacia) (Smith and Johnson, 1988). The recombinant protein was resuspended in PBS pH 7.

Western Blotting

FDC-P1/Bcl-2 and FDC-P1/Bcl-2/EE $Bim_L$ cells were harvested in lysis buffer (20 mM Tris-HCl, pH 8.0, 125 mM NaCl, 1 mM EGTA, 1% Triton X-100, 10% glycerol, 0.5 μg/mL Pefabloc, 1 μg/mL of each: leupeptin, aprotinin, soybean trypsin inhibitor and pepstatin, 5 mM NaF and 2 mM $Na_3VO_4$; all reagents from Sigma or Boehringer Mannheim). Lysates from $10^6$ cells were boiled in gel running buffer (0.25 M Tris-HCl pH 6.8, 1% SDS, 20% glycerol, 5% 2-mercaptoethanol, 0.02% bromophenol blue), resolved on 4–20% polyacrylamide gels (Novex, San Diego, Calif., USA) and transferred to nitrocellulose membranes by electroblotting. After incubation overnight at 4° C. in 5% skimmed milk, 1% casein and 0.05% Tween-20 to prevent non-specific binding, the filters were incubated (1 hr at room temperature) with the rat anti-Bim monoclonal antibodies diluted 1:1 with blotting solution, followed by affinity-purified HRP-conjugated goat anti-rat IgG antibodies (Southern Biotechnology). Proteins were visualized by enhanced chemiluminescence (Amersham, Amersham, UK). Metabolic labelling of cells with $^{35}$S-methionine and immunoprecipitation 293T human kidney embryonal cells were transiently transfected with Bim expression constructs, as described (O'Connor et al., 1998). After 48 hours the cells were labeled overnight with 100 μCi/mL $^{35}$S-methionine (Du Pont, NEN Research Products, Boston, Mass., USA). Cell lysates were prepared in lysis buffer and quantified by TCA (trichloroacetic acid) precipitation. Equivalent TCA precipitable counts ($10^7$ cpm) were used for each immunoprecipitation (O'Connor et al., 1998), and analyzed on 4–20% gradient polyacrylamide gels (Novex). As a control anti-FLAG M2 (IBI Kodak, New Haven, Conn., USA) and anti-mouse CD4 antibodies (clone H129.19.6.8) were used.

Results

Figure 10:
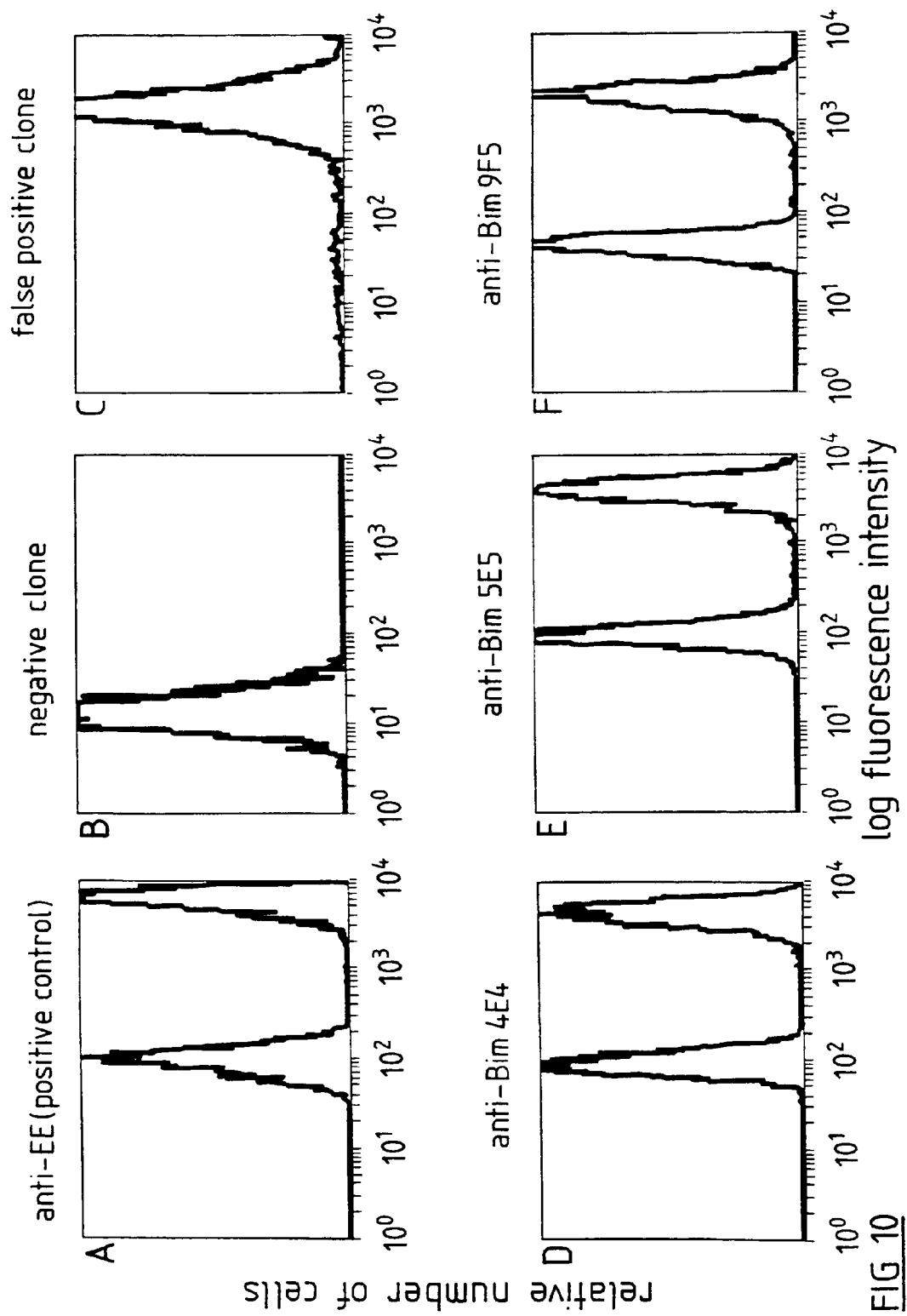
FIG. 10 is a graphical representation of the detection of Bim Specific Antibodies. Stably transfected FDC-P1/Bcl-2 and FDC-P1/Bcl-2/EE-Bim cells were mixed 1:1, fixed, permeabilized and stained with anti-EE antibodies (A, positive control) or with hybridoma supernatants from the fusion (B–F). (B) shows a typical negative clone, (C) an antibody that is not specific to Bim but recognizes an epitope that is present in both FDC-P1/Bcl-2 and FDC-P1/Bcl-2/EE-Bim cells, and D–F show staining by the anti-Bim antibodies 4E4 (D), 5E5 (E) and 9F5 (F). Staining was visualized by either FITC-conjugated goat anti-mouse IgG antibodies (A) or FITC-conjugated goat anti-rat IgG antibodies (B–F), and analyzed by flow cytometry. Supernatants with anti-Bim reactivity (D–F) produced a double peak: background staining of the FDC-P1/Bcl-2 cells (lower intensity peak) and specific Bim staining of the FDC-P1/Bcl-2/EE-Bim cells (higher intensity peak).

Clones expressing high levels of Bcl-2 and EE-$Bim_L$ were selected by continuous growth in the presence of both drugs and by immunofluorescent staining with monoclonal antibodies specific to Bcl-2 or the EE epitope tag (FIG. 10A).

Rats were immunized with recombinant GST-Bim fusion protein. Hybridoma screening was performed 10–11 days after the fusion. The immunogen was tagged differently from the protein used for screening to avoid isolation of hybridomas producing tag-specific antibodies. A 1:1 ratio of FDC-P1/Bcl-2 and FDC-P1/Bcl-2/EE-$Bim_L$ cells were fixed, permeabilized with saponin and used to screen hybridoma supernatants. Those culture wells containing antibodies to Bim produced a double fluorescence peak when analyzed by flow cytometry (FIGS. 10D, E, F). The lower intensity peak represents background staining of FDC-P1/Bcl-2 cells. The higher fluorescence intensity peak is the result of specific Bim staining (FIG. 10A). Culture supernatants with no Bim reactivity showed only a single peak of low fluorescence intensity (FIG. 10B). Antibodies which were not specific to Bim but bound to some unknown epitope present in both FDC-P1/Bcl-2 and FDC-P1/Bcl-2/EE-$Bim_L$ cells produced a single peak with high fluorescence intensity (FIG. 10C). From the initial screen 18 potentially Bim reactive clones were expanded and subcloned. Three monoclonal antibodies were obtained, 4E4, 5E5 and 9F5, that stained Bim with high sensitivity and specificity (FIG. 10D–F).

Epitope mapping of monoclonal antibodies is possible with the technique described above, by using cell lines transfected with expression constructs encoding modified versions of the protein of interest. In the case of Bim we used FDC-P1/Bcl-2 lines that co-express different isoforms or mutants of Bim and found that the monoclonal antibodies detected only $Bim_L$.

Figure 11:
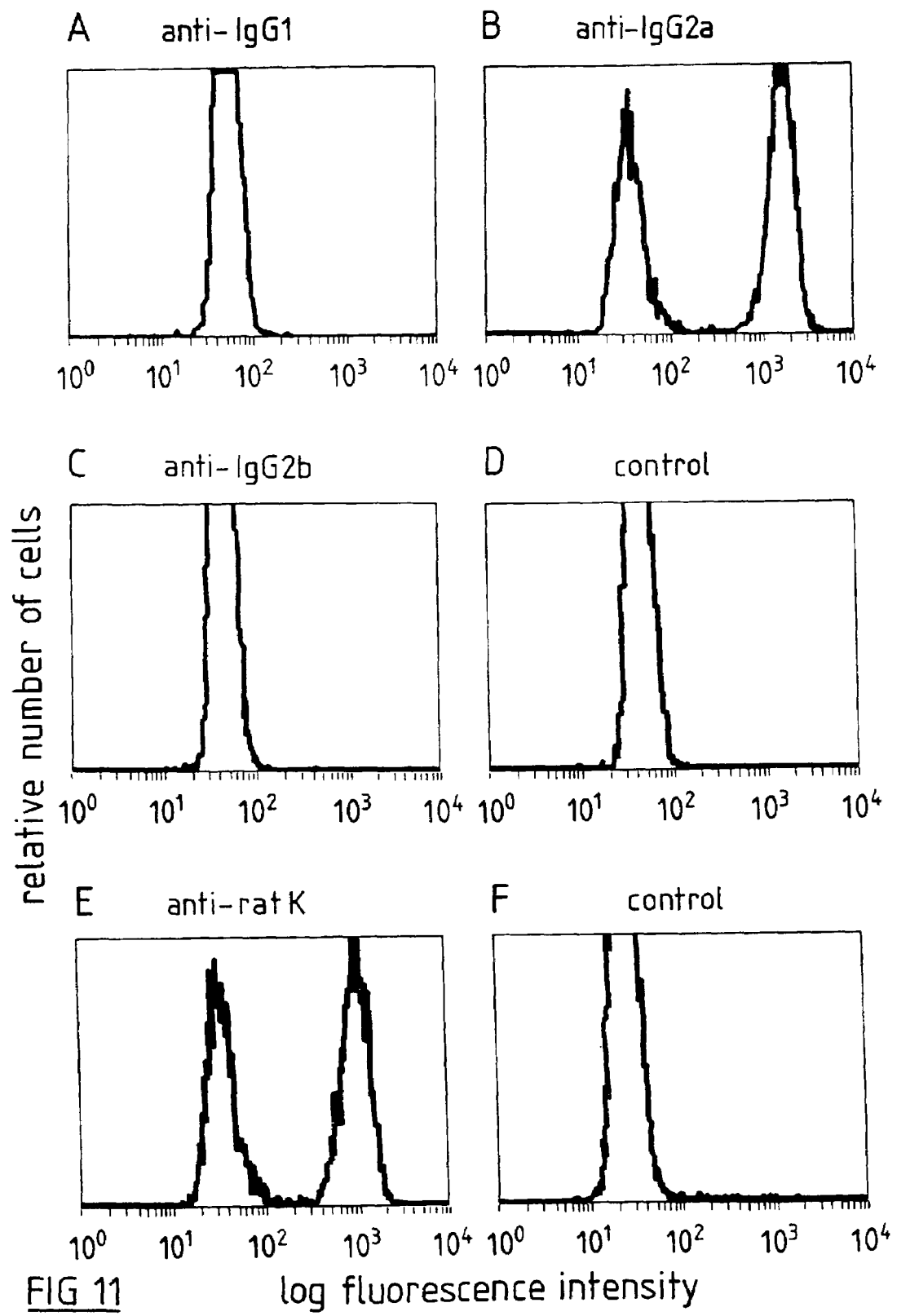
FIG. 11 is a graphical representation of the determination of the Ig isotypes of the Bim-reactive monoclonal antibodies. A 1:1 mixture of stably transfected FDC-P1/Bcl-2 and FDC-P1/Bcl-2/EE-Bim cells was fixed, permeabilized and stained with anti-Bim antibody (clone 9F5), followed by either of the biotinylated mouse anti-rat Ig isotype specific monoclonal antibodies: anti-rat IgG1 (A), anti-rat IgG2a (B), anti-rat IgG2b (C), a control antibody (D) or directly with anti-rat Igκ light chain conjugated to FITC (E and F [negative control]). In the case of staining with biotinylated antibodies, FITC-coupled streptavidin was used as the tertiary reagent. The double peaks (B and E) indicate that 9F5 is an antibody of the IgG2a/κ isotype.

Antibody isotyping was also achieved by a simple adaptation of the staining protocol (FIG. 2). The mixture of FDC-P1/Bcl-2 cells and FDC-P1/Bcl-2/EE-$Bim_L$ cells was fixed, permeabilized and stained with each of the three anti-Bim antibodies. As a secondary reagent biotinylated mouse anti-rat Ig isotype specific monoclonal antibodies were used: anti-rat IgG1 (RG11/39.4), anti-rat IgG2a (RG7/1.30) and anti-rat IgG2b (RG7/11.1) (Springer et al., 1982) and in the final step FITC-coupled streptavidin. To determine the Ig light chain isotype of the antibodies, we used FITC-coupled Mar 18.5 (Lanier et al. 1982) mouse anti-rat Igκ_antibodies. This analysis demonstrated that the 4E4 and 5E5 antibodies are IgG2b/κ and the 9F5 antibody is IgG2a/K (FIG. 11).

Figure 12:
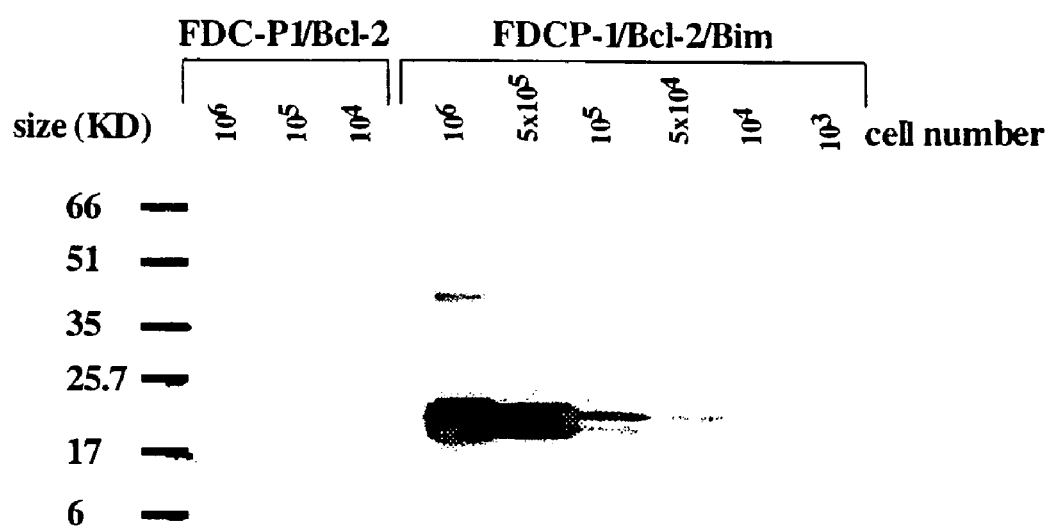
FIG. 12 is a photographical representation of anti-Bim monoclonal antibody detecting Bim by Western blotting. Expression of EE-Bim$_L$ in FDC-P1/Bcl-2/EE-Bim$_L$ cell lysates ($10^3$–$10^6$ cells) was analyzed by Western blotting using the anti-Bim antibody (9F5) and goat anti-rat Ig conjugated to HRP as a secondary reagent and detection by enhanced chemiluminescence. Lysates from FDC-P1/Bcl-2 cells were used as negative controls. A specific band of ~23 kD, corresponding to EE Bim$_L$, was only detected in FDC-P1/Bcl-2/EE-Bim$_L$ lysates and could not be detected in lysates from fewer than 5×$10^4$ cells. The upper band in the lane which contains lysate from $10^6$ FDC-P1/Bcl-2/EE-Bim cells is an artefact of overloading which led to retention of some Bim protein during electrophoresis.
Figure 13:
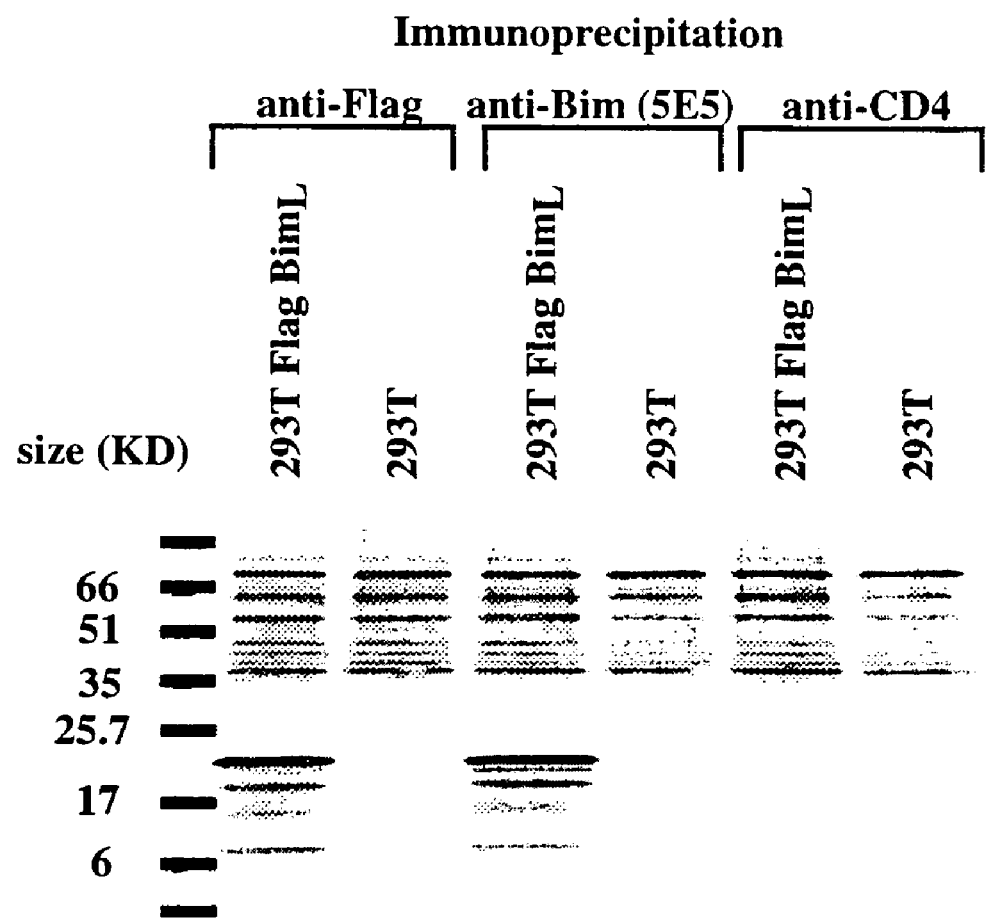
FIG. 13 is a photographical representation of anti-Bim monoclonal antibody detecting Bim by immunoprecipitation. Equivalent lysates from metabolically labelled 293T cells (lanes 2, 4 and 6) or 293T cells transiently transfected with a FLAG-Bim$_L$ expression construct (lanes 1, 3 and 5) were immunoprecipitated using the anti-FLAG antibody M2 (lanes 1 and 2), the anti-Bim antibody 5E5 (lanes 3 and 4) or an isotype-matched control antibody to mouse CD4 (lanes 5 and 6). Both the anti-FLAG antibody and the anti-Bim 5E5 antibody immunoprecipitated a 23 kD protein that corresponded with the expected mobility of FLAG-Bim$_L$.

Bim could be detected in Western analysis by all three anti-Bim antibodies in lysates obtained from as few as $5\times10^4$ FDC-P1/Bcl-2/EE-$Bim_L$ cells when binding of the secondary antibody was revealed by enhanced chemiluminescence (ECL) (FIG. 12). The three anti-Bim antibodies were also capable of immunoprecipitating $Bim_L$ protein from 293T cells that had been transiently transfected with a FLAG$Bim_L$ expression construct (FIG. 13). Both the Western blotting and immunoprecipitation assays clearly showed that the monoclonal anti-Bim antibodies were specific, as only $Bim_L$ was seen in FDC-P1/Bcl-2/EE-$Bim_L$ cells and no non-specific protein was detected in FDC-P1/Bcl-2 cells.

EXAMPLE 14

Fine-Mapping of the Dynein Light Chain Binding Region in Bim $Bim_S$, which lacks amino acids 42–71 found in murine $Bim_L$ and 42–127 in murine $Bim_{EL}$ (O'Connor, et al, EMBO J, 1998), is incapable of interacting with dynein light chain whereas a BH3 deletion mutant of Bim (Δaa150–aa157) does bind. To determine precisely the amino acid residues required for binding, a fine mapping approach was undertaken using the yeast-reverse-two-hybrid-system (Vidal, et al, PNAS, 1996). The system was set up so that binding of $Bim_L$ (coupled to the GAL4 DNA binding domain) to dynein light chain (fused to the GAL4 activation domain) induces expression of orotidine-5-phosphate decarboxylase. This enzyme converts 5-fluoro-orotic acid (FOA) to 5-fluorouracil (5FU) which kills the cell. The region within $Bim_L$ spanning amino acids 1–149 was mutagenized by low fidelity PCR and recombined into the yeast vector encoding $Bim_L$. From 15,000 transformants 82 mutant clones of $Bim_L$ which failed to interact with dynein light chain were selected in the presence of 5FOA. These clones were tested for full length $Bim_L$ protein production by their ability to interact with Bcl-2. This was feasible because the BH3 region of Bim, necessary for interaction with Bcl-2, is 22 amino acids towards the N-terminus from the dynein light chain binding region (O'Connor, et al, EMBO J, 1998). This led to the identification of 24 mutant clones of $Bim_L$ which did not interact with dynein light chain but could still bind to Bcl-2. Residues D51, K52, S53, T54 and appeared to be most critical for binding of $Bim_L$ to dynein light chain.

Four of the $Bim_L$ mutants from the reverse yeast-two-hybrid screening were randomly chosen for further investigation: D51G, S53P, T54A and the double mutant T54I/N65S. A quantitative analysis of the strength of interaction between $Bim_L$ or the four mutants with dynein light chain or, as a control Bcl-2, was performed in a yeast-two-hybrid assay by measuring β-galactosidase activity using ONPG as the substrate. Wild-type $Bim_L$ and the four $Bim_L$ mutants had comparable strength of interaction with Bcl-2. In contrast, when binding to dynein light chain was studied it became apparent that S53P, T54A and T54T/N65S had less than 0.1% of the activity compared to wild-type $Bim_L$ while the D51G mutant was intermediary and retained approximately 5–10% of the affinity.

Interaction between wild-type $Bim_L$ or the four $Bim_L$ mutants with dynein light chain or Bcl-2 was also studied in co-immunoprecipitation assays. This was done in 293T cells transiently transfected with Bim, Bcl-2 and dynein light chain expression constructs and in FDC-P1 cells stably transfected with Bim and Bcl-2 expression constructs. These experiments confirmed that all four mutants of $Bim_L$ could efficiently interact with Bcl-2 but were unable to bind to dynein light chain. Collectively, these results demonstrate that amino acid residues D51, S53 and T54 within Bim are critical for interaction with dynein light chain.

EXAMPLE 15

Binding to Dynein Light Chain Regulates the Pro-Apoptotic Activity of Bim

Cytoplasmic dynein light chain is a component of the minus end directed dynein motor complex, an evolutionarily conserved microtubule bound ATPase, which is involved in flagellar movement in *Chlamydomonas* and retrograde organelle transport in mammalian cells. Dynein heavy chain and dynein intermediate chains are integral structural components of the dynein ATPase complex. Dynein light chain is also a stoichiometric component of this complex but its biochemical function is presently not known.

$Bim_S$, the splice variant of Bim, which does not bind to dynein light chain is a much more potent killer than $Bim_L$ or $Bim_{EL}$ (O'Connor et al., EMBO J, 1998). FDC-P1 clones were generated which stably express Bcl-2 together with $Bim_S$, $Bim_L$ or $Bim_L$ bearing the mutations which abolish binding to dynein light chain and analysed their sensitivity to apoptotic stimuli. Three clones of each genotype, matched for equal levels of Bcl-2 and Bim proteins were selected for analysis. Parental FDC-P1 cells and transfectants expressing only Bcl-2 were used as additional controls.

Upon cytokine deprivation or γ-irradiation FDC-P1 cells expressing Bcl-2 and $Bim_S$ died much more rapidly than those expressing Bcl-2 plus $Bim_L$. Three of the $Bim_L$ mutants, S53P, T54A and the double mutant T54I/N65S were as potent inducers of apoptosis as $Bim_S$. In contrast, the D51G mutant, which retains some ability to bind to a dynein light chain, did not influence the killing potential of Bim and behaved like $Bim_L$. These results demonstrate that interaction with dynein light chain regulates the pro-apoptotic activity of Bim.

EXAMPLE 16

Immunohistochemical Analysis of Bim Expression in Mouse Tissues

Immunohistochemical staining intensity grading 0 negative

1+weak positive

2+moderately positive

3+strongly positive

4+extremely intense positive

Salivary Glands

Serous type cells of the parotid gland and the serous type cells of the submandibular gland (mixed serous and mucus secreting cells) 2–3+Bim immunoreactivity. The Mucus type cells of the sublingual gland had no Bim immunoreactivity.

Pancreas

Bim immunoreactivity (2–3+) detected on the ductal epithelial cells and more intensely (3–4+) in the cells of neuroendocrine origin in the islets. The exocrine/acinar tissue contained no Bim immunoreactivity (0).

Thymus

Thymic medulla strongly positive (3+), medullary thymocytes variably positive (0–3+). Cortical thymocytes mostly negative with scattered cells containing Bim immunoreactity (0–3+).

Spleen

Megakaryocytes of the red pulp 3+ Bim immunoreactivity but RBC negative. B and T zone areas of the white pulp strongly Bim positive (3+), plasma cells also had strong Bim immunoreactivity.

Kidney

Weak Bim immunoreactivity detected on most tubular epithelia (1+), but strikingly more intense in the epithelial cells of the proximal convoluted tubules at the corticomedullary junction (3–4+):

Striated Muscle

Appearance of a punctate pattern of Bim immunoreactivity along the muscle fibres (1–2$^+$). When in the correct plain of section the transverse cross-strations of the cylindrical myofibrils in the sarcoplasm of the muscle fibres containing strong Bi, immunoreactivity (3$^+$).

Liver

Liver hepatocytes and Kupffer cells have no Bim immunoreactivity (0), but the bile duct epithelial cells have moderate Bim immunoreactivity (2–3$^+$).

Intestine

Small intestine: intense Bim staining detected in the enterocytes lining the villi (3–4$^+$). Colon: enterocytes of the shorter villi and also the cells lining the crypts and strong Bim immunoreactivity (3–4$^+$).

Heart

Cross striations in the cytoplasm of cardiac involunatry striated muscle had prominant Bim immunoreactivity (3$^+$), particularly around the outer walls of cardiac chambers and muscles around the outer walls of cardiac chambers and muscles around cardiac blood vessels.

Testes

Bim immunoreactivity was absent from sertoli cells Leydig cells, spermatogonia, spermocytes and spermatids (0), but mature sperm and residual bodies were strongly positive (4$^+$).

Ovary

Follicular cells or ripening follicle prominantly stained (2–3$^+$), less intense Bim immunoreactivity observed in the interstitial cells, primordial follicles and corpus leteum (1–2$^+$).

| EXPRESSION ANALYSIS OF BIM IN CELL LINES BY IP WESTERN | | | |
|---|---|---|---|
| Cell line | Origin | Species | Bim Expression |
| ALB 8.1 | B lymphoma | mouse | + |
| KO52 DA.20 | T lymphoma | mouse | + |
| WEHI 703 | T lymphoma | mouse | + |
| B6.2.16.BW2 | T lymphoma | mouse | ++ |
| RAW 264.7 | Macrophage | mouse | + |
| J774/2 | Macrophage | mouse | + |
| F4N/3 | erythroleukaemia | mouse | weak + |
| TS5 | erythroleukaemia | mouse | weak + |
| DP10 | erythroleukaemia | mouse | weak + |
| C2Cl2 | muscle (myoblasts) | mouse | − |
| L6 | muscle (myoblasts) | rat | − |
| 416B | myeloid | mouse | + |
| P185X-2.1 | mastocytoma | mouse | + |
| FDC-P1 | myeloid | mouse | − |
| NIH3T3 | fibroblast | mouse | +/− |
| WEHI 11 | sarcoma | mouse | + |
| WEHI 164 | sarcoma | mouse | − |
| S17 | stromal | mouse | − |
| L929 | fibroblast | mouse | +/− |
| MCF-7 | breast carcinoma | human | ++ |
| MDCK | kidney | dog | − |
| 293T | embryonic kidney | human | + |
| HK-2 | kidney proximal | human | − |
| G-401 | Wilm's tumour | human | − |
| TCMK-1 | kidney | mouse | + |
| Cosm6 | kidney | monkey | + |
| MH134 | hepatoma | mouse | + |
| SW480 | colon carcinoma | human | − |
| EB-3 | colon carcinoma | human | − |

| LIST OF RAT ANTI-BIM ANTIBODIES | | | | |
|---|---|---|---|---|
| | | FACS | | |
| CLONE | ISOTYPE | mBIM S | mBIM EL/L | huBIM EL\L |
| 7H1 | ? K | + | + | − |
| 8D1 | ? K | + | + | − |
| 8F1 | ? K | + | + | − |
| 9A12 | IgG2aK | + | + | + |
| 14A8 | IgG2aK | + | + | + |
| 16C4 | IgG2aK | + | + | − |
| 17C7 | ? | + | + | − |
| 6A3 | IgG1K | + | + | − |
| 18D7 | ? K | + | − | − |
| 5E8 | ? | + | | |
| 5E5 | IgG2bK | − | + | + |
| 4E4 | IgG2bK | − | + | + |
| 9F5 | IgG2aK | − | + | + |

| LIST OF RAT ANTI-BIM ANTIBODIES | | | |
|---|---|---|---|
| WESTERN | | | |
| mBIM S | mBIM L | mBIM EL | huBIM EL/L |
| + | + | + | + |
| + | + | + | − |
| + | + | + | − |
| + | + | + | + |
| + | + | + | + |
| weak | + | + | v. weak |
| weak | + | + | + |
| ? | ? | + | − |
| | + | + | + |
| − | + | ? v. weak | + |
| − | + | ? v. weak | + |
| − | + | ? v. weak | + |

EXAMPLE 17

Disruption of Bim

Figure 14:
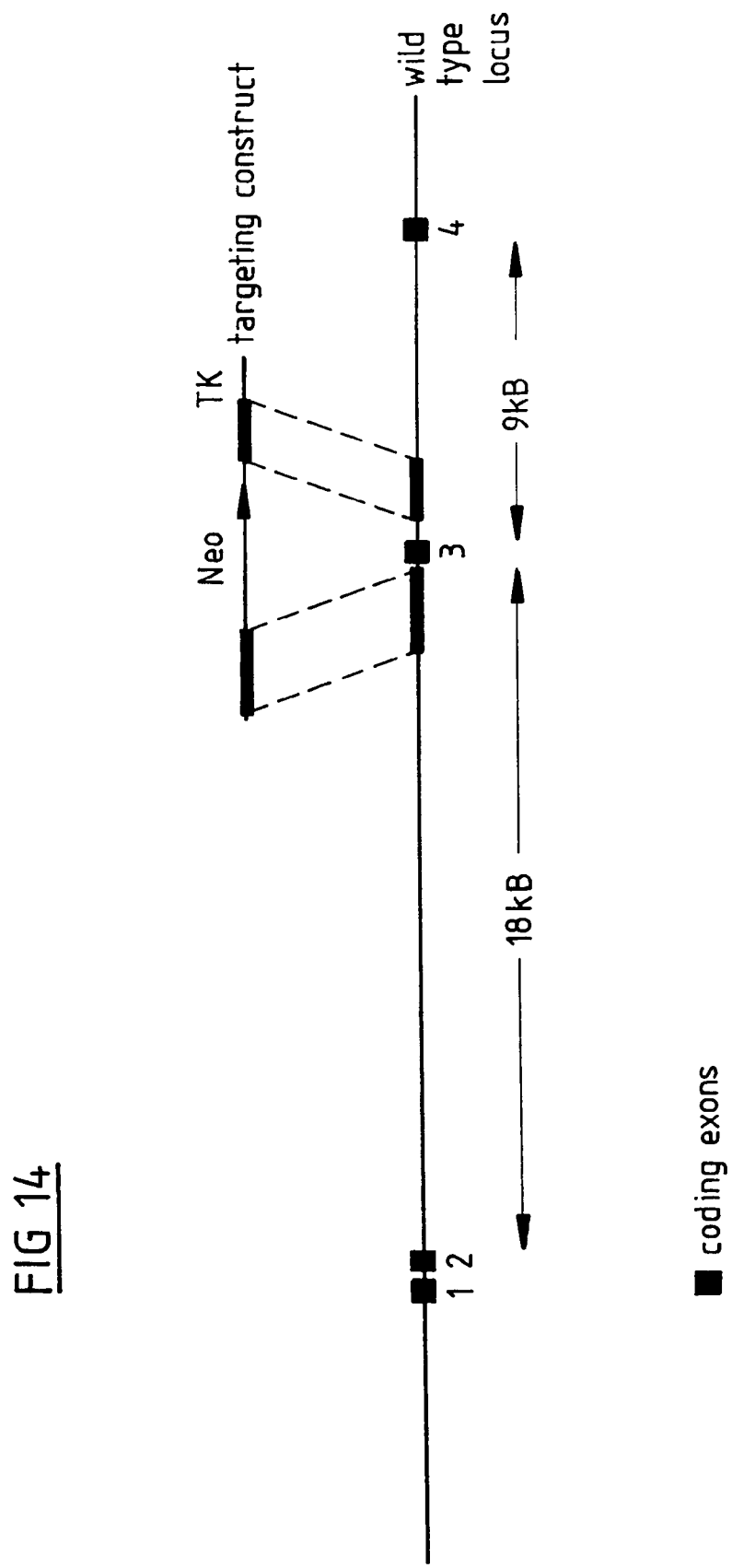
FIG. 14 is a schematic representation of the gene targeting vector utilised in making Bim knockout mice.

The Bim gene was inactivated by homologous recombination. The gene targeting vector (see FIG. 14) was assembled in ploxPneo-1 in which a neomycin phosphotransferase gene (neo$^r$), driven by a phosphoglycerate kinase (PGK) promoter, is flanked by bacteriophage P1 loxP sites. The 129/Sv mouse Bim genomic DNA sequences introduced at each end of the loxP-neo$^r$loxP cassette comprised the 4,000 bp region immediately upstream of the Bim exon 3 and the 2,700 bp downstream from exon 3. Introduction of a terminal herpes simplex virus thymidine kinase (tk) gene driven by a PGK promoter then completed the vector, which was linearized and electroporated into W9.5 ES cells (Koentgen et al., 1995). ES cell clones selected for resistance to G418 (i.e. neo$^r$ gene integration) and gancyclovir (i.e. loss of the tk gene following homologous recombination) (Mansour et al., 1988) were screened for homologous recombination at the Bim locus by Southern blot analysis. The Bim mutant ES cell clones were injected into the blastocoel cavity of 129/Sv blastocysts, which were then implanted into pseudopregnant foster mothers. Male chimeric progeny were crossed to 129/Sv females or, to delete the neo$^r$ cassette, to B6/FVB F1 females expressing bacteriophage P1 Cre recombinase (Cre) (Lakso et al., 1996).

EXAMPLE 18

The Genomic Location of the Mouse and Human Bim Genes

The genomic localisation of the mouse and human Bim genes was determined by hybridisation. $^3$H-thymidine labelled mouse $Bim_L$ probes was used to probe a normal mouse metaphase spread. This demonstrated that the mouse Bim gene is located on chromosome 2 at bands F3-G. The corresponding localisation of human Bim gene was determined by fluorescence in situ hybridisation (FISH). A human $Bim_L$ cDNA probe was nick-translated with biotin-14-dATP and hybridised in situ to normal male metaphases. The human gene is found in the syntenic region on chromosome 2 at bands 2q12–2q13.

EXAMPLE 19

Mutant Mice Lacking Bim

To determine the essential biological function of Bim, mice with a germline mutation in Bim have been generated. A number of characteristic abnormalities have been identified. Firstly, in an intercross of Bim +/–animals the number of Bim –/–offspring is significantly less than the expected 25%. This indicates that Bim may have an essential role in embryogenesis but that it can be partially compensated by related molecules. The Bim –/–mice that are generated have no obvious physical abnormality and both females and males are fertile. It is possible that the genetic background influences the phenotype of the Bim –/–mutation. Analysis of the haematopoietic compartment has shown that the Bim –/–mice have increased numbers of blood leukocytes (~2-fold) and increased numbers of spleen cells (also ~2-fold). In the thymus the numbers of $CD4^+$ $CD8^+$ pre T cells are reduced (~2-fold) and the numbers of mature $CD4^+$ $CD8^-$ and $CD4^+$ $CD8^+$ T cells are increased (~2- to 3-fold). Cell survival analysis on purified $CD4^{+w\ CD}8^+$ pre T cells demonstrated that the Bim –/–cells are considerably more resistant to a range of apoptotic stimuli (growth factor deprivation, corticosteroids, DNA damage, calcium ionophores and phorbol esters) compared to control cells. The cells from the heterozygous Bim +/–mice were also more resistant than the cells from normal mice.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Altschul, S. F., Gish, W., Miller, W., Myers, E. W. and Lipman, D. J. (1990) *J. Mol. Biol.*, 215, 403–410.

Blanar, M. and Rutter, W. (1992) *Science* 256, 1014–1018.

Boise, L. H., Gonzalez-Garcia, M., Postema, C. E., Ding, L., Lindsten, T., Turka, L. A., Mao, X., Nunez, G. and Thompson, C. B. (1993) *Cell* 74, 597–608.

Boise, L. H., Minn, A. J., Noel, P. J., June, C. H., Accavitti, M. A., Lindsten, T. and Thompson, C. B. (1995) *Immunity* 3, 87–98.

Borner, C., Martinou, I., Mattmann, C., Irmler, M., Schaerer, E., Martinou, J.-C. and Tschopp, J. (1994) *J. Cell Biol.*, 126, 1059–1068.

Boyd, J. M., Gallo, G. J., Elangovan, B., Houghton, A. B., Malstrom, S., Avery, B. J., Ebb, R. G., Subramanian, T., Chittenden, T., Lutz, R. J. and Chinnadurai, G. (1995) *Oncogene*, 11, 1921–1928.

Cheng, E. H.-Y., Levine, B., Boise, L. H., Thompson, C. G. and Hardwick, J. M. (1996) *Nature*, 379, 554–556.

Chittenden, T., Flemington, C., Houghton, A. B., Ebb, R. G., Gallo, G. J., Elangovan, B., Chinnadurai, G. and Lutz, R. J. (1995) *EMBO J.*, 14, 5589–5596.

Chittenden, T., Harrington, E. A., O'Connor, R., Flemington, C., Lutz, R. J., Evan, G. I. and Guild, B. C. (1995) *Nature*, 374, 733–736.

Crissman, H. A., Darzynkiewicz, Z., Steinkamp, J. A. and Tobey, R. A. (1990) *Methods Cell. Biol.*, 33, 305–314.

Dexter, T. M., G. D. Scott, E. Scolnick, and D. Metcalf (1980) *J. Exp. Med.* 152: 1036–1047.

Farrow, S. N., White, J. H. M., Martinou, I., Raven, T., Pun, K.-T., Grinham, C. J., Martinou, J. C. and Brown, R. (1995) *Nature*, 374, 731–733.

Galfre, G., S. C. Howe, C. Milstein, G. W. Butcher, and J. C. Howard (1977) *Nature* 266: 550–552.

Gibson, L., Holmgreen, S., Huang, D. C. S., Bernard, O., Copeland, N. G., Jenkins, N. A., Sutherland, G. R., Baker, E., Adams, J. M. and Cory, S. (1996) *Oncogene*, 13, 665–675.

Grussenmeyer, T., Scheidtmann, K. H., Hutchinson, M. A., Eckhart, W. and Walter, G. (1985) *Proc. Natl. Acad. Sci. USA*, 82, 7952–7954.

Han, J., Sabbatini, P. and White, E. (1996) *Mol. Cell. Biol.*, 16, 5857–5864.

Hanada, M., Aime-Sempe, C., Sato, T. and Reed, J. C. (1995) *J. Biol. Chem.*, 270, 11962–11969.

Henderson, S., Huen, D., Rowe, M., Dawson, C., Johnson, G. and Rickinson, A. (1993) *Proc. Natl. Acad. Sci. USA*, 90, 8479–8483.

Horton, R. M., Ho, S. N., Pullen, J. K., Hunt, H. D., Cai, Z. and Pease, L. R. (1993) *Methods Enzymol.*, 217, 270–279.

Huang, D. C. S., Cory, S. and Strasser, A. (1997) *Oncogene*, 14, 405–414.

Huang, D. C. S., O'Reilly, L. A., Strasser, A. and Cory, S. (1997) *EMBO J.*, 16, 4628–4638.

Huang, D. C. S., S. Cory, and A. Strasser (1997) *Oncogene* 14: 405–414.

Inohara, N., Ding, L., Chen, S. and Nú-ez, G. (1997) *EMBO J.*, 16, 1686–1694.

Jacobson, M. D. (1997) *Curr. Biol.*, 7, R277–R281.

Jacobson, M. D., Weil, M. and Raff, M. C. (1997) *Cell*, 88, 347–354.

Karasuyama, H., and F. Melchers (1988) *Eur. J. Immunol.* 18: 97–104.

Kerr, J. F. R., Wyllie, A. H. and Currie, A. R. (1972) *Br. J. Cancer*, 26, 239–257.

Kiefer, M. C., Brauer, M. J., Powers, V. C., Wu, J. J., Umansky, S. R., Tomei, L. D. and Barr, P. J. (1995) *Nature*, 374, 736–739.

Koentgen et al. (1995). *Genes Develop* 9: 1965–1977

Krajewski, S., Tanaka, S., Takayama, S., Schibler, M. J., Fenton, W. and Reed, J. C. (1993) *Cancer Res.*, 53, 4701–4714.

Kroemer, G. (1997) *Nature Med.*, 3, 614–620.

Lakso et al. (1996). *Proc. Natl. Acad. Sci. USA* 93: 5860–5865

Lanier, L. I., G. A. Gutman, D. E. Lewis, S. T. Griswold, and N. L. Warner (1982) *Hybridoma* 1:125–131.

Lithgow, T., van Driel, R., Bertram, J. F. and Strasser, A. (1994) *Cell Growth Differ.*, 5, 411–417.

Mansour et al. (1988). *Nature* 336: 348.-352

Monaghan, P., Robertson, D., Amos, T. A. S., Dyer, M. J. S., Mason, D. Y. and Greaves, M. F. (1992) *J. Histochem. Cytochem.*, 40, 1819–1825.

Muchmore, S. W., Sattler, M., Liang, H., Meadows, R. P., Harlan, J. E., Yoon, H. S., Nettesheim, D., Chang, B. S., Thompson, C. B., Wong, S.-L., Ng, S.-C. and Fesik, S. W. (1996) *Nature*, 381, 335–341.

Nicholson, D. W. and Thornberry, N. A. (1997) *Trends Biochem. Sci.*, 22, 299–306.

Nicoletti, I., Migliorati, G., Pagliacci, M. C., Grignani, F. and Riccardi, C. (1991) *J. Immunol. Meth.*, 139, 271–279.

O'Connor, L., A. Strasser, L. A. O'Reilly, G. Hausmann, J. M. Adams, S. Cory, and D. C. S. Huang (I 998) *EMBO J.* 17: 384–395.

O'Reilly, L., Huang, D. C. S. and Strasser, A. (1996) *EMBO J.*, 15, 6979–6990.

Oltvai, Z. N., Milliman, C. L. and Korsmeyer, S. J. (1993) *Cell,* 74, 609–619.

Pezzella, F., Tse, A. G. D., Cordell, J. L., Pulford, K. A. F., Gatter, K. C. and Mason, D. Y. (1990) *Am. J. Path.*, 137, 225–232.

Reed, J. C. (1997) *Nature,* 387, 773–776.

Sattler, M., Liang, H., Nettesheim, D., Meadows, R. P., Harlan, J. E., Eberstadt, M., Yoon, H. S., Shuker, S. B., Chang, B. S., Minn, A. J., Thompson, C. B. and Fesik, S. W. (1997) *Science,* 275, 983–986.

Sedlak, T. W., Oltvai, Z. N., Yang, E., Wang, K., Boise, L. H., Thompson, C. B. and Korsmeyer, S. J. (1995) *Proc. Natl. Acad. Sci. USA,* 92, 7834–7838.

Shulman, M., C. D. Wilde, and G. Kshler (1978) *Nature* 276: 269–270.

Smith, D. B., and K. S. Johnson (1988) *Gene* 6788: 31–40.

Springer, T. A., A. Bhattacharya, J. T. Cardoza, and F. Sanchez-Madrid (1982) *Hybridoma* 1: 257–273.

Strasser, A., Harris, A. W., Huang, D. C. S., Krammer, P. H. and Cory, S. (1995) *EMBO J.*, 14, 6136–6147.

Strasser, A., Harris, A. W., Jacks, T. and Cory, S. (1994) *Cell,* 79, 329–339.

Vaux, D. L., Cory, S. and Adams, J. M. (1988) *Nature,* 335, 440–442.

Veis, D. J., Sentman, C. L., Bach, E. A. and Korsmeyer, S. J. (1993) *J. Immunol.*, 151, 2546–2554.

Wang, K., Yin, X.-M., Chao, D. T., Milliman, C. L. and Korsmeyer, S. J. (1996) *Genes Dev.*, 10, 2859–2869.

White, E., Sabbatini, P., Debbas, M., Wold, W. S. M., Kusher, D. I. and Gooding, L. R. (1992) *Mol. Cell. Biol.*, 12, 2570–2580.

Yin, X.-M., Oltvai, Z. N. and Korsmeyer, S. J. (1994) *Nature,* 369, 321–323.

Zha, H., Aimé-Sempé, C., Sato, T. and Reed, J. C. (1996) *J. Biol. Chem.*, 271, 7440–7444.

---

The invention claimed is:

1. An isolated nucleic acid molecule comprising a nucleotide sequence encoding or complementary to a sequence encoding an amino acid sequence comprising SEQ ID NO:10 or having at least about 89% or greater identity to SEQ ID NO:10 wherein said amino acid sequence induces apoptosis.

2. An isolated nucleic acid molecule comprising SEQ ID NO:9.

3. The isolated nucleic acid molecule according to claim 1, wherein said nucleic acid molecule comprises a nucleotide sequence that encodes the amino acid sequence comprising SEQ ID NO: 10.

4. The isolated nucleic acid molecule according to claim 1, wherein said nucleic acid molecule comprises a nucleotide sequence encoding an amino acid sequence that is at least about 89% or greater identity to SEQ ID NO: 10, wherein said amino acid sequence induces apoptosis.

5. An isolated polypeptide comprising SEQ ID NO:10 or a sequence having at least about 89% identity to SEQ ID NO:10 wherein said polypeptide induces apoptosis.

6. The isolated polypeptide according to claim 5, wherein said polypeptide comprises the amino acid sequence of SEQ ID NO: 10.

7. The isolated polypeptide according to claim 5, wherein said polypeptide comprises an amino acid sequence comprising least about 89% identity to SEQ ID NO 10, wherein said polypeptide induces apoptosis.

* * * * *

UNITED STATES PATENT AND TRADEMARK OFFICE
CERTIFICATE OF CORRECTION

PATENT NO. : 7,064,193 B1
APPLICATION NO. : 09/508832
DATED : June 20, 2006
INVENTOR(S) : Cory et al.

It is certified that error appears in the above-identified patent and that said Letters Patent is hereby corrected as shown below:

Title page, column 2, line 5, delete "et al" and insert -- et al. --

Title page, column 2, line 6, delete "et al" and insert -- et al. --

Title page, column 2, line 7, delete "et al" and insert -- et al. --

Title page, column 2, line 9, delete "et al' and insert -- et al., --

Title page, column 2, line 11, delete "et al" and insert -- et al. --

Title page, column 2, line 11, delete "73," and insert -- 74, --

Column 2, lines 50-51, delete "abbreviationX" and insert -- abbreviation X --

Column 3, line 50, delete "derivatice" and insert -- derivative --

Column 9, line 29, delete "0.5/g" and insert -- 0.5 μg --

Column 9, line 42, delete "≡.BH3" and insert -- ΔBH3 --

Column 10, line 31, delete "EE $Bim_L$," and insert -- EE–$Bim_L$, --

Column 10, lines 48-49, delete "targetting" and insert -- targeting --

Column 16, line 6, delete "analogueues" and insert -- analogues --

Column 17, line 3, delete "derivatice" and insert -- derivative --

Column 18, line 67, delete "Bcl–XL." and insert -- Bcl–$x_L$. --

Column 19, line 30, delete "homologueues" and insert -- homologues --

Column 27, line 62, delete "fluorscence" and insert -- fluorescence --

Column 27, line 63, delete "fluorscence" and insert -- fluorescence --

Column 27, line 67, delete "fluorscence" and insert -- fluorescence --

Column 28, line 3, delete "fluorscence" and insert -- fluorescence --

Column 28, line 38, delete "promyelomoncytic" and insert -- promyelomonocytic --

UNITED STATES PATENT AND TRADEMARK OFFICE
CERTIFICATE OF CORRECTION

PATENT NO.       : 7,064,193 B1
APPLICATION NO.  : 09/508832
DATED            : June 20, 2006
INVENTOR(S)      : Cory et al.

It is certified that error appears in the above-identified patent and that said Letters Patent is hereby corrected as shown below:

Column 30, line 63, delete "fluorecein" and insert -- fluorescein --

Column 31, line 51, delete "K052DA20" and insert -- KO52DA20 --

Column 31, line 57, delete "K052DA20" and insert -- KO52DA20 --

Column 31, line 59, delete "Bim$_L$" and insert -- bim$_L$ --

Column 32, line 16, delete "K052DA20" and insert -- KO52DA20 --

Column 32, line 35, delete "Bim$_L$" and insert -- bim$_L$ --

Column 32, line 46, below "the two proteins" delete "co–localised (FIG. 3D)." and insert the same after "the two proteins" on line 45

Column 33, line 40, delete "Bim$_L$" and insert -- bim$_L$ --

Column 33, line 42, delete "Bim$_L$" and insert -- bim$_L$ --

Column 34, line 2, delete "Bin" and insert -- Bim --

Column 34, line 8, delete "Bim$_L$" and insert -- bim$_L$ --

Column 34, line 66, delete "Bim$_L$" and insert -- bim$_L$ --

Column 35, line 26, delete "K052DA20" and insert -- KO52DA20 --

Column 35, line 53, delete "A" and insert -- $\lambda$ --

Column 37, line 63, delete "$^{125}$1–labelled" and insert -- $^{125}$I–labelled --

Column 18, line 38, delete "–5–" and insert -- –S– --

Column 38, line 33, delete "permited" and insert -- permitted --

Column 38, line 52, delete "Bim$_L$" and insert -- bim$_L$ --

Column 40, line 55, delete "IgG2a/K" and insert -- IgG2a/$_K$ --

Column 40, line 62, delete "FLAGBim$_L$" and insert -- FLAGbim$_L$ --

UNITED STATES PATENT AND TRADEMARK OFFICE
CERTIFICATE OF CORRECTION

PATENT NO. : 7,064,193 B1
APPLICATION NO. : 09/508832
DATED : June 20, 2006
INVENTOR(S) : Cory et al.

It is certified that error appears in the above-identified patent and that said Letters Patent is hereby corrected as shown below:

Column 41, line 43, delete "T54T/N65S" and insert -- T54I/N65S --

Column 42, line 10, after "or" delete "$Bim_L$" and insert -- $bim_L$ --

Column 42, line 67, delete "(3–4$^+$):" and insert -- (3–4$^+$). --

Column 43, line 4, delete "cross–strations" and insert -- cross–striations --

Column 43, line 20, delete "involunatry" and insert -- involuntary --

Column 43, line 21, delete "prominant" and insert -- prominent --

Column 43, line 33, delete "prominantly" and insert -- prominently --

Column 45, line 39, delete "CD4$^{+w\,CD}$8$^+$" and insert -- CD4$^+$CD8$^+$ --

Column 46, line 29, delete "Scheidtrnann," and insert -- Scheidtmann, --

Column 47, line 16, delete "(I 998)" and insert -- (1998) --

Column 47, lines 28-30, below "Eberstadt, M.," delete "Yoon, H. S., ................ .................275, 983–986." and insert the same after "Eberstadt, M.," on line 27.

Column 48, line 4, delete "Kshler" and insert -- Kšhler --

Column 70, line 12 claim 17, after "comprising" insert -- at --

Signed and Sealed this

Ninth Day of January, 2007

JON W. DUDAS
*Director of the United States Patent and Trademark Office*

SEQUENCE LISTING

```
<160> NUMBER OF SEQ ID NOS: 39

<210> SEQ ID NO 1
<211> LENGTH: 332
<212> TYPE: DNA
<213> ORGANISM: Mus sp.
<220> FEATURE:
<221> NAME/KEY: CDS
<222> LOCATION: (1)..(330)

<400> SEQUENCE: 1 atg gcc aag caa cct tct gat gta agt tct gag tgt gac aga gaa ggt        48
Met Ala Lys Gln Pro Ser Asp Val Ser Ser Glu Cys Asp Arg Glu Gly
 1               5                  10                  15 gga caa ttg cag cct gct gag agg cct ccc cag ctc agg cct ggg gcc        96
Gly Gln Leu Gln Pro Ala Glu Arg Pro Pro Gln Leu Arg Pro Gly Ala
             20                  25                  30 cct acc tcc cta cag aca gaa ccg caa gct tcc ata cga cag tct cag       144
Pro Thr Ser Leu Gln Thr Glu Pro Gln Ala Ser Ile Arg Gln Ser Gln
         35                  40                  45 gag gaa cct gaa gat ctg cgc ccg gag ata cgg att gca cag gag ctg       192
Glu Glu Pro Glu Asp Leu Arg Pro Glu Ile Arg Ile Ala Gln Glu Leu
     50                  55                  60 cgg cgg atc gga gac gag ttc aac gaa act tac aca agg agg gtg ttt       240
Arg Arg Ile Gly Asp Glu Phe Asn Glu Thr Tyr Thr Arg Arg Val Phe
 65                  70                  75                  80 gca aat gat tac cgc gag gct gaa gac cac cct caa atg gtt atc tta       288
Ala Asn Asp Tyr Arg Glu Ala Glu Asp His Pro Gln Met Val Ile Leu
                 85                  90                  95 caa ctg tta cgc ttt atc ttc cgt ctg gta tgg aga agg cat tg            332
```

```
Gln Leu Leu Arg Phe Ile Phe Arg Leu Val Trp Arg Arg His
        100                 105                 110

<210> SEQ ID NO 2
<211> LENGTH: 110
<212> TYPE: PRT
<213> ORGANISM: Mus sp.

<400> SEQUENCE: 2

Met Ala Lys Gln Pro Ser Asp Val Ser Ser Glu Cys Asp Arg Glu Gly
  1               5                  10                  15

Gly Gln Leu Gln Pro Ala Glu Arg Pro Pro Gln Leu Arg Pro Gly Ala
             20                  25                  30

Pro Thr Ser Leu Gln Thr Glu Pro Gln Ala Ser Ile Arg Gln Ser Gln
         35                  40                  45

Glu Glu Pro Glu Asp Leu Arg Pro Glu Ile Arg Ile Ala Gln Glu Leu
 50                  55                  60

Arg Arg Ile Gly Asp Glu Phe Asn Glu Thr Tyr Thr Arg Arg Val Phe
 65                  70                  75                  80

Ala Asn Asp Tyr Arg Glu Ala Glu Asp His Pro Gln Met Val Ile Leu
                 85                  90                  95

Gln Leu Leu Arg Phe Ile Phe Arg Leu Val Trp Arg Arg His
        100                 105                 110

<210> SEQ ID NO 3
<211> LENGTH: 422
<212> TYPE: DNA
<213> ORGANISM: Mus sp.
<220> FEATURE:
<221> NAME/KEY: CDS
<222> LOCATION: (1)..(420)

<400> SEQUENCE: 3 atg gcc aag caa cct tct gat gta agt tct gag tgt gac aga gaa ggt      48
Met Ala Lys Gln Pro Ser Asp Val Ser Ser Glu Cys Asp Arg Glu Gly
  1               5                  10                  15 gga caa ttg cag cct gct gag agg cct ccc cag ctc agg cct ggg gcc      96
Gly Gln Leu Gln Pro Ala Glu Arg Pro Pro Gln Leu Arg Pro Gly Ala
             20                  25                  30 cct acc tcc cta cag aca gaa ccg caa gac agg agc ccg gca ccc atg     144
Pro Thr Ser Leu Gln Thr Glu Pro Gln Asp Arg Ser Pro Ala Pro Met
         35                  40                  45 agt tgt gac aag tca aca caa acc cca agt cct cct tgc cag gcc ttc     192
Ser Cys Asp Lys Ser Thr Gln Thr Pro Ser Pro Pro Cys Gln Ala Phe
 50                  55                  60 aac cac tat ctc agt gca atg gct tcc ata cga cag tct cag gag gaa     240
Asn His Tyr Leu Ser Ala Met Ala Ser Ile Arg Gln Ser Gln Glu Glu
 65                  70                  75                  80 cct gaa gat ctg cgc ccg gag ata cgg att gca cag gag ctg cgg cgg     288
Pro Glu Asp Leu Arg Pro Glu Ile Arg Ile Ala Gln Glu Leu Arg Arg
                 85                  90                  95 atc gga gac gag ttc aac gaa act tac aca agg agg gtg ttt gca aat     336
Ile Gly Asp Glu Phe Asn Glu Thr Tyr Thr Arg Arg Val Phe Ala Asn
            100                 105                 110 gat tac cgc gag gct gaa gac cac cct caa atg gtt atc tta caa ctg     384
Asp Tyr Arg Glu Ala Glu Asp His Pro Gln Met Val Ile Leu Gln Leu
        115                 120                 125 tta cgc ttt atc ttc cgt ctg gta tgg aga agg cat tg                  422
Leu Arg Phe Ile Phe Arg Leu Val Trp Arg Arg His
        130                 135                 140
```

```
<210> SEQ ID NO 4
<211> LENGTH: 140
<212> TYPE: PRT
<213> ORGANISM: Mus sp.

<400> SEQUENCE: 4

Met Ala Lys Gln Pro Ser Asp Val Ser Ser Glu Cys Asp Arg Glu Gly
  1               5                  10                  15

Gly Gln Leu Gln Pro Ala Glu Arg Pro Pro Gln Leu Arg Pro Gly Ala
             20                  25                  30

Pro Thr Ser Leu Gln Thr Glu Pro Gln Asp Arg Ser Pro Ala Pro Met
         35                  40                  45

Ser Cys Asp Lys Ser Thr Gln Thr Pro Ser Pro Pro Cys Gln Ala Phe
 50                  55                  60

Asn His Tyr Leu Ser Ala Met Ala Ser Ile Arg Gln Ser Gln Glu Glu
 65                  70                  75                  80

Pro Glu Asp Leu Arg Pro Glu Ile Arg Ile Ala Gln Glu Leu Arg Arg
                 85                  90                  95

Ile Gly Asp Glu Phe Asn Glu Thr Tyr Thr Arg Arg Val Phe Ala Asn
            100                 105                 110

Asp Tyr Arg Glu Ala Glu Asp His Pro Gln Met Val Ile Leu Gln Leu
            115                 120                 125

Leu Arg Phe Ile Phe Arg Leu Val Trp Arg Arg His
            130                 135                 140

<210> SEQ ID NO 5
<211> LENGTH: 590
<212> TYPE: DNA
<213> ORGANISM: Mus sp.
<220> FEATURE:
<221> NAME/KEY: CDS
<222> LOCATION: (1)..(588)

<400> SEQUENCE: 5 atg gcc aag caa cct tct gat gta agt tct gag tgt gac aga gaa ggt      48
Met Ala Lys Gln Pro Ser Asp Val Ser Ser Glu Cys Asp Arg Glu Gly
  1               5                  10                  15 gga caa ttg cag cct gct gag agg cct ccc cag ctc agg cct ggg gcc      96
Gly Gln Leu Gln Pro Ala Glu Arg Pro Pro Gln Leu Arg Pro Gly Ala
             20                  25                  30 cct acc tcc cta cag aca gaa ccg caa ggt aat ccc gac ggc gaa ggg     144
Pro Thr Ser Leu Gln Thr Glu Pro Gln Gly Asn Pro Asp Gly Glu Gly
         35                  40                  45 gac cgc tgc ccc cac ggc agc cct cag ggc ccg ctg gcc cca ccg gcc     192
Asp Arg Cys Pro His Gly Ser Pro Gln Gly Pro Leu Ala Pro Pro Ala
 50                  55                  60 agc cct ggc cct ttt gct acc aga tcc cca ctt ttc atc ttt gtg aga     240
Ser Pro Gly Pro Phe Ala Thr Arg Ser Pro Leu Phe Ile Phe Val Arg
 65                  70                  75                  80 aga tct tct ctg ctg tcc cgg tcc tcc agt ggg tat ttc tct ttt gac     288
Arg Ser Ser Leu Leu Ser Arg Ser Ser Ser Gly Tyr Phe Ser Phe Asp
                 85                  90                  95 aca gac agg agc ccg gca ccc atg agt tgt gac aag tca aca caa acc     336
Thr Asp Arg Ser Pro Ala Pro Met Ser Cys Asp Lys Ser Thr Gln Thr
            100                 105                 110 cca agt cct cct tgc cag gcc ttc aac cac tat ctc agt gca atg gct     384
Pro Ser Pro Pro Cys Gln Ala Phe Asn His Tyr Leu Ser Ala Met Ala
            115                 120                 125 tcc ata cga cag tct cag gag gaa cct gaa gat ctg cgc ccg gag ata     432
Ser Ile Arg Gln Ser Gln Glu Glu Pro Glu Asp Leu Arg Pro Glu Ile
```

| | | | | | | | | | | | | | | |
|---|---|---|---|---|---|---|---|---|---|---|---|---|---|---|
| Ser | Ile | Arg | Gln | Ser | Gln | Glu | Glu | Pro | Glu | Asp | Leu | Arg | Pro | Glu | Ile |
| | 130 | | | | 135 | | | | | 140 | | | | | |

```
cgg att gca cag gag ctg cgg cgg atc gga gac gag ttc aac gaa act       480
Arg Ile Ala Gln Glu Leu Arg Arg Ile Gly Asp Glu Phe Asn Glu Thr
145                 150                 155                 160 tac aca agg agg gtg ttt gca aat gat tac cgc gag gct gaa gac cac       528
Tyr Thr Arg Arg Val Phe Ala Asn Asp Tyr Arg Glu Ala Glu Asp His
                165                 170                 175 cct caa atg gtt atc tta caa ctg tta cgc ttt atc ttc cgt ctg gta       576
Pro Gln Met Val Ile Leu Gln Leu Leu Arg Phe Ile Phe Arg Leu Val
            180                 185                 190 tgg aga agg cat tg                                                    590
Trp Arg Arg His
        195
```

<210> SEQ ID NO 6
<211> LENGTH: 196
<212> TYPE: PRT
<213> ORGANISM: Mus sp.

<400> SEQUENCE: 6

Met Ala Lys Gln Pro Ser Asp Val Ser Ser Glu Cys Asp Arg Glu Gly
1               5                   10                  15

Gly Gln Leu Gln Pro Ala Glu Arg Pro Pro Gln Leu Arg Pro Gly Ala
            20                  25                  30

Pro Thr Ser Leu Gln Thr Glu Pro Gln Gly Asn Pro Asp Gly Glu Gly
        35                  40                  45

Asp Arg Cys Pro His Gly Ser Pro Gln Gly Pro Leu Ala Pro Ala
    50                  55                  60

Ser Pro Gly Pro Phe Ala Thr Arg Ser Pro Leu Phe Ile Phe Val Arg
65                  70                  75                  80

Arg Ser Ser Leu Leu Ser Arg Ser Ser Gly Tyr Phe Ser Phe Asp
                85                  90                  95

Thr Asp Arg Ser Pro Ala Pro Met Ser Cys Asp Lys Ser Thr Gln Thr
            100                 105                 110

Pro Ser Pro Pro Cys Gln Ala Phe Asn His Tyr Leu Ser Ala Met Ala
        115                 120                 125

Ser Ile Arg Gln Ser Gln Glu Glu Pro Glu Asp Leu Arg Pro Glu Ile
    130                 135                 140

Arg Ile Ala Gln Glu Leu Arg Arg Ile Gly Asp Glu Phe Asn Glu Thr
145                 150                 155                 160

Tyr Thr Arg Arg Val Phe Ala Asn Asp Tyr Arg Glu Ala Glu Asp His
                165                 170                 175

Pro Gln Met Val Ile Leu Gln Leu Leu Arg Phe Ile Phe Arg Leu Val
            180                 185                 190

Trp Arg Arg His
        195

<210> SEQ ID NO 7
<211> LENGTH: 416
<212> TYPE: DNA
<213> ORGANISM: Homo sapiens
<220> FEATURE:
<221> NAME/KEY: CDS
<222> LOCATION: (1)..(414)

<400> SEQUENCE: 7

```
atg gca aag caa cct tct gat gta agt tct gag tgt gac cga gaa ggt        48
Met Ala Lys Gln Pro Ser Asp Val Ser Ser Glu Cys Asp Arg Glu Gly
```

```
                                                                                              1                   5                     10                    15
aga caa ttg cag cct gcg gag agg cct ccc cag ctc aga cct ggg gcc        96
Arg Gln Leu Gln Pro Ala Glu Arg Pro Pro Gln Leu Arg Pro Gly Ala
                 20                  25                  30 cct acc tcc cta cag aca gag cca caa gac agg agc cca gca ccc atg       144
Pro Thr Ser Leu Gln Thr Glu Pro Gln Asp Arg Ser Pro Ala Pro Met
         35                  40                  45 agt tgt gac aaa tca aca caa acc cca agt cct cct tgc cag gcc ttc       192
Ser Cys Asp Lys Ser Thr Gln Thr Pro Ser Pro Pro Cys Gln Ala Phe
 50                  55                  60 aac cac tat ctc agt gca atg gct tcc atg agg cag gct gaa cct gca       240
Asn His Tyr Leu Ser Ala Met Ala Ser Met Arg Gln Ala Glu Pro Ala
 65                  70                  75                  80 gat atg cgc cca gag ata tgg atc gcc caa gag ttg cgg cgt atc gga       288
Asp Met Arg Pro Glu Ile Trp Ile Ala Gln Glu Leu Arg Arg Ile Gly
             85                  90                  95 gac gag ttt aac gct tac tat gca agg agg gta ttt ttg aat aat tac       336
Asp Glu Phe Asn Ala Tyr Tyr Ala Arg Arg Val Phe Leu Asn Asn Tyr
        100                 105                 110 caa gca gcc gaa gac cac cca cga atg gtt atc tta cga ctg tta cgt       384
Gln Ala Ala Glu Asp His Pro Arg Met Val Ile Leu Arg Leu Leu Arg
        115                 120                 125 tac att gtc cgc ctg gtg tgg aga atg cat tg                            416
Tyr Ile Val Arg Leu Val Trp Arg Met His
        130                 135

<210> SEQ ID NO 8
<211> LENGTH: 138
<212> TYPE: PRT
<213> ORGANISM: Homo sapiens

<400> SEQUENCE: 8

Met Ala Lys Gln Pro Ser Asp Val Ser Ser Glu Cys Asp Arg Glu Gly
 1               5                  10                  15

Arg Gln Leu Gln Pro Ala Glu Arg Pro Pro Gln Leu Arg Pro Gly Ala
             20                  25                  30

Pro Thr Ser Leu Gln Thr Glu Pro Gln Asp Arg Ser Pro Ala Pro Met
         35                  40                  45

Ser Cys Asp Lys Ser Thr Gln Thr Pro Ser Pro Pro Cys Gln Ala Phe
 50                  55                  60

Asn His Tyr Leu Ser Ala Met Ala Ser Met Arg Gln Ala Glu Pro Ala
 65                  70                  75                  80

Asp Met Arg Pro Glu Ile Trp Ile Ala Gln Glu Leu Arg Arg Ile Gly
             85                  90                  95

Asp Glu Phe Asn Ala Tyr Tyr Ala Arg Arg Val Phe Leu Asn Asn Tyr
        100                 105                 110

Gln Ala Ala Glu Asp His Pro Arg Met Val Ile Leu Arg Leu Leu Arg
        115                 120                 125

Tyr Ile Val Arg Leu Val Trp Arg Met His
        130                 135

<210> SEQ ID NO 9
<211> LENGTH: 596
<212> TYPE: DNA
<213> ORGANISM: Homo sapiens
<220> FEATURE:
<221> NAME/KEY: CDS
<222> LOCATION: (1)..(594)

<400> SEQUENCE: 9
```

-continued

```
atg gca aag caa cct tct gat gta agt tct gag tgt gac cga gaa ggt      48
Met Ala Lys Gln Pro Ser Asp Val Ser Ser Glu Cys Asp Arg Glu Gly
 1               5                  10                  15 aga caa ttg cag cct gcg gag agg cct ccc cag ctc aga cct ggg gcc      96
Arg Gln Leu Gln Pro Ala Glu Arg Pro Pro Gln Leu Arg Pro Gly Ala
             20                  25                  30 cct acc tcc cta cag aca gag cca caa ggt aat cct gaa ggc aat cac     144
Pro Thr Ser Leu Gln Thr Glu Pro Gln Gly Asn Pro Glu Gly Asn His
         35                  40                  45 gga ggt gaa ggg gac agc tgc ccc cac ggc agc cct cag ggc ccg ctg     192
Gly Gly Glu Gly Asp Ser Cys Pro His Gly Ser Pro Gln Gly Pro Leu
     50                  55                  60 gcc cca cct gcc agc cct ggc cct ttt gct acc aga tcc ccg ctt ttc     240
Ala Pro Pro Ala Ser Pro Gly Pro Phe Ala Thr Arg Ser Pro Leu Phe
 65                  70                  75                  80 atc ttt atg aga aga tcc tcc ctg ctg tct cga tcc tcc agt ggg tat     288
Ile Phe Met Arg Arg Ser Ser Leu Leu Ser Arg Ser Ser Ser Gly Tyr
                 85                  90                  95 ttc tct ttt gac aca gac agg agc cca gca ccc atg agt tgt gac aaa     336
Phe Ser Phe Asp Thr Asp Arg Ser Pro Ala Pro Met Ser Cys Asp Lys
            100                 105                 110 tca aca caa acc cca agt cct cct tgc cag gcc ttc aac cac tat ctc     384
Ser Thr Gln Thr Pro Ser Pro Pro Cys Gln Ala Phe Asn His Tyr Leu
        115                 120                 125 agt gca atg gct tcc atg agg cag gct gaa cct gca gat atg cgc cca     432
Ser Ala Met Ala Ser Met Arg Gln Ala Glu Pro Ala Asp Met Arg Pro
    130                 135                 140 gag ata tgg atc gcc caa gag ttg cgg cgt atc gga gac gag ttt aac     480
Glu Ile Trp Ile Ala Gln Glu Leu Arg Arg Ile Gly Asp Glu Phe Asn
145                 150                 155                 160 gct tac tat gca agg agg gta ttt ttg aat aat tac caa gca gcc gaa     528
Ala Tyr Tyr Ala Arg Arg Val Phe Leu Asn Asn Tyr Gln Ala Ala Glu
                165                 170                 175 gac cac cca cga atg gtt atc tta cga ctg tta cgt tac att gtc cgc     576
Asp His Pro Arg Met Val Ile Leu Arg Leu Leu Arg Tyr Ile Val Arg
            180                 185                 190 ctg gtg tgg aga atg cat tg                                          596
Leu Val Trp Arg Met His
        195
```

<210> SEQ ID NO 10
<211> LENGTH: 198
<212> TYPE: PRT
<213> ORGANISM: Homo sapiens

<400> SEQUENCE: 10

```
Met Ala Lys Gln Pro Ser Asp Val Ser Ser Glu Cys Asp Arg Glu Gly
 1               5                  10                  15

Arg Gln Leu Gln Pro Ala Glu Arg Pro Pro Gln Leu Arg Pro Gly Ala
             20                  25                  30

Pro Thr Ser Leu Gln Thr Glu Pro Gln Gly Asn Pro Glu Gly Asn His
         35                  40                  45

Gly Gly Glu Gly Asp Ser Cys Pro His Gly Ser Pro Gln Gly Pro Leu
     50                  55                  60

Ala Pro Pro Ala Ser Pro Gly Pro Phe Ala Thr Arg Ser Pro Leu Phe
 65                  70                  75                  80

Ile Phe Met Arg Arg Ser Ser Leu Leu Ser Arg Ser Ser Ser Gly Tyr
                 85                  90                  95
```

```
Phe Ser Phe Asp Thr Asp Arg Ser Pro Ala Pro Met Ser Cys Asp Lys
                100                 105                 110

Ser Thr Gln Thr Pro Ser Pro Pro Cys Gln Ala Phe Asn His Tyr Leu
        115                 120                 125

Ser Ala Met Ala Ser Met Arg Gln Ala Glu Pro Ala Asp Met Arg Pro
    130                 135                 140

Glu Ile Trp Ile Ala Gln Glu Leu Arg Arg Ile Gly Asp Glu Phe Asn
145                 150                 155                 160

Ala Tyr Tyr Ala Arg Arg Val Phe Leu Asn Asn Tyr Gln Ala Ala Glu
                165                 170                 175

Asp His Pro Arg Met Val Ile Leu Arg Leu Leu Arg Tyr Ile Val Arg
            180                 185                 190

Leu Val Trp Arg Met His
        195

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Tyr Lys Asp Asp Asp Asp Lys
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Glu Tyr Met Pro Met Glu
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Leu Arg Arg Ile Gly Asp Glu
1               5

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 14
tgggagaaca gggtacatcg atgcggg                                         27

<210> SEQ ID NO 15
<211> LENGTH: 22
<212> TYPE: DNA
```

-continued

```
<213> ORGANISM: Artificial Sequence
<220> FEATURE:
<223> OTHER INFORMATION: Description of Artificial Sequence: Primer

<400> SEQUENCE: 15
gtgaactggg agcggattgt gg                                              22

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 16
cacctgcaca ccgcgatcca ggataacg                                        28

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 17
aggatccacc atggccaagc aacc                                            24

<210> SEQ ID NO 18
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 18
gttctagatc agcacatctc tctgggatag aaccac                               36

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 19
gcaagcttcc tgtgcaatcc gtatctcc                                        28

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 20
ggaagcttgc aacgaaactt acacaaggtg                                      30

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 21
gcaagcttcc gggcgcagat cttc                                            24
```

```
<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 22
caaagcttcc tgtgcaatcc gtatctcc                                          28

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 23
ggaagctttg aacgaaactt acacaaggtg                                        30

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 24
caaagcttcc gggcgcagat cttc                                              24

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 25
taagttctga gtgtgacaga gaaggtgg                                          28

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 26
cagttgtaag ataaccattt gagggtgg                                          28

<210> SEQ ID NO 27
<211> LENGTH: 18
<212> TYPE: PRT
<213> ORGANISM: Homo sapiens

<400> SEQUENCE: 27

Val Val His Leu Thr Leu Arg Gln Ala Gly Asp Asp Phe Ser Arg Arg
 1               5                  10                  15

Tyr Arg

<210> SEQ ID NO 28
<211> LENGTH: 18
<212> TYPE: PRT
<213> ORGANISM: Homo sapiens
```

<400> SEQUENCE: 28

Ala Val Lys Gln Ala Leu Arg Glu Ala Gly Asp Glu Phe Glu Leu Arg
1               5                   10                  15

Tyr Arg

<210> SEQ ID NO 29
<211> LENGTH: 18
<212> TYPE: PRT
<213> ORGANISM: Homo sapiens

<400> SEQUENCE: 29

Pro Leu His Gln Ala Met Arg Ala Ala Gly Asp Glu Phe Glu Thr Arg
1               5                   10                  15

Phe Arg

<210> SEQ ID NO 30
<211> LENGTH: 18
<212> TYPE: PRT
<213> ORGANISM: Homo sapiens

<400> SEQUENCE: 30

Lys Ala Leu Glu Thr Leu Arg Arg Val Gly Asp Gly Val Gln Arg Asn
1               5                   10                  15

His Glu

<210> SEQ ID NO 31
<211> LENGTH: 18
<212> TYPE: PRT
<213> ORGANISM: Homo sapiens

<400> SEQUENCE: 31

Lys Leu Ser Glu Cys Leu Lys Arg Ile Gly Asp Glu Leu Asp Ser Asn
1               5                   10                  15

Met Glu

<210> SEQ ID NO 32
<211> LENGTH: 18
<212> TYPE: PRT
<213> ORGANISM: Homo sapiens

<400> SEQUENCE: 32

Gln Val Gly Arg Gln Leu Ala Ile Ile Gly Asp Asp Ile Asn Arg Arg
1               5                   10                  15

Tyr Asp

<210> SEQ ID NO 33
<211> LENGTH: 18
<212> TYPE: PRT
<213> ORGANISM: Homo sapiens

<400> SEQUENCE: 33

Arg Tyr Gly Arg Glu Leu Arg Arg Met Ser Asp Glu Phe Val Asp Ser
1               5                   10                  15

Phe Lys

<210> SEQ ID NO 34
<211> LENGTH: 18
<212> TYPE: PRT
<213> ORGANISM: Homo sapiens

```
<400> SEQUENCE: 34

Ala Leu Ala Leu Arg Leu Ala Cys Ile Gly Asp Glu Met Asp Val Ser
 1               5                  10                  15
Leu Arg

<210> SEQ ID NO 35
<211> LENGTH: 18
<212> TYPE: PRT
<213> ORGANISM: Homo sapiens

<400> SEQUENCE: 35

Asn Ile Ala Arg His Leu Ala Gln Val Gly Asp Ser Met Asp Arg Ser
 1               5                  10                  15
Ile Pro

<210> SEQ ID NO 36
<211> LENGTH: 18
<212> TYPE: PRT
<213> ORGANISM: Homo sapiens

<400> SEQUENCE: 36

Leu Thr Ala Ala Arg Leu Lys Ala Leu Gly Asp Glu Leu His Gln Arg
 1               5                  10                  15
Thr Met

<210> SEQ ID NO 37
<211> LENGTH: 18
<212> TYPE: PRT
<213> ORGANISM: Homo sapiens

<400> SEQUENCE: 37

Trp Ile Ala Gln Glu Leu Arg Arg Ile Gly Asp Glu Phe Asn Ala Tyr
 1               5                  10                  15
Tyr Ala

<210> SEQ ID NO 38
<211> LENGTH: 20
<212> TYPE: PRT
<213> ORGANISM: Homo sapiens

<400> SEQUENCE: 38

Met Arg Pro Glu Ile Trp Ile Ala Gln Glu Leu Arg Arg Ile Gly Asp
 1               5                  10                  15
Glu Phe Asn Ala
            20

<210> SEQ ID NO 39
<211> LENGTH: 20
<212> TYPE: PRT
<213> ORGANISM: Caenorhabditis elegans

<400> SEQUENCE: 39

Gln Glu Glu Thr Ile Arg Trp Ala Gln Glu Leu Arg Leu Arg Cys Leu
 1               5                  10                  15
Val Thr Thr Arg
            20
```